(12) United States Patent
Bertin

(10) Patent No.: US 6,613,521 B1
(45) Date of Patent: Sep. 2, 2003

(54) MOLECULES OF THE CARD-RELATED PROTEIN FAMILY AND USES THEREOF

(75) Inventor: John Bertin, Watertown, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 83 days.

(21) Appl. No.: 09/865,364

(22) Filed: May 25, 2001

Related U.S. Application Data

(60) Division of application No. 09/207,359, filed on Dec. 8, 1998, now Pat. No. 6,469,140, which is a continuation-in-part of application No. 09/099,041, filed on Jun. 17, 1998, now Pat. No. 6,340,576, which is a continuation-in-part of application No. 09/019,942, filed on Feb. 6, 1998, now Pat. No. 6,033,855.

(51) Int. Cl.[7] .................. C07H 21/04; C07K 14/00; C12Q 1/68; G01N 33/53

(52) U.S. Cl. .................. 435/6; 435/7.1; 435/4; 536/23.1; 530/300; 530/350

(58) Field of Search .................. 435/6, 7.1, 4; 536/23.1; 540/300, 350

(56) References Cited

FOREIGN PATENT DOCUMENTS

| DE | 19813839 | 9/1999 |
|---|---|---|
| WO | WO 98/55507 | 12/1998 |
| WO | WO 99/40102 | 8/1999 |
| WO | WO 99/47669 | 9/1999 |
| WO | WO 00/06728 | 2/2000 |

OTHER PUBLICATIONS

Hofmann et al., "The CARD Domain: A new apoptotic signalling motif" TIBS 22:155–156, 1997.
McCarthy et al., "RIP2 is a novel NF–kB–Activating and cell death–inducing kinase" J. of Biol. Chem. 273(27):16968–16975, 1998.
Yan et al., "mE10, a novel caspase recruitment domain–containing proapoptotic molecule" J. of Biol Chem. 274(15):10287–10292, 1999.
Masumoto et al., "ASC, a Novel 22–kDa Protein, Aggregates During Apoptosis of . . . " J. of Biol. Chem. 274(48):33835–33838, 1999.
GenBank Accession No. AB023416, Masumoto et al, Dec. 1, 1999.
GenBank Accession No. AI148558, Strausberg, Oct. 28, 1998.
GenBank Accession No. AI346818, Strausberg, Feb. 2, 1999.
GenBank Accession No. AA528254, Strausberg, Aug. 5, 1997.
GenBank Accession No. AA573948, Strausberg, Sep. 12, 1997.
GenBank Accession No. AA582937, Strausberg, Sep. 26, 1997.
GenBank Accession No. AA278825, Strausberg, Aug. 15, 1997.
GenBank Accession No. AI262374, Strausberg, Nov. 13, 1998.
GenBank Accession No. AI587178, Strausberg, May 14, 1999.
GenBank Accession No. R84288, Wilson, Aug. 14, 1995.
GenBank Accession No. AA302352, Kerlavage, Apr. 18, 1997.
GenBank Accession No. AI570067, Strausberg, May 14, 1999.
GenBank Accession No. AW196663, Strausberg, Nov. 29, 1999.
GenBank Accession No. AW192194, Strausberg, Nov. 29, 1999.
PCT Written Opinion dated Jun. 18, 2001 For PCT/US00/17691.
Bertin et al., "Human CARD4 Protein Is a Novel CED–4/Apaf–1 Cell Death Family Member . . . " J. of Biol. Chem. 274:12955–12958, 1999.
Duan et al., "RAIDD is a New Death Adaptor Molecule" Nature 385:86–89, 1997.
Epstein, "Nuclear Factor–kB–A Pivotal Transcription Factor in Chronic Inflammatory Diseases" NE J. of Med. 336:1066–1071, 1997.
Hoffman, et al., "The CARD domain: A New Apoptotic Signalling Motif" TIBS 22:155–156, 1997.
Hu et al., "Bcl–$X_L$ Interacts with Apaf–1 and Inhibits Apaf–1–dependent Caspase–9 Activation" Proc. Nat'l Acad. Of Sci USA 95:4386–4391, 1998.
Inohara et al., "RICK, A Novel Protein Kinase Containing a Caspase Recruitment Domain, . . . " J. of Biol.Chem. 273:12296–12300, 1988.

(List continued on next page.)

*Primary Examiner*—Sean McGarry
(74) *Attorney, Agent, or Firm*—Millennium Pharmaceuticals, Inc.

(57) ABSTRACT

Novel CARD-3, CARD-4L, CARD-4S, CARD-4Y, CARD-4Z, and murine CARD-4L polypeptides, proteins, and nucleic acid molecules are disclosed. In addition to isolated CARD-3, CARD-4L, CARD-4S, CARD-4Y, CARD-4Z, and murine CARD-4L proteins, and the invention further provides CARD-3, CARD-4L, CARD-4S, CARD-4Y, CARD-4Z, and murine CARD-4L fusion proteins, antigenic peptides and anti-CARD-3, anti-CARD-4L and anti-CARD-4S, anti-CARD-4Y, anti-CARD-4Z, and anti-murine CARD-4L antibodies. The invention also provides CARD-3, CARD-4L, CARD-4S, CARD-4Y, CARD-4Z, and murine CARD-4L nucleic acid molecules, recombinant expression vectors containing a nucleic acid molecule of the invention, host cells into which the expression vectors have been introduced and non-human transgenic animals in which a CARD-3, CARD-4L, CARD-4S, CARD-4Y, CARD-4Z, and murine CARD-4L gene has been introduced or disrupted. The invention further provides CARD-3 and CARD-4 target proteins that bind to CARD-3 or CARD-4 and allelic variants of human CARD-4. Diagnostic, screening and therapeutic methods utilizing compositions of the invention are also provided.

22 Claims, 26 Drawing Sheets

OTHER PUBLICATIONS

Inohara et al., "NOD1, an Apaf–1–like Activator of Caspase–9 and Nuclear Factor kB" J. of Biol. Chem. 274:14560–14567, 1999.

Li et al., "Cytochrome C and dATP–Dependent Formation of Apaf–1/Caspase–9 Complex . . . " Cell 91:479–489, 1997.

Marra et al., EMBL Accession No. AA620157, Sep. 12, 1996.

Miura et al. "Induction of Apoptosis in Fibroblasts by IL–1B–Converting Enzyme, . . . " Cell 75:653–660, 1993.

Navab et al., "Pathogenesis of Atherosclerosis" American J. of Cardiology 76:18C–23C, 1995.

CCACGCGTCCGGTCAGCTCTGGTTCGGAGAAGCAGCGGCTGGCGTGGGCCATCCGGGGAATGGGC
GCCCTCGTGACCTAGTGTTGCGGGGCAAAAAGGGTCTTGCCGGCCTCGCTCGTGCAGGGGCGTAT
CTGGGCGCCTGAGCGCGGCGTGGGAGCCTTGGGAGCCGCCGCAGCAGGGGGCACACCCGGAACCG
GCCTGAGCGCCCGGGACCATGAACGGGGAGGCCATCTGCAGCGCCCTGCCCACCATTCCCTACCA
CAAACTCGCCGACCTGCGCTACCTGAGCCGCGGCGCCTCTGGCACTGTGTCGTCCGCCCGCCACG
CAGACTGGCGCGTCCAGGTGGCCGTGAAGCACCTGCACATCCACACTCCGCTGCTCGACAGTGAA
AGAAAGGATGTCTTAAGAAGCTGAAATTTTACACAAAGCTAGATTTAGTTACATTCTTCCAAT
TTTGGGAATTTGCAATGAGCCTGAATTTTTGGGAATAGTTACTGAATACATGCCAAATGGATCAT
TAAATGAACTCCTACATAGGAAAACTGAATATCCTGATGTTGCTTGGCCATTGAGATTTCCTATC
CTGCATGAAATTGCCCTTGGTGTAAATTACCTGCACAATATGACTCCTCCTTTACTTCATCATGA
CTTGAAGACTCAGAATATCTTATTGGACAATGAATTTCATGTTAAGATTGCAGATTTTGGTTTAT
CAAAGTGGCGCATGATGTCCCTCTCACAGTCACGAAGTAGCAAATCTGCACCAGAAGGAGGGACA
ATTATCTATATGCCACCTGAAAACTATGAACCTGGACAAAAATCAAGGGCCAGTATCAAGCACGA
TATATATAGCTATGCAGTTATCACATGGGAAGTGTTATCCAGAAAACAGCCTTTTGAAGATGTCA
CCAATCCTTTGCAGATAATGTATAGTGTGTCACAAGGACATCGACCTGTTATTAATGAAGAAAGT
TTGCCATATGATATACCTCACCGAGCACGTATGATCTCTCTAATAGAAAGTGGATGGGCACAAAA
TCCAGATGAAAGACCATCTTTCTTAAAATGTTTAATAGAACTTGAACCAGTTTTGAGAACATTTG
AAGAGATAACTTTTCTTGAAGCTGTTATTCAGCTAAAGAAAACAAAGTTACAGAGTGTTTCAAGT
GCCATTCACCTATGTGACAAGAAGAAAATGGAATTATCTCTGAACATACCTGTAAATCATGGTCC
ACAAGAGGAATCATGTGGATCCTCTCAGCTCCATGAAAATAGTGGTTCTCCTGAAACTTCAAGGT
CCCTGCCAGCTCCTCAAGACAATGATTTTTATCTAGAAAGCTCAAGACTGTTATTTATGAAG
CTGCATCACTGTCCTGGAAATCACAGTTGGGATAGCACCATTTCTGGATCTCAAAGGGCTGCATT
CTGTGATCACAAGACCATTCCATGCTCTTCAGCAATAATAAATCCACTCAACTGCAGGAAACT
CAGAACGTCTGCAGCCTGGTATAGCCCAGCAGTGGATCCAGAGCAAAAGGGAAGACATTGTGAAC
CAAATGACAGAAGCCTGCCTTAACCAGTCGCTAGATGCCCTTCTGTCCAGGGACTTGATCATGAA
AGAGGACTATGAACTTGTTAGTACCAAGCCTACAAGGACCTCAAAAGTCAGACAATTACTAGACA
CTACTGACATCCAAGGAGAAGAATTTGCCAAAGTTATAGTACAAAAATTGAAAGATAACAAACAA
ATGGGTCTTCAGCCTTACCCGGAAATACTTGTGGTTTCTAGATCACCATCTTTAAATTTACTTCA
AAATAAAAGCATGTAAGTGACTGTTTTTCAAGAAGAAATGTGTTTCATAAAAGGATATTTATAAA
AAAAAAAAAAAAAAAAAAAAAAAAAAAAAAAAAAAAAAAAAAAA  (SEQ ID NO:1)

```
TTTTTATGGG AATCGCAGCT TGGAAGAGAC AGARCAATTC CAGAAWTAAA TTGRAATTGA
AGATTTAACC AATGTTGTTT TAAAATATTC TAACTTCAAA GAATGATGCC AGAACTTWAA
AAGGGRCTGC GCAGAGTAGC AGGGGCCCTG GAGGGCGCGG CCTGAATCCT GATTGCCCTT
CTGCTGAGAG GACACACGCA GCTGAAGATG AATTTGGGAA AAGTAGCCGC TTGCTACTTT
AACTATGGAA GAGCAGGGCC ACAGTGAGAT GGAAATAATC CCATCAGAGT CTCACCCCCA
CATTCAATTA CTGAAAAGCA ATCGGGAACT TCTGGTCACT CACATCCGCA ATACTCAGTG
TCTGGTGGAC AACTTGCTGA AGAATGACTA CTTCTCGGCC GAAGATGCGG AGATTGTGTG
TGCCTGCCCC ACCCAGCCTG ACAAGGTCCG CAAAATTCTG GACCTGGTAC AGAGCAAGGG
CGAGGAGGTG TCCGAGTTCT TCCTCTACTT GCTCCAGCAA CTCGCAGATG CCTACGTGGA
CCTCAGGCCT TGGCTGCTGG AGATCGGCTT CTCCCCTTCC CTGCTCACTC AGAGCAAAGT
CGTGGTCAAC ACTGACCCAG TGAGCAGGTA TACCCAGCAG CTGCGACACC ATCTGGGCCG
TGACTCCAAG TTCGTGCTGT GCTATGCCCA GAAGGAGGAG CTGCTGCTGG AGGAGATCTA
CATGGACACC ATCATGGAGC TGGTTGGCTT CAGCAATGAG AGCCTGGGCA GCCTGAACAG
CCTGGCCTGC CTCCTGGACC ACACCACCGG CATCCTCAAT GAGCAGGGTG AGACCATCTT
CATCCTGGGT GATGCTGGGG TGGGCAAGTC CATGCTGCTA CAGCGGCTGC AGAGCCTCTG
GGCCACGGGC CGGCTAGACG CAGGGGTCAA ATTCTTCTTC CACTTTCGCT GCCGCATGTT
CAGCTGCTTC AAGGAAAGTG ACAGGCTGTG TCTGCAGGAC CTGCTCTTCA AGCACTACTG
CTACCCAGAG CGGGACCCCG AGGAGGTGTT TGCCTTCCTG CTGCGCTTCC CCACGTGGC
CCTCTTCACC TTCGATGGCC TGGACGAGCT GCACTCGGAC TTGGACCTGA GCCGCGTGCC
TGACAGCTCC TGCCCCTGGG AGCCTGCCCA CCCCCTGGTC TTGCTGGCCA ACCTGCTCAG
TGGGAAGCTG CTCAAGGGGG CTAGCAAGCT GCTCACAGCC CGCACAGGCA TCGAGGTCCC
GCGCCAGTTC CTGCGGAAGA AGGTGCTTCT CCGGGGCTTC TCCCCCAGCC ACCTGCGCGC
CTATGCCAGG AGGATGTTCC CCGAGCGGGC CCTGCAGGAC CGCCTGCTGA GCCAGCTGGA
GGCCAACCCC AACCTCTGCA GCCTGTGCTC TGTGCCCCTC TTCTGCTGGA TCATCTTCCG
GTGCTTCCAG CACTTCCGTG CTGCCTTTGA AGGCTCACCA CAGCTGCCCG ACTGCACGAT
GACCCTGACA GATGTCTTCC TCCTGGTCAC TGAGGTCCAT CTGAACAGGA TGCAGCCCAG
CAGCCTGGTG CAGCGGAACA CACGCAGCCC AGTGGAGACC CTCCACGCCG GCCGGGACAC
TCTGTGCTCG CTGGGGCAGG TGGCCCACCG GGGCATGGAG AAGAGCCTCT TGTCTTCAC
CCAGGAGGAG GTGCAGGCCT CCGGGCTGCA GGAGAGAGAC ATGCAGCTGG GCTTCCTGCG
GGCTTTGCCG GAGCTGGGCC CCGGGGGTGA CCAGCAGTCC TATGAGTTTT TCCACCTCAC
CCTCCAGGCC TTCTTTACAG CCTTCTTCCT CGTGCTGGAC GACAGGGTGG GCACTCAGGA
GCTGCTCAGG TTCTTCCAGG AGTGGATGCC CCCTGCGGGG GCAGCGACCA CGTCCTGCTA
```

FIG. 3A

```
TCCTCCCTTC CTCCCGTTCC AGTGCCTGCA GGGCAGTGGT CCGGCGCGGG AAGACCTCTT
CAAGAACAAG GATCACTTCC AGTTCACCAA CCTCTTCCTG TGCGGGCTGT TGTCCAAAGC
CAAACAGAAA CTCCTGCGGC ATCTGGTGCC CGCGGCAGCC CTGAGGAGAA AGCGCAAGGC
CCTGTGGGCA CACCTGTTTT CCAGCCTGCG GGCTACCTG AAGAGCCTGC CCCGCGTTCA
GGTCGAAAGC TTCAACCAGG TGCAGGCCAT GCCCACGTTC ATCTGGATGC TGCGCTGCAT
CTACGAGACA CAGAGCCAGA AGGTGGGGCA GCTGGCGGCC AGGGCATCT GCGCCAACTA
CCTCAAGCTG ACCTACTGCA ACGCCTGCTC GGCCGACTGC AGCGCCCTCT CCTTCGTCCT
GCATCACTTC CCCAAGCGGC TGGCCCTAGA CCTAGACAAC AACAATCTCA ACGACTACGG
CGTGCGGGAG CTGCAGCCCT GCTTCAGCCG CCTCACTGTT CTCAGACTCA GCGTAAACCA
GATCACTGAC GGTGGGGTAA AGGTGCTAAG CGAAGAGCTG ACCAAATACA AAATTGTGAC
CTATTTGGGT TTATACAACA ACCAGATCAC CGATGTCGGA GCCAGGTACG TCACCAAAAT
CCTGGATGAA TGCAAAGGCC TCACGCATCT TAAACTGGGA AAAAACAAAA TAACAAGTGA
AGGAGGGAAG TATCTCGCCC TGGCTGTGAA GAACAGCAAA TCAATCTCTG AGGTTGGGAT
GTGGGGCAAT CAAGTTGGGG ATGAAGGAGC AAAAGCCTTC GCAGAGGCTC TGCGGAACCA
CCCCAGCTTG ACCACCCTGA GTCTTGCGTC CAACGGCATC TCCACAGAAG GAGGAAAGAG
CCTTGCGAGG GCCCTGCAGC AGAACACGTC TCTAGAAATA CTGTGGCTGA CCCAAAATGA
ACTCAACGAT GAAGTGGCAG AGAGTTTGGC AGAAATGTTG AAAGTCAACC AGACGTTAAA
GCATTTATGG CTTATCCAGA ATCAGATCAC AGCTAAGGGG ACTGCCCAGC TGGCAGATGC
GTTACAGAGC AACACTGGCA TAACAGAGAT TTGCCTAAAT GGAAACCTGA TAAAACCAGA
GGAGGCCAAA GTCTATGAAG ATGAGAAGCG GATTATCTGT TTCTGAGAGG ATGCTTTCCT
GTTCATGGGG TTTTTGCCCT GGAGCCTCAG CAGCAAATGC CACTCTGGGC AGTCTTTTGT
GTCAGTGTCT TAAAGGGGCC TGCGCAGGCG GGACTATCAG GAGTCCACTG CCTYCATGAT
GCAAGCCAGC TTCCTGTGCA GAAGGTCTGG TCGGCAAACT CCCTAAGTAC CCGCTACAAT
TCTGCAGAAA AAGAATGTGT CTTGCGAGCT GTTGTAGTTA CAGTAAATAC ACTGTGAAGA
GAAAAAAAAA ACGGACGCGT GG    (SEQ ID NO:7)
```

FIG. 3B

```
MEEQGHSEMEIIPSESHPHIQLLKSNRELLVTHIRNTQCLVDNLLKNDYFSAEDAEIVCACPTQP
DKVRKILDLVQSKGEEVSEFFLYLLQQLADAYVDLRPWLLEIGFSPSLLTQSKVVVNTDPVSRYT
QQLRHHLGRDSKFVLCYAQKEELLLEEIYMDTIMELVGFSNESLGSLNSLACLLDHTTGILNEQG
ETIFILGDAGVGKSMLLQRLQSLWATGRLDAGVKFFFHFRCRMFSCFKESDRLCLQDLLFKHYCY
PERDPEEVFAFLLRFPHVALFTFDGLDELHSDLDLSRVPDSSCPWEPAHPLVLLANLLSGKLLKG
ASKLLTARTGIEVPRQFLRKKVLLRGFSPSHLRAYARRMFPERALQDRLLSQLEANPNLCSLCSV
PLFCWIIFRCFQHFRAAFEGSPQLPDCTMTLTDVFLLVTEVHLNRMQPSSLVQRNTRSPVETLHA
GRDTLCSLGQVAHRGMEKSLFVFTQEEVQASGLQERDMQLGFLRALPELGPGGDQQSYEFFHLTL
QAFFTAFFLVLDDRVGTQELLRFFQEWMPPAGAATTSCYPPFLPFQCLQGSGPAREDLFKNKDHF
QFTNLFLCGLLSKAKQKLLRHLVPAAALRRKRKALWAHLFSSLRGYLKSLPRVQVESFNQVQAMP
TFIWMLRCIYETQSQKVGQLAARGICANYLKLTYCNACSADCSALSFVLHHFPKRLALDLDNNNL
NDYGVRELQPCFSRLTVLRLSVNQITDGGVKVLSEELTKYKIVTYLGLYNNQITDVGARYVTKIL
DECKGLTHLKLGKNKITSEGGKYLALAVKNSKSISEVGMWGNQVGDEGAKAFAEALRNHPSLTTL
SLASNGISTEGGKSLARALQQNTSLEILWLTQNELNDEVAESLAEMLKVNQTLKHLWLIQNQITA
KGTAQLADALQSNTGITEICLNGNLIKPEEAKVYEDEKRIICF (SEQ ID NO:8)
```

FIG. 4

```
CACGCGTCCGACTTGCTGAAGAATGACTACTTCTCGGCCGAAGATGCGGAGATTGTGT
GTGCCTGCCCCACCCAGCCTGACAAGGTCCGCAAAATTCTGGACCTGGTACAGAGCAAG
GGCGAGGAGGTGTCCGAGTTCTTCCTCTACTTGCTCCAGCAACTCGCAGATGCCTACGT
GGACCTCAGGCCTTGGCTGCTGGAGATCGGCTTCTCCCCTTCCCTGCTCACTCAGAGCA
AAGTCGTGGTCAACACTGACCCAGTGAGCAGGTATACCCAGCAGCTGCGACACCATCTG
GGCCGTGACTCCAAGTTCGTGCTGTGCTATGCCCAGAAGGAGGAGCTGCTGCTGGAGGA
GATCTACATGGACACCATCATGGAGCTGGTTGGCTTCAGCAATGAGAGCCTGGGCAGCC
TGAACAGCCTGGCCTGCCTCCTGGACCACACCACCGGCATCCTCAATGAGCAGGGTGAG
ACCATCTTCATCCTGGGTGATGCTGGGGTGGGCAAGTCCATGCTGCTACAGCGGCTGCA
GAGCCTCTGGGCCACGGGCCGGCTAGACGCAGGGGTCAAATTCTTCTTCCACTTTCGCT
GCCGCATGTTCAGCTGCTTCAAGGAAAGTGACAGGCTGTGTCTGCAGGACCTGCTCTTC
AAGCACTACTGCTACCCAGAGCGGGACCCCGAGGAGGTGTTTGCCTTCCTGCTGCGCTT
CCCCCACGTGGCCCTCTTCACCTTCGATGGCCTGGACGAGCTGCACTCGGACTTGGACC
TGAGCCGCGTGCCTGACAGCTCCTGCCCCTGGGAGCCTGCCCACCCCTGGTCTTGCTG
GCCAACCTGCTCAGTGGGAAGCTGCTCAAGGGGGCTAGCAAGCTGCTCACAGCCCGCAC
AGGCATCGAGGTCCCGCGCCAGTTCCTGCGGAAGAAGGTGCTTCTCCGGGGCTTCTCCC
CCAGCCACCTGCGCGCCTATGCCAGGAGGATGTTCCCCGAGCGGGCCCTGCAGGACCGC
CTGCTGAGCCAGCTGGAGGCCAACCCCAACCTCTGCAGCCTGTGCTCTGTGCCCCTCTT
CTGCTGGATCATCTTCCGGTGCTTCCAGCACTTCCGTGCTGCCTTTGAAGGCTCACCAC
AGCTGCCCGACTGCACGATGACCCTGACAGATGTCTTCCTCCTGGTCACTGAGGTCCAT
CTGAACAGGATGCAGCCCAGCAGCCTGGTGCAGCGGAACACACGCAGCCCAGTGGAGAC
CCTCCACGCCGGCCGGGACACTCTGTGCTCGCTGGGGCAGGTGGCCCACCGGGGCATGG
AGAAGAGCCTCTTTGTCTTCACCCAGGAGGAGGTGCAGGCCTCCGGGCTGCAGGAGAGA
GACATGCAGCTGGGCTTCCTGCGGGCTTTGCCGGAGCTGGGCCCCGGGGTGACCAGCA
GTCCTATGAGTTTTTCCACCTCAGCCTCCTCACCTGTAAAACTGGGATCCCAGTATAGA
CTTTGGAAATCAGTAGACACCATATGCTTCAAAAAACAGGGGCTATTAAAATGACATCA
GGAGCCAGAAAGTCTCATGGCTGTGCTTTCTCTTGAAGTTTATACAACAACCAGATCAC
CGATGTCGGAGCCAGACTGGGAAAAAACAAAATAACAAGTGAAGGAGGGAAGTATCTCG
CCCTGGCTGTGAAGAACAGCAAATCAATCTCTGAGGTTGGGATGTGGGCAATCAAGTT
GGGGATGAAGGAGCAAAAGCCTTCGCAGAGGCTCTGCGGAACCACCCCAGCTTGACCAC
CCTGAGTCTTGCGTCCAACGGCATCTCCACAGAAGGAGGAAAGAGCCTTGCGAGGGCCC
TGCAGCAGAACACGTCTCTAGAAATACTGTGGCTGACCCAAAATGAACTCAACGATGAA
GTGGCAGAGAGTTTGGCAGAAATGTTGAAAGTCAACCAGACGTTAAAGCATTTATGGCT
TATCCAGAATCAGATCACAGTCTTTTGTGTCAGTGTCTTAAAGGGGCCTGCGCAGGCGG
GACTATCAGGAGTCCACTGCCTCCATGATGCAAGCCAGCTTCCTGTGCAGAAGGTCTGG
TCGGCAAACTCCCTAAGTACCCGCTACAATTCTGCAGAAAAGAATGTGTCTTGCGAGC
TGTTGTAGTTACAGTAAATACACTGTGAAGAGACTTTATTGCCTATTATAATTATTTTT
ATCTGAAGCTAGAGGAATAAAGCTGTGAGCAAACAGAGGAGGCCAGCCTCACCTCATTC
CAACACCTGCCATAGGGACCAACGGGAGCGAGTTGGTCACCGCTCTTTTCATTGAAGAG
TTGAGGATGTGGCACAAAGTTGGTGCCAAGCTTCTTGAATAAAACGTGTTTGATGGATT
AGTATTATACCTGAAATATTTTCTTCCTTCTCAGCACTTTCCCATGTATTGATACTGGT
CCCACTTCACAGCTGGAGACACCGGAGTATGTGCAGTGTGGGATTTGACTCCTCCAAGG
TTTTGTGGAAAGTTAATGTCAAGGAAAGGATGCACCACGGGCTTTTAATTTAATCCTG
GAGTCTCACTGTCTGCTGGCAAAGATAGAGAATGCCCTCAGCTCTTAGCTGGTCTAAGA
ATGACGATGCCTTCAAAATGCTGCTTCCACTCAGGGCTTCTCCTCTGCTAGGCTACCCT
CCTCTAGAAGGCTGAGTACCATGGGCTACAGTGTCTGGCCTTGGAAGAAGTGATTCTG
TCCCTCCAAAGAAATAGGGCATGGCTTGCCCCTGTGGCCCTGGCATCCAAATGGCTGCT
TTTGTCTCCCTTACCTCGTGAAGAGGGGAAGTCTCTTCCTGCCTCCCAAGCAGCTGAAG
GGTGACTAAACGGGCGCCAAGACTCAGGGGATCGGCTGGGAACTGGGCCAGCAGAGCAT
GTTGGACACCCCCACCATGGTGGGCTTGTGGTGGCTGCTCCATGAGGGTGGGGGTGAT
ACTACTAGATCACTTGTCCTCTTGCCAGCTCATTTGTTAATAAAATACTGAAAACACAA
AAAAAAAAAAAAAAAAAAAAAAAAAAAAAAAAAAAAAAAAAAAAAAAAAAAAAAAAAAA
AAAAAAAAAAAAA (SEQ ID NO:25)
```

FIG. 5

```
HASDLLKNDYFSAEDAEIVCACPTQPDKVRKILDLVQSKGEEVSEFFLYLL
QQLADAYVDLRPWLLEIGFSPSLLTQSKVVVVNTDPVSRYTQQLRHHLGRDS
KFVLCYAQKEELLLEEIYMDTIMELVGFSNESLGSLNSLACLLDHTTGILN
EQGETIFILGDAGVGKSMLLQRLQSLWATGRLDAGVKFFFHFRCRMFSCFK
ESDRLCLQDLLFKHYCYPERDPEEVFAFLLRFPHVALFTFDGLDELHSDLD
LSRVPDSSCPWEPAHPLVLLANLLSGKLLKGASKLLTARTGIEVPRQFLRK
KVLLRGFSPSHLRAYARRMFPERALQDRLLSQLEANPNLCSLCSVPLFCWI
IFRCFQHFRAAFEGSPQLPDCTMTLTDVFLLVTEVHLNRMQPSSLVQRNTR
SPVETLHAGRDTLCSLGQVAHRGMEKSLFVFTQEEVQASGLQERDMQLGFL
RALPELGPGGDQQSYEFFHLSLLTCKTGIPV    (SEQ ID NO:26)
```

```
CCCGCGTCCGCGTCCCCGGACCATGGCGCTCTCCGGGCTCTTCTCTAGCTCTCAGCGGCT
GCGAAGTCTGTNAACCTGGTGGCCAAGTGATTGTAAGTCAGGAGACTTTCCTTCGGTTTC
TGCCTTTGATGGCAAGAGGTGGAGATTGTGGCGGCGATTACAGAAAACATCTGGGAAGAC
AAGTTGCTGTTTTTATGGGAATCGCAGGCTTGGAAGAGACAGAAGCAATTCCAGAAATAA
ATTGGAAATTGAAGATTTAAACAATGTTGTTTTAAAATATTCTAACTTCAAAGAATGATG
CCAGAAACTTAAAAAGGGGCTGCGCAGAGTAGCAGGGGCCCTGGAGGGCGCGGCCTGAAT
CCTGATTGCCCTTCTGCTGAGAGGACACACGCAGCTGAAGATGAATTTGGGAAAAGTAGC
CGCTTGCTACTTTAACTATGGAAGAGCAGGGCCACAGTGAGATGGAAATAATCCCATCAG
AGTCTCACCCCACATTCAATTACTGAAAAGCAATCGGGAACTTCTGGTCACTCACATCC
GCAATACTCAGTGTCTGGTGGACAACTTGCTGAAGAATGACTACTTCTCGGCCGAAGATG
CGGAGATTGTGTGTGCCTGCCCCACCCAGCCTGACAAGGTCCGCAAAATTCTGGACCTGG
TACAGAGCAAGGGCGAGGAGGTGTCCGAGTTCTTCCTCTACTTGCTCCAGCAACTCGCAG
ATGCCTACGTGGACCTCAGGCCTTGGCTGCTGGAGATCGGCTTCTCCCCTTCCCTGCTCA
CTCAGAGCAAAGTCGTGGTCAACACTGACCCAGTGAGCAGGTATACCCAGCAGCTGCGAC
ACCATCTGGGCCGTGACTCCAAGTTCGTGCTGTGCTATGCCCAGAAGGAGGAGCTGCTGC
TGGAGGAGATCTACATGGACACCATCATGGAGCTGGTTGGCTTCAGCAATGAGAGCCTGG
GCAGCCTGAACAGCCTGGCCTGCCTCCTGGACCACACCACCGGCATCCTCAATGAGCAGG
CTGCTTCAAGGAAAGTGACAGGCTGTGTCTGCAGGACCTGCTCTTCAAGCACTACTGCTA
CCCAGAGCGGGACCCCGAGGAGGTGTTTGCCTTCCTGCTGCGCTTCCCCCACGTGGCCCT
CTTCACCTTCGATGGCCTGGACGAGCTGCACTCGGACTTGGACCTGAGCCGCGTGCCTGA
CAGCTCCTGCCCCTGGGAGCCTGCCCACCCCTGGTCTTGCTGGCCAACCTGCTCAGTGG
GAAGCTGCTCAAGGGGGCTAGCAAGCTGCTCACAGCCCGCACAGGCATCGAGGTCCCGCG
CCAGTTCCTGCGGAAGAAGGTGCTTCTCCGGGCTTCTCCCCAGCCACCTGCGCGCCTA
TGCCAGGAGGATGTTCCCCGAGCGGGCCCTGCAGGACCGCCTGCTGAGCCAGCTGGAGGC
CAACCCCAACCTCTGCAGCCTGTGCTCTGTGCCCCTCTTCTGCTGGATCATCTTCCGGTG
CTTCCAGCACTTCCGTGCTGCCTTTGAAGGCTCACCACAGCTGCCCGACTGCACGATGAC
CCTGACAGATGTCTTCCTCCTGGTCACTGAGGTCCATCTGAACAGGATGCAGCCCAGCAG
CCTGGTGCAGCGGAACACACGCAGCCCAGTGGAGACCCTCCACGCCGGCCGGGACACTCT
GTGCTCGCTGGGGCAGGTGGCCCACCGGGGCATGGAGAAGAGCCTCTTTGTCTTCACCCA
GGAGGAGGTGCAGGCCTCCGGGCTGCAGGAGAGAGACATGCAGCTGGGCTTCCTGCGGGC
TTTGCCGGAGCTGGGCCCCGGGGGTGACCAGCAGTCCTATGAGTTTTTCCACCTCACCCT
```

FIG. 10A

```
CCAGGCCTTCTTTACAGCCTTCTTCCTCGTGCTGGACGACAGGGTGGGCACTCAGGAGCT
GCTCAGGTTCTTCCAGGAGTGGATGCCCCCTGCGGGGGCAGCGACCACGTCCTGCTATCC
TCCCTTCCTCCCGTTCCAGTGCCTGCAGGGCAGTGGTCCGGCGCGGGAAGACCTCTTCAA
GAACAAGGATCACTTCCAGTTCACCAACCTCTTCCTGTGCGGGCTGTTGKCCAAAGCCAA
ACAGAAACTCCTGCGGCATCTGGTGCCCGCGGCAGCCCTGAGGAGAAAGCGCAAGGCCCT
GTGGGCACACCTGTTTTCCAGCCTGCGGGGCTACCTGAAGAGCCTGCCCCGCGTTCAGGT
CGAAAGCTTCAACCAGGTGCAGGCCATGCCCACGTTCATCTGGATGCTGCGCTGCATCTA
CGAGACACAGAGCCAGAAGGTGGGGCAGCTGGCGGCCAGGGGCATCTGCGCCAACTACCT
CAAGCTGACCTACTGCAACGCCTGCTCGGCCGACTGCAGCGCCCTCTCCTTCGTCCTGCA
TCACTTCCCCAAGCGGCTGGCCCTAGACCTAGACAACAACAATCTCAACGACTACGGCGT
GCGGGAGCTGCAGCCCTGCTTCAGCCGCCTCACTGTTCTCAGACTCAGCGTAAACCAGAT
CACTGACGGTGGGGTAAAGGTGCTAAGCGAAGAGCTGACCAAATACAAAATTGTGACCTA
TTTGGGTTTATACAACAACCAGATCACCGATGTCGGAGCCAGGTACGTCACCAAAATCCT
GGATGAATGCAAAGGCCTCACGCATCTTAAACTGGGAAAAAACAAAATAACAAGTGAAGG
AGGGAAGTATCTCGCCCTGGCTGTGAAGAACAGCAAATCAATCTCTGAGGTTGGGATGTG
GGGCAATCAAGTTGGGGATGAAGGAGCAAAAGCCTTCGCAGAGGCTCTGCGGAACCACCC
CAGCTTGACCACCCTGAGTCTTGCGTCCAACGGCATCTCCACAGAAGGAGGAAAGAGCCT
TGCGAGGGCCCTGCAGCAGAACACGTCTCTAGAAATACTGTGGCTGACCCAAAATGAACT
CAACGATGAAGTGGCAGAGAGTTTGGCAGAAATGTTGAAAGTCAACCAGACGTTAAAGCA
TTTATGGCTTATCCAGAATCASATCACAGCTWARGGGACTGCCCAGCTGGCAGATGCGTT
ACAGAGCAACACTGGCATAACAGAGATTTGCCTAAATGGAAACCTGATAAAACCAGAGGA
GGCCAAAGTCTATGAAGATGAGAAGCGGATTATCTGTTTCTGAGAGGATGCTTTCCTGTT
CATGGGGTTTTTGCCCTGGAGCCTCAGCAGCAAATGCCACTYTGGGCAGTCTTTTGTGTC
AGTGTCTTAAAGGGGCCTGCGCAGGCGGGACTATCAGGAGTCCACTGCCTCCATGATGCA
AGCCAGCTTCCTGTGCAGAAGGTCTGGTCGGCAAACTCCCTAAGTACCCGCTACAATTCT
GCAGAAAAGAATGTGTCTTGCGAGCTGTTGTAGTTACAGTAAATACACTGTGAAGAGAC
TTTATTGCCTATTATAATTATTTTTATCTGAAGCTAGAGGAATAAAGCTGTGAGCAAACA
GAGGAGGCCAGCCTCACCTCATTCCAACACCTGCCATAGGGACCAACGGGAGCGAGTTGG
TCACCGCTCTTTTCATTGAAGAGTTGAGGATGTGGCACAAAGTTGGTGCCAAGCTTCTTG
AATAAAACGTGTTTGATGGATTAGTATTATACCTGAAATATTTTCTTCCTTCTCAGCACT
TTCCCATGTATTGATACTGGTCCCACTTCACAGCTGGAGACACCGGAGTATGTGCAGTGT
GGGATTTGACTCCTCCAAGGTTTTGTGGAAAGTTAATGTCAAGGAAAGGATGCACCACGG
```

FIG. 10B

GCTTTTAATTTTAATCCTGGAGTCTCACTGTCTGCTGGCAAAGATAGAGAATGCCCTCAG
CTCTTAGCTGGTCTAAGAATGACGATGCCTTCAAAATGCTGCTTCCACTCAGGGCTTCTC
CTCTGCTAGGCTACCCTCCTCTAGAAGGCTGAGTACCATGGGCTACAGTGTCTGGCCTTG
GGAAGAAGTGATTCTGTCCCTCCAAAGAAATAGGGCATGGCTTGCCCCTGTGGCCCTGGC
ATCCAAATGGCTGCTTTTGTCTCCCTTACCTCGTGAAGAGGGGAAGTCTCTTCCTGCCTC
CCAAGCAGCTGAAGGGTGACTAAACGGGCGCCAAGACTCAGGGGATCGGCTGGGAACTGG
GCCAGCAGAGCATGTTGGACACCCCCACCATGGTGGGCTTGTGGTGGCTGCTCCATGAG
GGTGGGGGTGATACTACTAGATCACTTGTCCTCTTGCCAGCTCATTTGTTAATAAAATAC
TGAAAACCCAAAAAAAAAAAAAAAAAAAAAAAAAAGGGCGG (SEQ ID NO:39)

FIG. 10C

MEEQGHSEMEIIPSESHPHIQLLKSNRELLVTHIRNTQCLVDNLLKNDYFSAEDAEIVCA
CPTQPDKVRKILDLVQSKGEEVSEFFLYLLQQLADAYVDLRPWLLEIGFSPSLLTQSKVV
VNTDPVSRYTQQLRHHLGRDSKFVLCYAQKEELLLEEIYMDTIMELVGFSNESLGSLNSL
ACLLDHTTGILNEQAASRKVTGCVCRTCSSSTTATQSGTPRRCLPSCCASPTWPSSPSMA
WTSCTRTWT (SEQ ID NO:40)

FIG. 11

CACGCGTCCGCGCTACTGCGGGAGCAGCGTCCTCCCGGGCCACGGCGCTTCCCGGCCCCG
GCGTCCCCGGACCATGGCGCTCTCCGGGCTCTTCTCTAGCTCTCAGCGGCTGCGAAGTCT
GTAAACCTGGTGGCCAAGTGATTGTAAGTCAGGAGACTTTCCTTCGGTTTCTGCCTTTGA
TGGCAAGAGGTGGAGATTGTGGCGGCGATTACAGAAACATCTGGGAAGACAAGTTGCTG
TTTTTATGGAATCGCAGGCTTGGAAGAGACAGAAGCAATTCCAGAAATAAATTGGAAAT
TGAAGATTTAAACAATGTTGTTTTAAAATATTCTAACTTCAAAGAATGATGCCAGAAACT
TAAAAAGGGGCTGCGCAGAGTAGCAGGGGCCCTGGAGGGCGCGGCCTGAATCCTGATTGC
CCTTCTGCTGAGAGGACACACGCAGCTGAAGATGAATTTGGGAAAAGTAGCCGCTTGCTA
CTTTAACTATGGAAGAGCAGGGCCACAGTGAGATGGAAATAATCCCATCAGAGTCTCACC
CCCACATTCAATTACTGAAAAGCAATCGGGAACTTCTGGTCACTCACATCCGCAATACTC
AGTGTCTGGTGGACAACTTGCTGAAGAATGACTACTTCTCGGCCGAAGATGCGGAGATTG
TGTGTGCCTGCCCCACCCAGCCTGACAAGGTCCGCAAAATTCTGGACCTGGTACAGAGCA
AGGGCGAGGAGGTGTCCGAGTTCTTCCTCTACTTGCTCCAGCAACTCGCAGATGCCTACG
TGGACCTCAGGCCTTGGCTGCTGGAGATCGGCTTCTCCCCTTCCCTGCTCACTCAGAGCA
AAGTCGTGGTCAACACTGACCCAGGTAGGAGTCAGCCCCAGCAAGACCGCAGGCACCAGT
GCAAGCAGGGCCCTGGGGGGTTTGGTAATGGCTGGGCCAGCCCTGAGTGCCACCTCAGGA
AGCAGGCCCAGGTGCTATTTTGATTTTAGAAAGGAACAGCTGAATCCTGTCTCCCAAGTG
CAGCCCAGGTGGCTGCGATTGAACTGCCCACACCTCGATGGTCTGGTTTATAGAGGGGCC
TTTGGAAGTATGGGAATGGCCTGTGTTCTGACCCCTTGCTTTCTTCCTATTCTGACATAT
GTAGACATTTTAATGGTTGCACAAATTCAAGGTTGTATTTTTTTTCTTTAAAAAAATCT
TTAGCTGGACATGGTAGCACACACCTGTAGTTCCAGCTACTCAGGAGGCTGAGGCAAGAG
GACTGCTTGAGCCCCAGAGTCTAAGGCTGCAGCGAGCTATGATTGTGCCCCTACACTCCA
CAGCCTGGGTTTTAGAGTGAGACCCTGTCTCTAAAAAAAAAAAAAAAAAAAAAAAAAA
AAAAAAAAAAAAANGGGCGG (SEQ ID NO:41)

FIG. 12

MEEQGHSEMEIIPSESHPHIQLLKSNRELLVTHIRNTQCLVDNLLKNDYFSAEDAEIVCA
CPTQPDKVRKILDLVQSKGEEVSEFFLYLLQQLADAYVDLRPWLLEIGFSPSLLTQSKVV
VNTDPGRSQPQQDRRHQCKQGPGGFGNGWASPECHLRKQAQVLF
(SEQ ID NO:42)

FIG. 13

```
                  D T I M E L V G F S N E S L G S L N S L A C L L D H T T G I L N E Q X X X X - -  Majority
                                  170                 180                 190                 200
161               D T I M E L V G F S N E S L G S L N S L A C L L D H T T G I L N E Q A A S R - -  CARD4-Y CLONE
137               - - - - - - - - - - - - - - - - - - - - - - - - - - - - - - - - - - - - - -    CARD4-Z CLONE
161               D T I M E L V G F S N E S L G S L N S L A C L L D H T T G I L N E Q G E T I F I  CARD4L

- - - - - - - - - - X C K X X X - - - - - - - - - - - - - - - - - - - - - - -  Majority
                          210                 220                 230                 240
199               - - - - - - - - - - - - - - - - - - - - - - - - - - - - - - K V T G             CARD4-Y CLONE
137               - - - - - - - - - - - - - - - - - - - - - - - - - - - - - - Q C K Q - -         CARD4-Z CLONE
201               L G D A G V G K S M L L Q R L Q S L W A T G R L D A G V K F F F H F R C R M F S  CARD4L C - - - - - X C - - - - - - V C - - - - - - - - - - - X X C X X X - - - - - -    Majority
                      250                 260                 270                 280
203               C - - - - - - - - - - - - - V C - - - - - - - - - - - - - - - - - - - - - -     CARD4-Y CLONE
141               - - - - - - - - - - - - - - - - - - - - - - - - - - - - - - - - - - - - - -    CARD4-Z CLONE
241               C F K E S D R L C L Q D L L F K H Y C Y P E R D P E E V F A F L L R F P H V A L  CARD4L

- - - - - - - - - - - - - - - - - - - - - R T C S S S - - - - - - - - - - - -  Majority
                          290                 300                 310                 320
206               - - - - - - - - - - - - - - - - - - - - - - - - S - - - - - - - - - - - - -    CARD4-Y CLONE
141               - - - - - - - - - - - - - - - - - - - - - - - - S - - - - - - - - - - - - -    CARD4-Z CLONE
281               F T F D G L D E L H S D L D L S R V P D S S C P W E P A H P L V L L A N L L S G  CARD4L
```

FIG. 14B

|       | X X X X F | Majority |
|-------|-----------|----------|
| 249   |           |          |
| 164   | - - - F   | CARD4-Y CLONE |
| 164   | - - - F   | CARD4-Z CLONE |
| 961   | R I I C F | CARD4L   |

Decoration 'Decoration #1': Shade (with solid black) residues that match the Consensus exactly.

FIG. 14G

```
CCACGCGTCCGCGGACCGCGAGCGGTAGCGCCCTCCCTCCCAGCTGTTGTCCCGCCCGAT
CCGCGACCCTAGTCCCCGGATCCCCTTGCTGAGAGTCACCGTACTCCAGGGCCAACTGAG
CCAAAGTCCTGCCAACTTGGGTCAGCAATGAAAGGCAGGATCCTGGGTGGTGGCCCTGAA
TCCTGATTTGTCTGCCCTGCCAGCGAGACACATGTGGTCAAAGATGAATTTGAGAAAAGT
AGCTGCTGGCTACTTGAACAATGGAGGAACACGGCCATCATGAGATGGAAGGCACCCAT
TGGGTTGTCACTCCCACATTAAACTGCTGAAGATCAACAGGGAACATCTGGTCACCAACA
TTCGGAACACTCAGTGTCTGGTGGACAACTTGCTGGAGAATGGCTACTTCTCAGCCGAAG
ATGCAGAGATTGTGTGTGCCTGTCCCACCAAGCCTGACAAGGTCCGAAAGATCCTTGACC
TGGTGCAGAGCAAAGGCGAGGAGTGTCTGAGTTCTTCCTCTACGTGCTGCAGCAGCTGG
AGGATGCTTACGTGGACCTCAGGCTGTGGCTCTCAGAAATTGGCTTCTCCCCTTCCCAGC
TCATTCGGACCAAAACTATCGTCAATACTGACCCAGTAAGCAGGTATACCCAACAGCTGC
GACACCAACTGGGCCGCGACTCCAAGTTCATGCTGTGCTACGCCCAGAAGGAGGACCTGC
TGCTGGAGGAGACCTATATGGACACACTCATGGGGCTGGTAGGCTTCAACAATGAAAACC
TGGGCAGCCTAGGAGGCCTGGATTGCCTGCTGGACCACAGTACGGGCGTCCTCAACGAGC
ATGGCGAGACTGTCTTCGTGTTCGGGGACGCGGGAGTGGGCAAGTCCATGCTGCTGCAGA
GGTTGCAGAGCCTCTGGGCGTCAGGCAGGTTGACCTCCACAGCCAAATTCTTCTTCCACT
TCCGCTGCCGCATGTTCAGCTGCTTCAAGGAGAGCGACATGCTGAGTCTGCAGGACCTGC
TCTTCAAGCATTTCTGCTACCCGGAGCAGGACCCCGAGGAGGTGTTCTCCTTCTTGCTGC
GCTTTCCCCACACAGCGCTCTTCACTTTTGACGGCCTGGATGAGCTGCACTCAGACTTCG
ACCTGAGCCGCGTGCCGGATAGCTGCTGCCCCTGGGAGCCGGCTCACCCTCTGGTCCTGC
TGGCTAACCTCCTAAGTGGGAGGCTGCTCAAGGGTGCCGGCAAATTGCTCACTGCTCGCA
CAGGCGTGGAGGTCCCCCGCCAGCTCCTGCGCAAAAAGGTGCTGCTCCGGGGCTTCTCCC
CAAGTCACCTGCGCGCCTATGCCCGCCGGATGTTCCCCGAGCGCACAGCGCAGGAGCATC
TGCTGCAGCAGCTGGATGCCAACCCCAACCTCTGCAGCCTGTGCGGGGTGCCGCTCTTCT
GTTGGATCATCTTCCGTTGTTTCCAGCACTTCCAGACGGTCTTCGAGGGCTCCTCTTCAC
AGTTGCCGGACTGTGCTGTGACCCTGACCGATGTCTTTCTGCTGGTCACTGAGGTGCATC
TGAACAGGCCGCAGCCCAGCAGCCTGGTGCAGCGCAACACGCGCAGCCCGGCGGAAACCC
TACGTGCAGGCTGGCGCACGCTGCATGCGCTGGGAGAGGTGGCTCACCGAGGCACCGACA
AGAGCCTCTTTGTGTTTGGCCAGGAGGAGGTGCAGGCGTCGAAGCTGCAGGAAGGAGATC
TGCAGCTGGGCTTCCTGCGGGCTTTGCCCGATGTGGGCCCTGAGCAGGGCCAGTCTTACG
AATTTTTCCACCTTACGCTCCAGGCCTTCTTCACCGCCTTCTTCCTGGTAGCAGATGACA
AAGTGAGCACCCGGGAGTTGCTGAGGTTCTTTCGAGAATGGACGTCTCCTGGAGAGGCAA
```

FIG. 15A

```
CAAGCTCGTCCTGCCATTCTTCCTTCTTCTCCTTCCAGTGCCTGGGCGGCAGAAGCCGGT
TGGGCCCTGATCCTTTCAGGAACAAAGATCACTTCCAGTTCACCAACCTCTTCGTGTGCG
GGCTACTGGCCAAAGCCCGACAGAAACTCCTTCGGCAGCTGGTGCCCAAGGCTATCCTGA
GGAGGAAGCGCAAGGCCCTGTGGGCTCACCTGTTTGCTAGCCTGCGCTCCTACTTGAAGA
GCCTACCTCGGGTCCAGTCTGGAGGCTTTAACCAGGTGCATGCCATGCCCACATTCCTGT
GGATGCTGCGCTGCATCTATGAGACGCAGAGCCAGAAGGTGGGGCGCCTCGCCGCCAGGG
GCATCAGTGCGGACTACCTCAAGCTGGCCTTTTGCAACGCTTGCTCTGCGGACTGCAGCG
CCCTGTCCTTCGTCCTGCATCACTTCCACAGGCAGCTGGCCCTAGACCTGGACAACAACA
ACCTCAATGACTATGGCGTGCAGGAGCTGCAGCCTTGCTTTAGCCGTCTCACGGTTATCA
GACTCAGCGTCAACCAGATCACCGACACGGGGGTGAAGGTGCTATGTGAGGAACTGACCA
AGTATAAGATCGTGACGTTCCTGGGTTTATACAACAACCAGATAACTGATATCGGAGCCA
GGTATGTGGCCCAAATCCTGGATGAATGCAGAGGCCTCAAGCACCTTAAACTAGGGAAAA
ACAGAATAACAAGTGAGGGCGGGAAGTGTGTGGCTTTGGCTGTGAAGAACAGCACCTCCA
TCGTTGATGTTGGGATGTGGGGTAATCAGATTGGAGACGAAGGGGCAAAGGCCTTCGCAG
AGGCATTGAAGGACCACCCCAGCCTGACCACTCTCAGTCTTGCATTCAATGGCATCTCTC
CGGAGGGAGGGAAGAGCCTTGCGCAGGCCCTGAAGCAGAACACCACACTGACAGTAATCT
GGCTGACCAAAAATGAACTTAATGATGAGTCTGCAGAGTGCTTCGCTGAGATGCTGAGAG
TGAACCAGACGCTACGGCATTTATGGCTGATCCAGAATCGCATCACAGCCAAGGGGACAG
CGCAGCTGGCGAGGGCACTGCAGAAGAACACAGCCATAACAGAGATTTGTCTCAATGGAA
ACTTGATTAAGCCCGAGGAGGCCAAAGTCTTCGAGAATGAGAAGAGAATCATCTGCTTCT
GACGGACGCTCCTGGGCAGGATCTTTGTCCTAGGTTGCTCCTCAGTCACAGACAGCACTG
TGCAGTCAGCAGGGTAGCAGGATGCTGTGCAGCGCCTGCAGCAAGGTGCCTGTCAGGAGC
CCACACCTCCACAGTGCACACCGATGTCCCTGCTCATGCTTGGACTGGTAGCACCCGCG
CCGCGGCTGAGACCCTGCAGACGCAGGGAGTCTTAGGAACCATCGTCACCACTCAAAGCC
AGCAGGGCATCTTCTGTACAAAGATCTCCCTGCATATCCACTAGACGGAAGCTGAAGGAA
CGCAACAGCAGAGGAGGCCAACAGACGCCTGGCTGAAGGCTCCGTGGGACCAACGGTGTC
ACCTTCAGAAAAGAGCTGGGAACTTGAGCAGAGCCGATGGTAACTTCTTGGGGAAAGAAG
GCACCCAGTGACTGCATGGTTATTCTGAGTCCTCCTTCCTCTGCTTAGTCCCTCTCACTG
TACAGGTCTGTTTCTTCCTCGCAGCTGTGGCTGCTGAAGTAGGTCCACTGTGGGGAGAGC
TCATCACAGACTTTGGTTCGGTTCTGGATTCTCAGTGGTGGCAACCGAGAGTCAGACGAT
ACCCTCTAGGTCAGTCTCAGAGGATCTCTATGCTGTGAGAGGGTTGAGGGCCCACCCAGA
ATTTTTTTTTTTTACCAGTTTTTACTGTGCCTGCCCCAGGAGGGAGAATTACTTCCCAGC
```

FIG. 15B

CTCCACAGCAGCAGGCATGGCTTGCCTCAATGGTCCTGAGATCCCAACAAAACTCTCTCC
CTTGCCTGTGAGCAGAAAGTATCTTCATGTCCTCAGAAGTTGGAGGGTGACTGGACACAG
TTAAGACTCAGAGAGCCAGCTGATAGCTCAAAGCAAAGCATGGCACATACCCACCACCAT
ACCATGGTGCGCATGGGATGGGACAGTTGGAATGTTGCAGATAACGTGTTCTTTTGCCAG
TTCATTTGTTAATAAAATATTTAAAACGTTAAAAAAAAAAAAAAAAAAAAAAAAGGGCG
G (SEQ ID NO:43)

FIG. 15C

MEEHGHHEMEGTPLGCHSHIKLLKINREHLVTNIRNTQCLVDNLLENGYFSAEDAEIVCA
CPTKPDKVRKILDLVQSKGEEVSEFFLYVLQQLEDAYVDLRLWLSEIGFSPSQLIRTKTI
VNTDPVSRYTQQLRHQLGRDSKFMLCYAQKEDLLLEETYMDTLMGLVGFNNENLGSLGGL
DCLLDHSTGVLNEHGETVFVFGDAGVGKSMLLQRLQSLWASGRLTSTAKFFFHFRCRMFS
CFKESDMLSLQDLLFKHFCYPEQDPEEVFSFLLRFPHTALFTFDGLDELHSDFDLSRVPD
SCCPWEPAHPLVLLANLLSGRLLKGAGKLLTARTGVEVPRQLLRKKVLLRGFSPSHLRAY
ARRMFPERTAQEHLLQQLDANPNLCSLCGVPLFCWIIFRCFQHFQTVFEGSSSQLPDCAV
TLTDVFLLVTEVHLNRPQPSSLVQRNTRSPAETLRAGWRTLHALGEVAHRGTDKSLFVFG
QEEVQASKLQEGDLQLGFLRALPDVGPEQGQSYEFFHLTLQAFFTAFFLVADDKVSTREL
LRFFREWTSPGEATSSSCHSSFFSFQCLGGRSRLGPDPFRNKDHFQFTNLFVCGLLAKAR
QKLLRQLVPKAILRRKRKALWAHLFASLRSYLKSLPRVQSGGFNQVHAMPTFLWMLRCIY
ETQSQKVGRLAARGISADYLKLAFCNACSADCSALSFVLHHFHRQLALDLDNNNLNDYGV
QELQPCFSRLTVIRLSVNQITDTGVKVLCEELTKYKIVTFLGLYNNQITDIGARYVAQIL
DECRGLKHLKLGKNRITSEGGKCVALAVKNSTSIVDVGMWGNQIGDEGAKAFAEALKDHP
SLTTLSLAFNGISPEGGKSLAQALKQNTTLTVIWLTKNELNDESAECFAEMLRVNQTLRH
LWLIQNRITAKGTAQLARALQKNTAITEICLNGNLIKPEEAKVFENEKRIICF
(SEQ ID NO:44)

FIG. 16

```
mCARD4Lpep.PRO             MEEQGHSEMEGIPLGSHSHIQLLKINRELLVTNIRNTQCLVDNLLENGYFSAEDAEIVCACPTQPDKVRKILDLVQSKGEEVSEFFLYVL
                                    10        20        30        40        50        60        70        80
mCARD4Lpep.PRO             MEEHGHHEMEGTPLGCHSHIKLLKINREHLVTNIRNTQCLVDNLLENGYFSAEDAEIVCACPTKPDKVRKILDLVQSKGEEVSEFFLYVL  90
hCARD4Lpep.PRO             MEEQSHEMEIIPSESHPHIQLLKSNRELLVTHIRNTQCLVDNLLKNDYFSAEDAEIVCACPTQPDKVRKILDLVQSKGEEVSEFFLYLL  90 mCARD4Lpep.PRO             QQLADAYVDLRLWLLEIGFSPSLLIQSKVVVNTDPVSRYTQQLRHQLGRDSKFVLCYAQKEDLLEEIYMDTLMGLVGFSNESLGSLGGL
                                   100       110       120       130       140       150       160       170
mCARD4Lpep.PRO             QQLEDAYVDLRLWLSEIGFSPSQLIRTKTIVNTDPVSRYTQQLRHQLGRDSKFMLCYAQKEDLLEEIYMDTLMGLVGFNNENLGSLGGL 180
hCARD4Lpep.PRO             QQLADAYVDLRPWLLEIGFSPSLLTQSKVVVNTDPVSRYTQQLRHHLGRDSKFVLCYAQKEELLLEEIYMDTIMELVGFSNESLGSLNSL 180 mCARD4Lpep.PRO             ACLLDHSTGVLNEQGETVFVLGDAGVGKSMLLQRLQSIMASGRLTAGAKFFFHFRCRMFSCFKESDRLSLQDLLFKHFCYPEQDPEEVFA
                                   190       200       210       220       230       240       250       260
mCARD4Lpep.PRO             DCLLDHSTGVLNEHGETVFVFGDAGVGKSMLLQRLQSIMASGRLTSTAKFFFHFRCRMFSCFKESDMLSLQDLLFKHFCYPEQDPEEVFS 270
hCARD4Lpep.PRO             ACLLDHTTGILNEQGETIFILGDAGVGKFFFHFRCRMFSCFKESDRLCLQDLLFKHYCYPERDPEEVFA 270 mCARD4Lpep.PRO             FLLRPHVALFTFDGLDELHSDLDLSRVPDSSCPWEPAHPLVLLANLLSGKLLKGAGKLLTARTGVEVPRQLLRKKVLLRGFSPSHLRAY
                                   280       290       300       310       320       330       340       350
mCARD4Lpep.PRO             FLLRFPHTALFTFDGLDELHSDFDLSRVPDSSCCPWEPAHPLVLLANLLSGRLLKGAGKLLTARTGVEVPRQLLRKKVLLRGFSPSHLRAY 360
hCARD4Lpep.PRO             FLLRFPHVALFTFDGLDELHSDLDLSRVPDSSCPWEPAHPLVLLANLLSGKLLKGASKLLTARTGIEVPRQFLRKKVLLRGFSPSHLRAY 360 mCARD4Lpep.PRO             ARRMFPERAAQDHLLSQLDANPNLCSLCGVPLFCWIIFRCFQHFQAAFEGSSSQLPDCAVTLTDVFLLVTEVHLNRMQPSSLVQRNTRSP
                                   370       380       390       400       410       420       430       440
mCARD4Lpep.PRO             ARRMFPERTAQEHLLQQLDANPNLCSLCGVPLFCWIIFRCFQHFQTVFEGSSSQLPDCAVTLTDVFLLVTEVHLNRPQPSSLVQRNTRSP 450
hCARD4Lpep.PRO             ARRMFPERALQDRLLSQLEANPNLCSLCSVPLFCWIIFRCFQHFRAAFEGSP-QLPDCTMTLTDVFLLVTEVHLNRMQPSSLVQRNTRSP 449 mCARD4Lpep.PRO             AETLHAGRDTLHALGEVAHRGTDKSLFVFGQEEVQASGLQEGDLQLGFLRALPDVGPGGDGOSYEFFHLTLQAFFTAFFLVADDKVGTQE
                                   460       470       480       490       500       510       520       530
mCARD4Lpep.PRO             AETLRAGWRTLHALGEVAHRGTDKSLFVFGQEEVQASKLQEGDLQLGFLRALPDVGPE-QGQSYEFFHLTLQAFFTAFFLVADDKVSTRE 539
hCARD4Lpep.PRO             VETLHAGRDTLCSLGQVAHRGMEKSLFVFTQEEVQASGLQERDMQLGFLRALPELGPGGDQQSYEFFHLTLQAFFTAFFLVLDDRVGTQE 539
```

FIG. 17A

```
                                                                                       LLRFFQEWTSPGAASSSCHSSFLSFQCLGGSGRAGEDLFKNKDHFQFTNLFVCGLLAKAKQKLLROLVPAAALRRKRKALWAHLFASLR
mCARD4Lpep.PRO                                                                         LLRFFREWTSPGEATSSSCHSSFFSFQCLGGRSRLGPDPFRNKDHFQFTNLFVCGLLAKARQKLLRQLVPKAILRKRKALWAHLFASLR 629
hCARD4Lpep.PRO                                                                         LLRFFQEMPPAGAATTSCYPPFLPFQCLQGSPAREDLFKNKDHFQFTNLFLCGLLSKAKQKLLRHLVPAAALRRKRKALWAHLFSSLR 630
                                                                                               550       560       570       580       590       600       610       620

GYLKSLPRVQVGGFNQVQAMPTFLWMLRCIYETQSQKVGQLAARGISADYLKLAFCNACSADCSALSFVLHHFHKQLALDLDNNNLNDYG
mCARD4Lpep.PRO                                                                         SYLKSLPRVQSGGFNQVHAMPTFLWMLRCIYETQSQKVGRLAARGISADYLKLAFCNACSADCSALSFVLHHFHRQLALDLDNNNLNDYG 719
hCARD4Lpep.PRO                                                                         GYLKSLPRVQVESFNQVQAMPTFIWMLRCIYETQSQKVGQLAARGICANYLKLTYCNACSADCSALSFVLHHFPKRLALDLDNNNLNDYG 720
                                                                                               640       650       660       670       680       690       700       710

VQELQPCFSRLTVLRLSVNQITDGGVKVLSEELTKYKIVTFLGLYNNQITDVGARYVAQILDECKGLTHLSLYNNQITDVGAKLGKNKIT
mCARD4Lpep.PRO                                                                         VQELQPCFSRLTVIRLSVNQITDTGVKVLCEELTKYKIVTFLGLYNNQITDIGARYVAQILDECRGLKHL------KLGKNRIT 797
hCARD4Lpep.PRO                                                                         VRELQPCFSRLTVLRLSVNQITDGGVKVLSEELTKYKIVTYLGLYNNQITDVGARYVTKILDECKGLTHLSLYNNQITDVGARLGKNKIT 809
                                                                                               730       740       750       760       770       780       790       800

SEGGKYVALAVKNSTSIVDVGMMGNQVGDEGAKAFAEALKDHPSLTTLSLASNGISTEGGKSLAQALQQNTSLTVLMLTQNELNDEVAES
mCARD4Lpep.PRO                                                                         SEGGKCVALAVKNSTSIVDVGMMGNQIGDEGAKAFAEALKDHPSLTTLSLAFNGISPEGGKSLAQALKQNTTLTVIWLTKNELNDESAEC 887
hCARD4Lpep.PRO                                                                         SEGGKYLALAVKNSKSISEVGMWGNQVGDEGAKAFAEALRNHPSLTTLSLASNGISTEGGKSLARALQQNTSLEILMLTQNELNDEVAES 899
                                                                                               820       830       840       850       860       870       880       890

LAEMLKVNQTLKHLWLIQNQITAKGTAQLADALQSNTGITEICLNGNLIKPEEAKVFEDEKRIICF
mCARD4Lpep.PRO                                                                         FAEMLRVNQTLRHLWLIQNRITAKGTAQLARALQKNTAITEICLNGNLIKPEEAKVFENEKRIICF 953
hCARD4Lpep.PRO                                                                         LAEMLKVNQTLKHLWLIQNQITAKGTAQLADALQSNTGITEICLNGNLIKPEEAKVYEDEKRIICF 965
                                                                                               910       920       930       940       950       960
```

FIG. 17B

SEQUENCE LISTING

```
<160> NUMBER OF SEQ ID NOS: 47

<210> SEQ ID NO 1
<211> LENGTH: 1931
<212> TYPE: DNA
<213> ORGANISM: Homo sapiens
<220> FEATURE:
<221> NAME/KEY: CDS
<222> LOCATION: (214)...(1833)

<400> SEQUENCE: 1
ccacgcgtcc ggtcagctct ggttcggaga agcagcggct ggcgtgggcc atccggggaa      60
tgggcgccct cgtgacctag tgttgcgggg caaaaagggt cttgccggcc tcgctcgtgc     120
aggggcgtat ctgggcgcct gagcgcggcg tgggagcctt gggagccgcc gcagcagggg     180
gcacacccgg aaccggcctg agcgcccggg acc atg aac ggg gag gcc atc tgc     234
                                    Met Asn Gly Glu Ala Ile Cys
                                     1               5 agc gcc ctg ccc acc att ccc tac cac aaa ctc gcc gac ctg cgc tac     282
Ser Ala Leu Pro Thr Ile Pro Tyr His Lys Leu Ala Asp Leu Arg Tyr
         10                  15                  20 ctg agc cgc ggc gcc tct ggc act gtg tcg tcc gcc cgc cac gca gac     330
Leu Ser Arg Gly Ala Ser Gly Thr Val Ser Ser Ala Arg His Ala Asp
     25                  30                  35 tgg cgc gtc cag gtg gcc gtg aag cac ctg cac atc cac act ccg ctg     378
Trp Arg Val Gln Val Ala Val Lys His Leu His Ile His Thr Pro Leu
 40                  45                  50                  55 ctc gac agt gaa aga aag gat gtc tta aga gaa gct gaa att tta cac     426
Leu Asp Ser Glu Arg Lys Asp Val Leu Arg Glu Ala Glu Ile Leu His
                 60                  65                  70 aaa gct aga ttt agt tac att ctt cca att ttg gga att tgc aat gag     474
Lys Ala Arg Phe Ser Tyr Ile Leu Pro Ile Leu Gly Ile Cys Asn Glu
             75                  80                  85
```

```
cct gaa ttt ttg gga ata gtt act gaa tac atg cca aat gga tca tta    522
Pro Glu Phe Leu Gly Ile Val Thr Glu Tyr Met Pro Asn Gly Ser Leu
        90                  95                 100 aat gaa ctc cta cat agg aaa act gaa tat cct gat gtt gct tgg cca    570
Asn Glu Leu Leu His Arg Lys Thr Glu Tyr Pro Asp Val Ala Trp Pro
    105                 110                 115 ttg aga ttt cgc atc ctg cat gaa att gcc ctt ggt gta aat tac ctg    618
Leu Arg Phe Arg Ile Leu His Glu Ile Ala Leu Gly Val Asn Tyr Leu
120                 125                 130                 135 cac aat atg act cct cct tta ctt cat cat gac ttg aag act cag aat    666
His Asn Met Thr Pro Pro Leu Leu His His Asp Leu Lys Thr Gln Asn
                140                 145                 150 atc tta ttg gac aat gaa ttt cat gtt aag att gca gat ttt ggt tta    714
Ile Leu Leu Asp Asn Glu Phe His Val Lys Ile Ala Asp Phe Gly Leu
            155                 160                 165 tca aag tgg cgc atg atg tcc ctc tca cag tca cga agt agc aaa tct    762
Ser Lys Trp Arg Met Met Ser Leu Ser Gln Ser Arg Ser Ser Lys Ser
        170                 175                 180 gca cca gaa gga ggg aca att atc tat atg cca cct gaa aac tat gaa    810
Ala Pro Glu Gly Gly Thr Ile Ile Tyr Met Pro Pro Glu Asn Tyr Glu
185                 190                 195 cct gga caa aaa tca agg gcc agt atc aag cac gat ata tat agc tat    858
Pro Gly Gln Lys Ser Arg Ala Ser Ile Lys His Asp Ile Tyr Ser Tyr
200                 205                 210                 215 gca gtt atc aca tgg gaa gtg tta tcc aga aaa cag cct ttt gaa gat    906
Ala Val Ile Thr Trp Glu Val Leu Ser Arg Lys Gln Pro Phe Glu Asp
                220                 225                 230 gtc acc aat cct ttg cag ata atg tat agt gtg tca caa gga cat cga    954
Val Thr Asn Pro Leu Gln Ile Met Tyr Ser Val Ser Gln Gly His Arg
            235                 240                 245 cct gtt att aat gaa gaa agt ttg cca tat gat ata cct cac cga gca   1002
Pro Val Ile Asn Glu Glu Ser Leu Pro Tyr Asp Ile Pro His Arg Ala
        250                 255                 260 cgt atg atc tct cta ata gaa agt gga tgg gca caa aat cca gat gaa   1050
Arg Met Ile Ser Leu Ile Glu Ser Gly Trp Ala Gln Asn Pro Asp Glu
265                 270                 275 aga cca tct ttc tta aaa tgt tta ata gaa ctt gaa cca gtt ttg aga   1098
Arg Pro Ser Phe Leu Lys Cys Leu Ile Glu Leu Glu Pro Val Leu Arg
280                 285                 290                 295 aca ttt gaa gag ata act ttt ctt gaa gct gtt att cag cta aag aaa   1146
Thr Phe Glu Glu Ile Thr Phe Leu Glu Ala Val Ile Gln Leu Lys Lys
                300                 305                 310 aca aag tta cag agt gtt tca agt gcc att cac cta tgt gac aag aag   1194
Thr Lys Leu Gln Ser Val Ser Ser Ala Ile His Leu Cys Asp Lys Lys
            315                 320                 325 aaa atg gaa tta tct ctg aac ata cct gta aat cat ggt cca caa gag   1242
Lys Met Glu Leu Ser Leu Asn Ile Pro Val Asn His Gly Pro Gln Glu
        330                 335                 340 gaa tca tgt gga tcc tct cag ctc cat gaa aat agt ggt tct cct gaa   1290
Glu Ser Cys Gly Ser Ser Gln Leu His Glu Asn Ser Gly Ser Pro Glu
345                 350                 355 act tca agg tcc ctg cca gct cct caa gac aat gat ttt tta tct aga   1338
Thr Ser Arg Ser Leu Pro Ala Pro Gln Asp Asn Asp Phe Leu Ser Arg
360                 365                 370                 375 aaa gct caa gac tgt tat ttt atg aag ctg cat cac tgt cct gga aat   1386
Lys Ala Gln Asp Cys Tyr Phe Met Lys Leu His His Cys Pro Gly Asn
                380                 385                 390 cac agt tgg gat agc acc att tct gga tct caa agg gct gca ttc tgt   1434
His Ser Trp Asp Ser Thr Ile Ser Gly Ser Gln Arg Ala Ala Phe Cys
            395                 400                 405
```

```
gat cac aag acc att cca tgc tct tca gca ata ata aat cca ctc tca      1482
Asp His Lys Thr Ile Pro Cys Ser Ser Ala Ile Ile Asn Pro Leu Ser
        410                 415                 420 act gca gga aac tca gaa cgt ctg cag cct ggt ata gcc cag cag tgg      1530
Thr Ala Gly Asn Ser Glu Arg Leu Gln Pro Gly Ile Ala Gln Gln Trp
    425                 430                 435 atc cag agc aaa agg gaa gac att gtg aac caa atg aca gaa gcc tgc      1578
Ile Gln Ser Lys Arg Glu Asp Ile Val Asn Gln Met Thr Glu Ala Cys
440                 445                 450                 455 ctt aac cag tcg cta gat gcc ctt ctg tcc agg gac ttg atc atg aaa      1626
Leu Asn Gln Ser Leu Asp Ala Leu Leu Ser Arg Asp Leu Ile Met Lys
            460                 465                 470 gag gac tat gaa ctt gtt agt acc aag cct aca agg acc tca aaa gtc      1674
Glu Asp Tyr Glu Leu Val Ser Thr Lys Pro Thr Arg Thr Ser Lys Val
                475                 480                 485 aga caa tta cta gac act act gac atc caa gga gaa gaa ttt gcc aaa      1722
Arg Gln Leu Leu Asp Thr Thr Asp Ile Gln Gly Glu Glu Phe Ala Lys
        490                 495                 500 gtt ata gta caa aaa ttg aaa gat aac aaa caa atg ggt ctt cag cct      1770
Val Ile Val Gln Lys Leu Lys Asp Asn Lys Gln Met Gly Leu Gln Pro
    505                 510                 515 tac ccg gaa ata ctt gtg gtt tct aga tca cca tct tta aat tta ctt      1818
Tyr Pro Glu Ile Leu Val Val Ser Arg Ser Pro Ser Leu Asn Leu Leu
520                 525                 530                 535 caa aat aaa agc atg taagtgactg tttttcaaga agaaatgtgt ttcataaaag      1873
Gln Asn Lys Ser Met
                540 gatatttata aaaaaaaaaa aaaaaaaaaa aaaaaaaaaa aaaaaaaaaa aaaaaaa       1931

<210> SEQ ID NO 2
<211> LENGTH: 540
<212> TYPE: PRT
<213> ORGANISM: Homo sapiens

<400> SEQUENCE: 2

Met Asn Gly Glu Ala Ile Cys Ser Ala Leu Pro Thr Ile Pro Tyr His
 1               5                  10                  15

Lys Leu Ala Asp Leu Arg Tyr Leu Ser Arg Gly Ala Ser Gly Thr Val
                20                  25                  30

Ser Ser Ala Arg His Ala Asp Trp Arg Val Gln Val Ala Val Lys His
            35                  40                  45

Leu His Ile His Thr Pro Leu Leu Asp Ser Glu Arg Lys Asp Val Leu
        50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175
```

-continued

```
Gln Ser Arg Ser Ser Lys Ser Ala Pro Glu Gly Gly Thr Ile Ile Tyr
        180                 185                 190
Met Pro Pro Glu Asn Tyr Glu Pro Gly Gln Lys Ser Arg Ala Ser Ile
            195                 200                 205
Lys His Asp Ile Tyr Ser Tyr Ala Val Ile Thr Trp Glu Val Leu Ser
        210                 215                 220
Arg Lys Gln Pro Phe Glu Asp Val Thr Asn Pro Leu Gln Ile Met Tyr
225                 230                 235                 240
Ser Val Ser Gln Gly His Arg Pro Val Ile Asn Glu Glu Ser Leu Pro
                245                 250                 255
Tyr Asp Ile Pro His Arg Ala Arg Met Ile Ser Leu Ile Glu Ser Gly
            260                 265                 270
Trp Ala Gln Asn Pro Asp Glu Arg Pro Ser Phe Leu Lys Cys Leu Ile
        275                 280                 285
Glu Leu Glu Pro Val Leu Arg Thr Phe Glu Glu Ile Thr Phe Leu Glu
        290                 295                 300
Ala Val Ile Gln Leu Lys Lys Thr Lys Leu Gln Ser Val Ser Ser Ala
305                 310                 315                 320
Ile His Leu Cys Asp Lys Lys Met Glu Leu Ser Leu Asn Ile Pro
                325                 330                 335
Val Asn His Gly Pro Gln Glu Glu Ser Cys Gly Ser Ser Gln Leu His
            340                 345                 350
Glu Asn Ser Gly Ser Pro Glu Thr Ser Arg Ser Leu Pro Ala Pro Gln
        355                 360                 365
Asp Asn Asp Phe Leu Ser Arg Lys Ala Gln Asp Cys Tyr Phe Met Lys
370                 375                 380
Leu His His Cys Pro Gly Asn His Ser Trp Asp Ser Thr Ile Ser Gly
385                 390                 395                 400
Ser Gln Arg Ala Ala Phe Cys Asp His Lys Thr Ile Pro Cys Ser Ser
                405                 410                 415
Ala Ile Ile Asn Pro Leu Ser Thr Ala Gly Asn Ser Glu Arg Leu Gln
            420                 425                 430
Pro Gly Ile Ala Gln Gln Trp Ile Gln Ser Lys Arg Glu Asp Ile Val
        435                 440                 445
Asn Gln Met Thr Glu Ala Cys Leu Asn Gln Ser Leu Asp Ala Leu Leu
        450                 455                 460
Ser Arg Asp Leu Ile Met Lys Glu Asp Tyr Glu Leu Val Ser Thr Lys
465                 470                 475                 480
Pro Thr Arg Thr Ser Lys Val Arg Gln Leu Leu Asp Thr Thr Asp Ile
                485                 490                 495
Gln Gly Glu Glu Phe Ala Lys Val Ile Val Gln Lys Leu Lys Asp Asn
            500                 505                 510
Lys Gln Met Gly Leu Gln Pro Tyr Pro Glu Ile Leu Val Val Ser Arg
        515                 520                 525
Ser Pro Ser Leu Asn Leu Leu Gln Asn Lys Ser Met
        530                 535                 540
```

<210> SEQ ID NO 3
<211> LENGTH: 1620
<212> TYPE: DNA
<213> ORGANISM: Homo sapiens

<400> SEQUENCE: 3
atgaacgggg aggccatctg cagcgccctg cccaccattc cctaccacaa actcgccgac    60

-continued

```
ctgcgctacc tgagccgcgg cgcctctggc actgtgtcgt ccgcccgcca cgcagactgg      120
cgcgtccagg tggccgtgaa gcacctgcac atccacactc cgctgctcga cagtgaaaga      180
aaggatgtct taagagaagc tgaaatttta cacaaagcta gatttagtta cattcttcca      240
attttgggaa tttgcaatga gcctgaattt ttgggaatag ttactgaata catgccaaat      300
ggatcattaa atgaactcct acataggaaa actgaatatc ctgatgttgc ttggccattg      360
agatttcgca tcctgcatga aattgccctt ggtgtaaatt acctgcacaa tatgactcct      420
cctttacttc atcatgactt gaagactcag aatatcttat tggacaatga atttcatgtt      480
aagattgcag attttggttt atcaaagtgg cgcatgatgt ccctctcaca gtcacgaagt      540
agcaaatctg caccagaagg agggacaatt atctatatgc cacctgaaaa ctatgaacct      600
ggacaaaaat caagggccag tatcaagcac gatatatata gctatgcagt tatcacatgg      660
gaagtgttat ccagaaaaca gccttttgaa gatgtcacca atccttttgca gataatgtat      720
agtgtgtcac aaggacatcg acctgttatt aatgaagaaa gtttgccata tgatatacct      780
caccgagcac gtatgatctc tctaatagaa agtggatggg cacaaaatcc agatgaaaga      840
ccatctttct taaaatgttt aatagaactt gaaccagttt tgagaacatt tgaagagata      900
acttttcttg aagctgttat tcagctaaag aaaacaaagt tacagagtgt ttcaagtgcc      960
attcacctat gtgacaagaa gaaaatggaa ttatctctga acatacctgt aaatcatggt     1020
ccacaagagg aatcatgtgg atcctctcag ctccatgaaa atagtggttc tcctgaaact     1080
tcaaggtccc tgccagctcc tcaagacaat gatttttat ctagaaaagc tcaagactgt     1140
tattttatga agctgcatca ctgtcctgga atcacagtt gggatagcac catttctgga     1200
tctcaaaggg ctgcattctg tgatcacaag accattccat gctcttcagc aataataaat     1260
ccactctcaa ctgcaggaaa ctcagaacgt ctgcagcctg gtatagccca gcagtggatc     1320
cagagcaaaa gggaagacat tgtgaaccaa atgacagaag cctgccttaa ccagtcgcta     1380
gatgcccttc tgtccaggga cttgatcatg aaagaggact atgaacttgt tagtaccaag     1440
cctacaagga ccctcaaaagt cagacaatta ctagacacta ctgacatcca aggagaagaa     1500
tttgccaaag ttatagtaca aaaattgaaa gataacaaac aaatgggtct tcagccttac     1560
ccggaaatac ttgtggtttc tagatcacca tctttaaatt tacttcaaaa taaaagcatg     1620
```

<210> SEQ ID NO 4
<211> LENGTH: 300
<212> TYPE: PRT
<213> ORGANISM: Homo sapiens

<400> SEQUENCE: 4

Met Asn Gly Glu Ala Ile Cys Ser Ala Leu Pro Thr Ile Pro Tyr His
 1               5                  10                  15

Lys Leu Ala Asp Leu Arg Tyr Leu Ser Arg Gly Ala Ser Gly Thr Val
                20                  25                  30

Ser Ser Ala Arg His Ala Asp Trp Arg Val Gln Val Ala Val Lys His
            35                  40                  45

Leu His Ile His Thr Pro Leu Leu Asp Ser Glu Arg Lys Asp Val Leu
        50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

```
Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
        275                 280                 285

Glu Leu Glu Pro Val Leu Arg Thr Phe Glu Glu Ile
    290                 295                 300

<210> SEQ ID NO 5
<211> LENGTH: 131
<212> TYPE: PRT
<213> ORGANISM: Homo sapiens

<400> SEQUENCE: 5

Thr Phe Leu Glu Ala Val Ile Gln Leu Lys Lys Thr Lys Leu Gln Ser
  1               5                  10                  15

Val Ser Ser Ala Ile His Leu Cys Asp Lys Lys Met Glu Leu Ser
            20                  25                  30

Leu Asn Ile Pro Val Asn His Gly Pro Gln Glu Glu Ser Cys Gly Ser
            35                  40                  45

Ser Gln Leu His Glu Asn Ser Gly Ser Pro Glu Thr Ser Arg Ser Leu
    50                  55                  60

Pro Ala Pro Gln Asp Asn Asp Phe Leu Ser Arg Lys Ala Gln Asp Cys
65                  70                  75                  80

Tyr Phe Met Lys Leu His His Cys Pro Gly Asn His Ser Trp Asp Ser
                85                  90                  95

Thr Ile Ser Gly Ser Gln Arg Ala Ala Phe Cys Asp His Lys Thr Ile
            100                 105                 110

Pro Cys Ser Ser Ala Ile Ile Asn Pro Leu Ser Thr Ala Gly Asn Ser
        115                 120                 125

Glu Arg Leu
    130

<210> SEQ ID NO 6
<211> LENGTH: 110
<212> TYPE: PRT
<213> ORGANISM: Homo sapiens
```

-continued

```
<400> SEQUENCE: 6

Leu Gln Pro Gly Ile Ala Gln Gln Trp Ile Gln Ser Lys Arg Glu Asp
  1               5                  10                  15

Ile Val Asn Gln Met Thr Glu Ala Cys Leu Asn Gln Ser Leu Asp Ala
                 20                  25                  30

Leu Leu Ser Arg Asp Leu Ile Met Lys Glu Asp Tyr Glu Leu Val Ser
             35                  40                  45

Thr Lys Pro Thr Arg Thr Ser Lys Val Arg Gln Leu Leu Asp Thr Thr
         50                  55                  60

Asp Ile Gln Gly Glu Glu Phe Ala Lys Val Ile Val Gln Lys Leu Lys
 65                  70                  75                  80

Asp Asn Lys Gln Met Gly Leu Gln Pro Tyr Pro Glu Ile Leu Val Val
                 85                  90                  95

Ser Arg Ser Pro Ser Leu Asn Leu Leu Gln Asn Lys Ser Met
                100                 105                 110

<210> SEQ ID NO 7
<211> LENGTH: 3382
<212> TYPE: DNA
<213> ORGANISM: Homo sapiens
<220> FEATURE:
<221> NAME/KEY: CDS
<222> LOCATION: (245)...(3103)

<400> SEQUENCE: 7 ttttatggg aatcgcagct tggaagagac agarcaattc cagaawtaaa ttgraattga      60
agatttaacc aatgttgttt taaaatattc taacttcaaa gaatgatgcc agaacttwaa    120
aagggrctgc gcagagtagc aggggccctg gagggcgcgg cctgaatcct gattgcccttt  180 ctgctgagag gacacacgca gctgaagatg aatttgggaa aagtagccgc ttgctacttt   240 aact atg gaa gag cag ggc cac agt gag atg gaa ata atc cca tca gag   289
     Met Glu Glu Gln Gly His Ser Glu Met Glu Ile Ile Pro Ser Glu
       1               5                  10                  15 tct cac ccc cac att caa tta ctg aaa agc aat cgg gaa ctt ctg gtc   337
Ser His Pro His Ile Gln Leu Leu Lys Ser Asn Arg Glu Leu Leu Val
                 20                  25                  30 act cac atc cgc aat act cag tgt ctg gtg gac aac ttg ctg aag aat   385
Thr His Ile Arg Asn Thr Gln Cys Leu Val Asp Asn Leu Leu Lys Asn
             35                  40                  45 gac tac ttc tcg gcc gaa gat gcg gag att gtg tgt gcc tgc ccc acc   433
Asp Tyr Phe Ser Ala Glu Asp Ala Glu Ile Val Cys Ala Cys Pro Thr
         50                  55                  60 cag cct gac aag gtc cgc aaa att ctg gac ctg gta cag agc aag ggc   481
Gln Pro Asp Lys Val Arg Lys Ile Leu Asp Leu Val Gln Ser Lys Gly
 65                  70                  75 gag gag gtg tcc gag ttc ttc ctc tac ttg ctc cag caa ctc gca gat   529
Glu Glu Val Ser Glu Phe Phe Leu Tyr Leu Leu Gln Gln Leu Ala Asp
 80                  85                  90                  95 gcc tac gtg gac ctc agg cct tgg ctg ctg gag atc ggc ttc tcc cct   577
Ala Tyr Val Asp Leu Arg Pro Trp Leu Leu Glu Ile Gly Phe Ser Pro
                100                 105                 110 tcc ctg ctc act cag agc aaa gtc gtg gtc aac act gac cca gtg agc   625
Ser Leu Leu Thr Gln Ser Lys Val Val Val Asn Thr Asp Pro Val Ser
                115                 120                 125 agg tat acc cag cag ctg cga cac cat ctg ggc cgt gac tcc aag ttc   673
Arg Tyr Thr Gln Gln Leu Arg His His Leu Gly Arg Asp Ser Lys Phe
                130                 135                 140
```

```
gtg ctg tgc tat gcc cag aag gag gag ctg ctg ctg gag gag atc tac    721
Val Leu Cys Tyr Ala Gln Lys Glu Glu Leu Leu Leu Glu Glu Ile Tyr
    145                 150                 155 atg gac acc atc atg gag ctg gtt ggc ttc agc aat gag agc ctg ggc    769
Met Asp Thr Ile Met Glu Leu Val Gly Phe Ser Asn Glu Ser Leu Gly
160                 165                 170                 175 agc ctg aac agc ctg gcc tgc ctc ctg gac cac acc acc ggc atc ctc    817
Ser Leu Asn Ser Leu Ala Cys Leu Leu Asp His Thr Thr Gly Ile Leu
                180                 185                 190 aat gag cag ggt gag acc atc ttc atc ctg ggt gat gct ggg gtg ggc    865
Asn Glu Gln Gly Glu Thr Ile Phe Ile Leu Gly Asp Ala Gly Val Gly
            195                 200                 205 aag tcc atg ctg cta cag cgg ctg cag agc ctc tgg gcc acg ggc cgg    913
Lys Ser Met Leu Leu Gln Arg Leu Gln Ser Leu Trp Ala Thr Gly Arg
        210                 215                 220 cta gac gca ggg gtc aaa ttc ttc ttc cac ttt cgc tgc cgc atg ttc    961
Leu Asp Ala Gly Val Lys Phe Phe Phe His Phe Arg Cys Arg Met Phe
    225                 230                 235 agc tgc ttc aag gaa agt gac agg ctg tgt ctg cag gac ctg ctc ttc   1009
Ser Cys Phe Lys Glu Ser Asp Arg Leu Cys Leu Gln Asp Leu Leu Phe
240                 245                 250                 255 aag cac tac tgc tac cca gag cgg gac ccc gag gag gtg ttt gcc ttc   1057
Lys His Tyr Cys Tyr Pro Glu Arg Asp Pro Glu Glu Val Phe Ala Phe
                260                 265                 270 ctg ctg cgc ttc ccc cac gtg gcc ctc ttc acc ttc gat ggc ctg gac   1105
Leu Leu Arg Phe Pro His Val Ala Leu Phe Thr Phe Asp Gly Leu Asp
            275                 280                 285 gag ctg cac tcg gac ttg gac ctg agc cgc gtg cct gac agc tcc tgc   1153
Glu Leu His Ser Asp Leu Asp Leu Ser Arg Val Pro Asp Ser Ser Cys
        290                 295                 300 ccc tgg gag cct gcc cac ccc ctg gtc ttg ctg gcc aac ctg ctc agt   1201
Pro Trp Glu Pro Ala His Pro Leu Val Leu Leu Ala Asn Leu Leu Ser
    305                 310                 315 ggg aag ctg ctc aag ggg gct agc aag ctg ctc aca gcc cgc aca ggc   1249
Gly Lys Leu Leu Lys Gly Ala Ser Lys Leu Leu Thr Ala Arg Thr Gly
320                 325                 330                 335 atc gag gtc ccg cgc cag ttc ctg cgg aag aag gtg ctt ctc cgg ggc   1297
Ile Glu Val Pro Arg Gln Phe Leu Arg Lys Lys Val Leu Leu Arg Gly
                340                 345                 350 ttc tcc ccc agc cac ctg cgc gcc tat gcc agg agg atg ttc ccc gag   1345
Phe Ser Pro Ser His Leu Arg Ala Tyr Ala Arg Arg Met Phe Pro Glu
            355                 360                 365 cgg gcc ctg cag gac cgc ctg ctg agc cag ctg gag gcc aac ccc aac   1393
Arg Ala Leu Gln Asp Arg Leu Leu Ser Gln Leu Glu Ala Asn Pro Asn
        370                 375                 380 ctc tgc agc ctg tgc tct gtg ccc ctc ttc tgc tgg atc atc ttc cgg   1441
Leu Cys Ser Leu Cys Ser Val Pro Leu Phe Cys Trp Ile Ile Phe Arg
    385                 390                 395 tgc ttc cag cac ttc cgt gct gcc ttt gaa ggc tca cca cag ctg ccc   1489
Cys Phe Gln His Phe Arg Ala Ala Phe Glu Gly Ser Pro Gln Leu Pro
400                 405                 410                 415 gac tgc acg atg acc ctg aca gat gtc ttc ctc ctg gtc act gag gtc   1537
Asp Cys Thr Met Thr Leu Thr Asp Val Phe Leu Leu Val Thr Glu Val
                420                 425                 430 cat ctg aac agg atg cag ccc agc agc ctg gtg cag cgg aac aca cgc   1585
His Leu Asn Arg Met Gln Pro Ser Ser Leu Val Gln Arg Asn Thr Arg
            435                 440                 445 agc cca gtg gag acc ctc cac gcc ggc cgg gac act ctg tgc tcg ctg   1633
Ser Pro Val Glu Thr Leu His Ala Gly Arg Asp Thr Leu Cys Ser Leu
        450                 455                 460
```

-continued

| | | |
|---|---|---|
| ggg cag gtg gcc cac cgg ggc atg gag aag agc ctc ttt gtc ttc acc<br>Gly Gln Val Ala His Arg Gly Met Glu Lys Ser Leu Phe Val Phe Thr<br>465 470 475 | 1681 | |
| cag gag gag gtg cag gcc tcc ggg ctg cag gag aga gac atg cag ctg<br>Gln Glu Glu Val Gln Ala Ser Gly Leu Gln Glu Arg Asp Met Gln Leu<br>480 485 490 495 | 1729 | |
| ggc ttc ctg cgg gct ttg ccg gag ctg ggc ccc ggg ggt gac cag cag<br>Gly Phe Leu Arg Ala Leu Pro Glu Leu Gly Pro Gly Gly Asp Gln Gln<br>500 505 510 | 1777 | |
| tcc tat gag ttt ttc cac ctc acc ctc cag gcc ttc ttt aca gcc ttc<br>Ser Tyr Glu Phe Phe His Leu Thr Leu Gln Ala Phe Phe Thr Ala Phe<br>515 520 525 | 1825 | |
| ttc ctc gtg ctg gac gac agg gtg ggc act cag gag ctg ctc agg ttc<br>Phe Leu Val Leu Asp Asp Arg Val Gly Thr Gln Glu Leu Leu Arg Phe<br>530 535 540 | 1873 | |
| ttc cag gag tgg atg ccc cct gcg ggg gca gcg acc acg tcc tgc tat<br>Phe Gln Glu Trp Met Pro Pro Ala Gly Ala Ala Thr Thr Ser Cys Tyr<br>545 550 555 | 1921 | |
| cct ccc ttc ctc ccg ttc cag tgc ctg cag ggc agt ggt ccg gcg cgg<br>Pro Pro Phe Leu Pro Phe Gln Cys Leu Gln Gly Ser Gly Pro Ala Arg<br>560 565 570 575 | 1969 | |
| gaa gac ctc ttc aag aac aag gat cac ttc cag ttc acc aac ctc ttc<br>Glu Asp Leu Phe Lys Asn Lys Asp His Phe Gln Phe Thr Asn Leu Phe<br>580 585 590 | 2017 | |
| ctg tgc ggg ctg ttg tcc aaa gcc aaa cag aaa ctc ctg cgg cat ctg<br>Leu Cys Gly Leu Leu Ser Lys Ala Lys Gln Lys Leu Leu Arg His Leu<br>595 600 605 | 2065 | |
| gtg ccc gcg gca gcc ctg agg aga aag cgc aag gcc ctg tgg gca cac<br>Val Pro Ala Ala Ala Leu Arg Arg Lys Arg Lys Ala Leu Trp Ala His<br>610 615 620 | 2113 | |
| ctg ttt tcc agc ctg cgg ggc tac ctg aag agc ctg ccc cgc gtt cag<br>Leu Phe Ser Ser Leu Arg Gly Tyr Leu Lys Ser Leu Pro Arg Val Gln<br>625 630 635 | 2161 | |
| gtc gaa agc ttc aac cag gtg cag gcc atg ccc acg ttc atc tgg atg<br>Val Glu Ser Phe Asn Gln Val Gln Ala Met Pro Thr Phe Ile Trp Met<br>640 645 650 655 | 2209 | |
| ctg cgc tgc atc tac gag aca cag agc cag aag gtg ggg cag ctg gcg<br>Leu Arg Cys Ile Tyr Glu Thr Gln Ser Gln Lys Val Gly Gln Leu Ala<br>660 665 670 | 2257 | |
| gcc agg ggc atc tgc gcc aac tac ctc aag ctg acc tac tgc aac gcc<br>Ala Arg Gly Ile Cys Ala Asn Tyr Leu Lys Leu Thr Tyr Cys Asn Ala<br>675 680 685 | 2305 | |
| tgc tcg gcc gac tgc agc gcc ctc tcc ttc gtc ctg cat cac ttc ccc<br>Cys Ser Ala Asp Cys Ser Ala Leu Ser Phe Val Leu His His Phe Pro<br>690 695 700 | 2353 | |
| aag cgg ctg gcc cta gac cta gac aac aac aat ctc aac gac tac ggc<br>Lys Arg Leu Ala Leu Asp Leu Asp Asn Asn Asn Leu Asn Asp Tyr Gly<br>705 710 715 | 2401 | |
| gtg cgg gag ctg cag ccc tgc ttc agc cgc ctc act gtt ctc aga ctc<br>Val Arg Glu Leu Gln Pro Cys Phe Ser Arg Leu Thr Val Leu Arg Leu<br>720 725 730 735 | 2449 | |
| agc gta aac cag atc act gac ggt ggg gta aag gtg cta agc gaa gag<br>Ser Val Asn Gln Ile Thr Asp Gly Gly Val Lys Val Leu Ser Glu Glu<br>740 745 750 | 2497 | |
| ctg acc aaa tac aaa att gtg acc tat ttg ggt tta tac aac aac cag<br>Leu Thr Lys Tyr Lys Ile Val Thr Tyr Leu Gly Leu Tyr Asn Asn Gln<br>755 760 765 | 2545 | |
| atc acc gat gtc gga gcc agg tac gtc acc aaa atc ctg gat gaa tgc<br>Ile Thr Asp Val Gly Ala Arg Tyr Val Thr Lys Ile Leu Asp Glu Cys | 2593 | |

-continued

```
            770                 775                 780
aaa ggc ctc acg cat ctt aaa ctg gga aaa aac aaa ata aca agt gaa      2641
Lys Gly Leu Thr His Leu Lys Leu Gly Lys Asn Lys Ile Thr Ser Glu
        785                 790                 795 gga ggg aag tat ctc gcc ctg gct gtg aag aac agc aaa tca atc tct      2689
Gly Gly Lys Tyr Leu Ala Leu Ala Val Lys Asn Ser Lys Ser Ile Ser
800                 805                 810                 815 gag gtt ggg atg tgg ggc aat caa gtt ggg gat gaa gga gca aaa gcc      2737
Glu Val Gly Met Trp Gly Asn Gln Val Gly Asp Glu Gly Ala Lys Ala
                820                 825                 830 ttc gca gag gct ctg cgg aac cac ccc agc ttg acc acc ctg agt ctt      2785
Phe Ala Glu Ala Leu Arg Asn His Pro Ser Leu Thr Thr Leu Ser Leu
            835                 840                 845 gcg tcc aac ggc atc tcc aca gaa gga gga aag agc ctt gcg agg gcc      2833
Ala Ser Asn Gly Ile Ser Thr Glu Gly Gly Lys Ser Leu Ala Arg Ala
        850                 855                 860 ctg cag cag aac acg tct cta gaa ata ctg tgg ctg acc caa aat gaa      2881
Leu Gln Gln Asn Thr Ser Leu Glu Ile Leu Trp Leu Thr Gln Asn Glu
    865                 870                 875 ctc aac gat gaa gtg gca gag agt ttg gca gaa atg ttg aaa gtc aac      2929
Leu Asn Asp Glu Val Ala Glu Ser Leu Ala Glu Met Leu Lys Val Asn
880                 885                 890                 895 cag acg tta aag cat tta tgg ctt atc cag aat cag atc aca gct aag      2977
Gln Thr Leu Lys His Leu Trp Leu Ile Gln Asn Gln Ile Thr Ala Lys
                900                 905                 910 ggg act gcc cag ctg gca gat gcg tta cag agc aac act ggc ata aca      3025
Gly Thr Ala Gln Leu Ala Asp Ala Leu Gln Ser Asn Thr Gly Ile Thr
            915                 920                 925 gag att tgc cta aat gga aac ctg ata aaa cca gag gag gcc aaa gtc      3073
Glu Ile Cys Leu Asn Gly Asn Leu Ile Lys Pro Glu Glu Ala Lys Val
        930                 935                 940 tat gaa gat gag aag cgg att atc tgt ttc tgagaggatg ctttcctgtt       3123
Tyr Glu Asp Glu Lys Arg Ile Ile Cys Phe
    945                 950 catgggttt tgccctgga gcctcagcag caaatgccac tctgggcagt cttttgtgtc     3183
agtgtcttaa aggggcctgc gcaggcggga ctatcaggag tccactgcct ycatgatgca   3243
agccagcttc ctgtgcagaa ggtctggtcg gcaaactccc taagtacccg ctacaattct   3303
gcagaaaaag aatgtgtctt gcgagctgtt gtagttacag taaatacact gtgaagagaa   3363
aaaaaaaacg gacgcgtgg                                                3382

<210> SEQ ID NO 8
<211> LENGTH: 953
<212> TYPE: PRT
<213> ORGANISM: Homo sapiens

<400> SEQUENCE: 8

Met Glu Glu Gln Gly His Ser Glu Met Glu Ile Ile Pro Ser Glu Ser
1               5                   10                  15

His Pro His Ile Gln Leu Leu Lys Ser Asn Arg Glu Leu Leu Val Thr
            20                  25                  30

His Ile Arg Asn Thr Gln Cys Leu Val Asp Asn Leu Leu Lys Asn Asp
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80
```

-continued

```
Glu Val Ser Glu Phe Phe Leu Tyr Leu Leu Gln Gln Leu Ala Asp Ala
             85                  90                  95

Tyr Val Asp Leu Arg Pro Trp Leu Leu Glu Ile Gly Phe Ser Pro Ser
            100                 105                 110

Leu Leu Thr Gln Ser Lys Val Val Asn Thr Asp Pro Val Ser Arg
            115                 120                 125

Tyr Thr Gln Gln Leu Arg His His Leu Gly Arg Asp Ser Lys Phe Val
            130                 135                 140

Leu Cys Tyr Ala Gln Lys Glu Leu Leu Glu Ile Tyr Met
145                 150                 155                 160

Asp Thr Ile Met Glu Leu Val Gly Phe Ser Asn Glu Ser Leu Gly Ser
                165                 170                 175

Leu Asn Ser Leu Ala Cys Leu Leu Asp His Thr Thr Gly Ile Leu Asn
            180                 185                 190

Glu Gln Gly Glu Thr Ile Phe Ile Leu Gly Asp Ala Gly Val Gly Lys
            195                 200                 205

Ser Met Leu Leu Gln Arg Leu Gln Ser Leu Trp Ala Thr Gly Arg Leu
    210                 215                 220

Asp Ala Gly Val Lys Phe Phe His Phe Arg Cys Arg Met Phe Ser
225                 230                 235                 240

Cys Phe Lys Glu Ser Asp Arg Leu Cys Leu Gln Asp Leu Leu Phe Lys
            245                 250                 255

His Tyr Cys Tyr Pro Glu Arg Asp Pro Glu Val Phe Ala Phe Leu
            260                 265                 270

Leu Arg Phe Pro His Val Ala Leu Phe Thr Phe Asp Gly Leu Asp Glu
            275                 280                 285

Leu His Ser Asp Leu Asp Leu Ser Arg Val Pro Asp Ser Ser Cys Pro
    290                 295                 300

Trp Glu Pro Ala His Pro Leu Val Leu Ala Asn Leu Leu Ser Gly
305                 310                 315                 320

Lys Leu Leu Lys Gly Ala Ser Lys Leu Leu Thr Ala Arg Thr Gly Ile
                325                 330                 335

Glu Val Pro Arg Gln Phe Leu Arg Lys Lys Val Leu Leu Arg Gly Phe
            340                 345                 350

Ser Pro Ser His Leu Arg Ala Tyr Ala Arg Arg Met Phe Pro Glu Arg
    355                 360                 365

Ala Leu Gln Asp Arg Leu Leu Ser Gln Leu Glu Ala Asn Pro Asn Leu
    370                 375                 380

Cys Ser Leu Cys Ser Val Pro Leu Phe Cys Trp Ile Ile Phe Arg Cys
385                 390                 395                 400

Phe Gln His Phe Arg Ala Ala Phe Glu Gly Ser Pro Gln Leu Pro Asp
            405                 410                 415

Cys Thr Met Thr Leu Thr Asp Val Phe Leu Leu Val Thr Glu Val His
            420                 425                 430

Leu Asn Arg Met Gln Pro Ser Ser Leu Val Gln Arg Asn Thr Arg Ser
    435                 440                 445

Pro Val Glu Thr Leu His Ala Gly Arg Asp Thr Leu Cys Ser Leu Gly
    450                 455                 460

Gln Val Ala His Arg Gly Met Glu Lys Ser Leu Phe Val Phe Thr Gln
465                 470                 475                 480

Glu Glu Val Gln Ala Ser Gly Leu Gln Glu Arg Asp Met Gln Leu Gly
            485                 490                 495

Phe Leu Arg Ala Leu Pro Glu Leu Gly Pro Gly Gly Asp Gln Gln Ser
```

-continued

```
              500                 505                 510
Tyr Glu Phe Phe His Leu Thr Leu Gln Ala Phe Phe Thr Ala Phe Phe
              515                 520                 525

Leu Val Leu Asp Asp Arg Val Gly Thr Gln Glu Leu Leu Arg Phe Phe
              530                 535                 540

Gln Glu Trp Met Pro Pro Ala Gly Ala Ala Thr Thr Ser Cys Tyr Pro
545                 550                 555                 560

Pro Phe Leu Pro Phe Gln Cys Leu Gln Gly Ser Gly Pro Ala Arg Glu
                  565                 570                 575

Asp Leu Phe Lys Asn Lys Asp His Phe Gln Phe Thr Asn Leu Phe Leu
                  580                 585                 590

Cys Gly Leu Leu Ser Lys Ala Lys Gln Lys Leu Leu Arg His Leu Val
              595                 600                 605

Pro Ala Ala Ala Leu Arg Arg Lys Arg Lys Ala Leu Trp Ala His Leu
              610                 615                 620

Phe Ser Ser Leu Arg Gly Tyr Leu Lys Ser Leu Pro Arg Val Gln Val
625                 630                 635                 640

Glu Ser Phe Asn Gln Val Gln Ala Met Pro Thr Phe Ile Trp Met Leu
                  645                 650                 655

Arg Cys Ile Tyr Glu Thr Gln Ser Gln Lys Val Gly Gln Leu Ala Ala
              660                 665                 670

Arg Gly Ile Cys Ala Asn Tyr Leu Lys Leu Thr Tyr Cys Asn Ala Cys
              675                 680                 685

Ser Ala Asp Cys Ser Ala Leu Ser Phe Val Leu His His Phe Pro Lys
              690                 695                 700

Arg Leu Ala Leu Asp Leu Asp Asn Asn Leu Asn Asp Tyr Gly Val
705                 710                 715                 720

Arg Glu Leu Gln Pro Cys Phe Ser Arg Leu Thr Val Leu Arg Leu Ser
                  725                 730                 735

Val Asn Gln Ile Thr Asp Gly Gly Val Lys Val Leu Ser Glu Glu Leu
                  740                 745                 750

Thr Lys Tyr Lys Ile Val Thr Tyr Leu Gly Leu Tyr Asn Asn Gln Ile
              755                 760                 765

Thr Asp Val Gly Ala Arg Tyr Val Thr Lys Ile Leu Asp Glu Cys Lys
              770                 775                 780

Gly Leu Thr His Leu Lys Leu Gly Lys Asn Lys Ile Thr Ser Glu Gly
785                 790                 795                 800

Gly Lys Tyr Leu Ala Leu Ala Val Lys Asn Ser Lys Ser Ile Ser Glu
                  805                 810                 815

Val Gly Met Trp Gly Asn Gln Val Gly Asp Glu Gly Ala Lys Ala Phe
              820                 825                 830

Ala Glu Ala Leu Arg Asn His Pro Ser Leu Thr Thr Leu Ser Leu Ala
              835                 840                 845

Ser Asn Gly Ile Ser Thr Glu Gly Gly Lys Ser Leu Ala Arg Ala Leu
850                 855                 860

Gln Gln Asn Thr Ser Leu Glu Ile Leu Trp Leu Thr Gln Asn Glu Leu
865                 870                 875                 880

Asn Asp Glu Val Ala Glu Ser Leu Ala Glu Met Leu Lys Val Asn Gln
                  885                 890                 895

Thr Leu Lys His Leu Trp Leu Ile Gln Asn Gln Ile Thr Ala Lys Gly
              900                 905                 910

Thr Ala Gln Leu Ala Asp Ala Leu Gln Ser Asn Thr Gly Ile Thr Glu
              915                 920                 925
```

Ile Cys Leu Asn Gly Asn Leu Ile Lys Pro Glu Glu Ala Lys Val Tyr
    930             935             940

Glu Asp Glu Lys Arg Ile Ile Cys Phe
945             950

<210> SEQ ID NO 9
<211> LENGTH: 2859
<212> TYPE: DNA
<213> ORGANISM: Homo sapiens

<400> SEQUENCE: 9

| | | |
|---|---|---|
| atggaagagc agggccacag tgagatggaa ataatcccat cagagtctca cccccacatt | 60 |
| caattactga aaagcaatcg gaacttctg tcactcaca tccgcaatac tcagtgtctg | 120 |
| gtggacaact tgctgaagaa tgactacttc tcggccgaag atgcggagat tgtgtgtgcc | 180 |
| tgccccaccc agcctgacaa ggtccgcaaa attctggacc tggtacagag caagggcgag | 240 |
| gaggtgtccg agttcttcct ctacttgctc cagcaactcg cagatgccta cgtggacctc | 300 |
| aggccttggc tgctggagat cggcttctcc ccttccctgc tcactcagag caaagtcgtg | 360 |
| gtcaacactg acccagtgag caggtatacc cagcagctgc gacaccatct gggccgtgac | 420 |
| tccaagttcg tgctgtgcta tgcccagaag gaggagctgc tgctggagga gatctacatg | 480 |
| gacaccatca tggagctggt tggcttcagc aatgagagcc tgggcagcct gaacagcctg | 540 |
| gcctgcctcc tggaccacac caccggcatc ctcaatgagc agggtgagac catcttcatc | 600 |
| ctgggtgatg ctgggtgg caagtccatg ctgctacagc ggctgcagag cctctgggcc | 660 |
| acgggccggc tagacgcagg ggtcaaattc ttcttccact tcgctgccg catgttcagc | 720 |
| tgcttcaagg aaagtgacag gctgtgtctg caggacctgc tcttcaagca ctactgctac | 780 |
| ccagagcggg accccgagga ggtgtttgcc ttcctgctgc gcttccccca cgtggccctc | 840 |
| ttcaccttcg atggcctgga cgagctgcac tcggacttgg acctgagccg cgtgcctgac | 900 |
| agctcctgcc cctgggagcc tgcccacccc ctggtcttgc tggccaacct gctcagtggg | 960 |
| aagctgctca agggggctag caagctgctc acagcccgca caggcatcga ggtcccgcgc | 1020 |
| cagttcctgc ggaagaaggt gcttctccgg ggcttctccc ccagccacct gcgcgcctat | 1080 |
| gccaggagga tgttccccga gcgggccctg caggaccgc tgctgagcca gctggaggcc | 1140 |
| aaccccaacc tctgcagcct gtgctctgtg cccctcttct gctggatcat cttccggtgc | 1200 |
| ttccagcact tccgtgctgc cttgaaggc tcaccacagc tgcccgactg cacgatgacc | 1260 |
| ctgacagatg tcttcctcct ggtcactgag gtccatctga acaggatgca gcccagcagc | 1320 |
| ctggtgcagc ggaacacacg cagcccagtg gagaccctcc acgccggccg ggacactctg | 1380 |
| tgctcgctgg ggcaggtggc ccaccggggc atggagaaga gcctctttgt cttcacccag | 1440 |
| gaggaggtgc aggcctccgg gctgcaggag agagacatgc agctgggctt cctgcgggct | 1500 |
| ttgccggagc tgggccccgg gggtgaccag cagtcctatg agtttttcca cctcaccctc | 1560 |
| caggccttct ttacagcctt cttcctcgtg ctggacgaca gggtgggcac tcaggagctg | 1620 |
| ctcaggttct tccaggagtg gatgccccct gcggggcag cgaccacgtc ctgctatcct | 1680 |
| cccttcctcc cgttccagtg cctgcaggga gtggtccgg cgcgggaaga cctcttcaag | 1740 |
| aacaaggatc acttccagtt caccaacctc ttcctgtgcg gctgttgtc caaagccaaa | 1800 |
| cagaaactcc tgcggcatct ggtgcccgcg gcagccctga ggagaaagcg caaggccctg | 1860 |
| tgggcacacc tgttttccag cctgcggggc tacctgaaga gcctgccccg cgttcaggtc | 1920 |

-continued

```
gaaagcttca accaggtgca ggccatgccc acgttcatct ggatgctgcg ctgcatctac    1980
gagacacaga gccagaaggt ggggcagctg gcggccaggg gcatctgcgc caactaccctc   2040 aagctgacct actgcaacgc ctgctcggcc gactgcagcg ccctctcctt cgtcctgcat    2100
cacttcccca gcggctggc cctagaccta gacaacaaca atctcaacga ctacggcgtg     2160
cgggagctgc agccctgctt cagccgcctc actgttctca gactcagcgt aaaccagatc    2220
actgacggtg gggtaaaggt gctaagcgaa gagctgacca aatacaaaat tgtgacctat    2280
ttgggtttat acaacaacca gatcaccgat gtcggagcca ggtacgtcac caaaatcctg    2340
gatgaatgca aaggcctcac gcatcttaaa ctgggaaaaa acaaaataac aagtgaagga    2400
gggaagtatc tcgccctggc tgtgaagaac agcaaatcaa tctctgaggt tgggatgtgg    2460
ggcaatcaag ttggggatga aggagcaaaa gccttcgcag aggctctgcg gaaccacccc    2520
agcttgacca ccctgagtct tgcgtccaac ggcatctcca cagaaggagg aaagagcctt    2580
gcgagggccc tgcagcagaa cacgtctcta gaaatactgt ggctgaccca aaatgaactc    2640
aacgatgaag tggcagagag tttggcagaa atgttgaaag tcaaccagac gttaaagcat    2700
ttatggctta tccagaatca gatcacagct aaggggactg cccagctggc agatgcgtta    2760
cagagcaaca ctggcataac agagatttgc ctaaatggaa acctgataaa accagaggag    2820
gccaaagtct atgaagatga aagcggatt atctgtttc                            2859
```

<210> SEQ ID NO 10
<211> LENGTH: 100
<212> TYPE: PRT
<213> ORGANISM: Homo sapiens

<400> SEQUENCE: 10

```
Glu Ser His Pro His Ile Gln Leu Leu Lys Ser Asn Arg Glu Leu Leu
 1               5                  10                  15

Val Thr His Ile Arg Asn Thr Gln Cys Leu Val Asp Asn Leu Leu Lys
            20                  25                  30

Asn Asp Tyr Phe Ser Ala Glu Asp Ala Glu Ile Val Cys Ala Cys Pro
        35                  40                  45

Thr Gln Pro Asp Lys Val Arg Lys Ile Leu Asp Leu Val Gln Ser Lys
    50                  55                  60

Gly Glu Glu Val Ser Glu Phe Phe Leu Tyr Leu Gln Gln Leu Ala
65                  70                  75                  80

Asp Ala Tyr Val Asp Leu Arg Pro Trp Leu Leu Glu Ile Gly Phe Ser
                85                  90                  95

Pro Ser Leu Leu
            100
```

<210> SEQ ID NO 11
<211> LENGTH: 200
<212> TYPE: PRT
<213> ORGANISM: Homo sapiens

<400> SEQUENCE: 11

```
Ile Phe Ile Leu Gly Asp Ala Gly Val Gly Lys Ser Met Leu Leu Gln
 1               5                  10                  15

Arg Leu Gln Ser Leu Trp Ala Thr Gly Arg Leu Asp Ala Gly Val Lys
            20                  25                  30

Phe Phe Phe His Phe Arg Cys Arg Met Phe Ser Cys Phe Lys Glu Ser
        35                  40                  45

Asp Arg Leu Cys Leu Gln Asp Leu Leu Phe Lys His Tyr Cys Tyr Pro
```

-continued

```
                  50                  55                  60
Glu Arg Asp Pro Glu Glu Val Phe Ala Phe Leu Leu Arg Phe Pro His
 65                  70                  75                  80

Val Ala Leu Phe Thr Phe Asp Gly Leu Asp Glu Leu His Ser Asp Leu
                 85                  90                  95

Asp Leu Ser Arg Val Pro Asp Ser Ser Cys Pro Trp Glu Pro Ala His
                100                 105                 110

Pro Leu Val Leu Leu Ala Asn Leu Leu Ser Gly Lys Leu Leu Lys Gly
                115                 120                 125

Ala Ser Lys Leu Leu Thr Ala Arg Thr Gly Ile Glu Val Pro Arg Gln
130                 135                 140

Phe Leu Arg Lys Lys Val Leu Leu Arg Gly Phe Ser Pro Ser His Leu
145                 150                 155                 160

Arg Ala Tyr Ala Arg Arg Met Phe Pro Glu Arg Ala Leu Gln Asp Arg
                165                 170                 175

Leu Leu Ser Gln Leu Glu Ala Asn Pro Asn Leu Cys Ser Leu Cys Ser
                180                 185                 190

Val Pro Leu Phe Cys Trp Ile Ile
                195                 200

<210> SEQ ID NO 12
<211> LENGTH: 8
<212> TYPE: PRT
<213> ORGANISM: Homo sapiens

<400> SEQUENCE: 12

Gly Asp Ala Gly Val Gly Lys Ser
 1               5

<210> SEQ ID NO 13
<211> LENGTH: 5
<212> TYPE: PRT
<213> ORGANISM: Homo sapiens

<400> SEQUENCE: 13

Leu Phe Thr Phe Asp
 1               5

<210> SEQ ID NO 14
<211> LENGTH: 12
<212> TYPE: PRT
<213> ORGANISM: Homo sapiens

<400> SEQUENCE: 14

Ser Lys Leu Leu Thr Ala Arg Thr Gly Ile Glu Val
 1               5                  10

<210> SEQ ID NO 15
<211> LENGTH: 28
<212> TYPE: PRT
<213> ORGANISM: Homo sapiens

<400> SEQUENCE: 15

Gly Ile Cys Ala Asn Tyr Leu Lys Leu Thr Tyr Cys Asn Ala Cys Ser
 1               5                  10                  15

Ala Asp Cys Ser Ala Leu Ser Phe Val Leu His His
                 20                  25

<210> SEQ ID NO 16
<211> LENGTH: 26
```

```
<212> TYPE: PRT
<213> ORGANISM: Homo sapiens

<400> SEQUENCE: 16

Phe Pro Lys Arg Leu Ala Leu Asp Leu Asp Asn Asn Asn Leu Asn Asp
  1               5                  10                  15

Tyr Gly Val Arg Glu Leu Gln Pro Cys Phe
             20                  25

<210> SEQ ID NO 17
<211> LENGTH: 27
<212> TYPE: PRT
<213> ORGANISM: Homo sapiens

<400> SEQUENCE: 17

Ser Arg Leu Thr Val Leu Arg Leu Ser Val Asn Gln Ile Thr Asp Gly
  1               5                  10                  15

Gly Val Lys Val Leu Ser Glu Glu Leu Thr Lys
             20                  25

<210> SEQ ID NO 18
<211> LENGTH: 28
<212> TYPE: PRT
<213> ORGANISM: Homo sapiens

<400> SEQUENCE: 18

Tyr Lys Ile Val Thr Tyr Leu Gly Leu Tyr Asn Asn Gln Ile Thr Asp
  1               5                  10                  15

Val Gly Ala Arg Tyr Val Thr Lys Ile Leu Asp Glu
             20                  25

<210> SEQ ID NO 19
<211> LENGTH: 28
<212> TYPE: PRT
<213> ORGANISM: Homo sapiens

<400> SEQUENCE: 19

Cys Lys Gly Leu Thr His Leu Lys Leu Gly Lys Asn Lys Ile Thr Ser
  1               5                  10                  15

Glu Gly Gly Lys Tyr Leu Ala Leu Ala Val Lys Asn
             20                  25

<210> SEQ ID NO 20
<211> LENGTH: 28
<212> TYPE: PRT
<213> ORGANISM: Homo sapiens

<400> SEQUENCE: 20

Ser Lys Ser Ile Ser Glu Val Gly Met Trp Gly Asn Gln Val Gly Asp
  1               5                  10                  15

Glu Gly Ala Lys Ala Phe Ala Glu Ala Leu Arg Asn
             20                  25

<210> SEQ ID NO 21
<211> LENGTH: 28
<212> TYPE: PRT
<213> ORGANISM: Homo sapiens

<400> SEQUENCE: 21

His Pro Ser Leu Thr Thr Leu Ser Leu Ala Ser Asn Gly Ile Ser Thr
  1               5                  10                  15

Glu Gly Gly Lys Ser Leu Ala Arg Ala Leu Gln Gln
```

```
            20                  25

<210> SEQ ID NO 22
<211> LENGTH: 28
<212> TYPE: PRT
<213> ORGANISM: Homo sapiens

<400> SEQUENCE: 22

Asn Thr Ser Leu Glu Ile Leu Trp Leu Thr Gln Asn Glu Leu Asn Asp
 1               5                  10                  15

Glu Val Ala Glu Ser Leu Ala Glu Met Leu Lys Val
            20                  25

<210> SEQ ID NO 23
<211> LENGTH: 28
<212> TYPE: PRT
<213> ORGANISM: Homo sapiens

<400> SEQUENCE: 23

Asn Gln Thr Leu Lys His Leu Trp Leu Ile Gln Asn Gln Ile Thr Ala
 1               5                  10                  15

Lys Gly Thr Ala Gln Leu Ala Asp Ala Leu Gln Ser
            20                  25

<210> SEQ ID NO 24
<211> LENGTH: 28
<212> TYPE: PRT
<213> ORGANISM: Homo sapiens

<400> SEQUENCE: 24

Asn Thr Gly Ile Thr Glu Ile Cys Leu Asn Gly Asn Leu Ile Lys Pro
 1               5                  10                  15

Glu Glu Ala Lys Val Tyr Glu Asp Glu Lys Arg Ile
            20                  25

<210> SEQ ID NO 25
<211> LENGTH: 3080
<212> TYPE: DNA
<213> ORGANISM: Homo sapiens
<220> FEATURE:
<221> NAME/KEY: CDS
<222> LOCATION: (1)...(1470)

<400> SEQUENCE: 25 cac gcg tcc gac ttg ctg aag aat gac tac ttc tcg gcc gaa gat gcg      48
His Ala Ser Asp Leu Leu Lys Asn Asp Tyr Phe Ser Ala Glu Asp Ala
 1               5                  10                  15 gag att gtg tgt gcc tgc ccc acc cag cct gac aag gtc cgc aaa att      96
Glu Ile Val Cys Ala Cys Pro Thr Gln Pro Asp Lys Val Arg Lys Ile
            20                  25                  30 ctg gac ctg gta cag agc aag ggc gag gag gtg tcc gag ttc ttc ctc     144
Leu Asp Leu Val Gln Ser Lys Gly Glu Glu Val Ser Glu Phe Phe Leu
        35                  40                  45 tac ttg ctc cag caa ctc gca gat gcc tac gtg gac ctc agg cct tgg     192
Tyr Leu Leu Gln Gln Leu Ala Asp Ala Tyr Val Asp Leu Arg Pro Trp
    50                  55                  60 ctg ctg gag atc ggc ttc tcc cct tcc ctg ctc act cag agc aaa gtc     240
Leu Leu Glu Ile Gly Phe Ser Pro Ser Leu Leu Thr Gln Ser Lys Val
65                  70                  75                  80 gtg gtc aac act gac cca gtg agc agg tat acc cag cag ctg cga cac     288
Val Val Asn Thr Asp Pro Val Ser Arg Tyr Thr Gln Gln Leu Arg His
                85                  90                  95
```

```
cat ctg ggc cgt gac tcc aag ttc gtg ctg tgc tat gcc cag aag gag      336
His Leu Gly Arg Asp Ser Lys Phe Val Leu Cys Tyr Ala Gln Lys Glu
            100                 105                 110 gag ctg ctg ctg gag gag atc tac atg gac acc atc atg gag ctg gtt      384
Glu Leu Leu Leu Glu Glu Ile Tyr Met Asp Thr Ile Met Glu Leu Val
                115                 120                 125 ggc ttc agc aat gag agc ctg ggc agc ctg aac agc ctg gcc tgc ctc      432
Gly Phe Ser Asn Glu Ser Leu Gly Ser Leu Asn Ser Leu Ala Cys Leu
130                 135                 140 ctg gac cac acc acc ggc atc ctc aat gag cag ggt gag acc atc ttc      480
Leu Asp His Thr Thr Gly Ile Leu Asn Glu Gln Gly Glu Thr Ile Phe
145                 150                 155                 160 atc ctg ggt gat gct ggg gtg ggc aag tcc atg ctg cta cag cgg ctg      528
Ile Leu Gly Asp Ala Gly Val Gly Lys Ser Met Leu Leu Gln Arg Leu
                165                 170                 175 cag agc ctc tgg gcc acg ggc cgg cta gac gca ggg gtc aaa ttc ttc      576
Gln Ser Leu Trp Ala Thr Gly Arg Leu Asp Ala Gly Val Lys Phe Phe
                180                 185                 190 ttc cac ttt cgc tgc cgc atg ttc agc tgc ttc aag gaa agt gac agg      624
Phe His Phe Arg Cys Arg Met Phe Ser Cys Phe Lys Glu Ser Asp Arg
            195                 200                 205 ctg tgt ctg cag gac ctg ctc ttc aag cac tac tgc tac cca gag cgg      672
Leu Cys Leu Gln Asp Leu Leu Phe Lys His Tyr Cys Tyr Pro Glu Arg
210                 215                 220 gac ccc gag gag gtg ttt gcc ttc ctg ctg cgc ttc ccc cac gtg gcc      720
Asp Pro Glu Glu Val Phe Ala Phe Leu Leu Arg Phe Pro His Val Ala
225                 230                 235                 240 ctc ttc acc ttc gat ggc ctg gac gag ctg cac tcg gac ttg gac ctg      768
Leu Phe Thr Phe Asp Gly Leu Asp Glu Leu His Ser Asp Leu Asp Leu
                245                 250                 255 agc cgc gtg cct gac agc tcc tgc ccc tgg gag cct gcc cac ccc ctg      816
Ser Arg Val Pro Asp Ser Ser Cys Pro Trp Glu Pro Ala His Pro Leu
                260                 265                 270 gtc ttg ctg gcc aac ctg ctc agt ggg aag ctg ctc aag ggg gct agc      864
Val Leu Leu Ala Asn Leu Leu Ser Gly Lys Leu Leu Lys Gly Ala Ser
            275                 280                 285 aag ctg ctc aca gcc cgc aca ggc atc gag gtc ccg cgc cag ttc ctg      912
Lys Leu Leu Thr Ala Arg Thr Gly Ile Glu Val Pro Arg Gln Phe Leu
290                 295                 300 cgg aag aag gtg ctt ctc cgg ggc ttc tcc ccc agc cac ctg cgc gcc      960
Arg Lys Lys Val Leu Leu Arg Gly Phe Ser Pro Ser His Leu Arg Ala
305                 310                 315                 320 tat gcc agg agg atg ttc ccc gag cgg gcc ctg cag gac cgc ctg ctg     1008
Tyr Ala Arg Arg Met Phe Pro Glu Arg Ala Leu Gln Asp Arg Leu Leu
                325                 330                 335 agc cag ctg gag gcc aac ccc aac ctc tgc agc ctg tgc tct gtg ccc     1056
Ser Gln Leu Glu Ala Asn Pro Asn Leu Cys Ser Leu Cys Ser Val Pro
                340                 345                 350 ctc ttc tgc tgg atc atc ttc cgg tgc ttc cag cac ttc cgt gct gcc     1104
Leu Phe Cys Trp Ile Ile Phe Arg Cys Phe Gln His Phe Arg Ala Ala
            355                 360                 365 ttt gaa ggc tca cca cag ctg ccc gac tgc acg atg acc ctg aca gat     1152
Phe Glu Gly Ser Pro Gln Leu Pro Asp Cys Thr Met Thr Leu Thr Asp
370                 375                 380 gtc ttc ctc ctg gtc act gag gtc cat ctg aac agg atg cag ccc agc     1200
Val Phe Leu Leu Val Thr Glu Val His Leu Asn Arg Met Gln Pro Ser
385                 390                 395                 400 agc ctg gtg cag cgg aac aca cgc agc cca gtg gag acc ctc cac gcc     1248
Ser Leu Val Gln Arg Asn Thr Arg Ser Pro Val Glu Thr Leu His Ala
                405                 410                 415
```

```
ggc cgg gac act ctg tgc tcg ctg ggg cag gtg gcc cac cgg ggc atg      1296
Gly Arg Asp Thr Leu Cys Ser Leu Gly Gln Val Ala His Arg Gly Met
            420                 425                 430 gag aag agc ctc ttt gtc ttc acc cag gag gag gtg cag gcc tcc ggg      1344
Glu Lys Ser Leu Phe Val Phe Thr Gln Glu Glu Val Gln Ala Ser Gly
        435                 440                 445 ctg cag gag aga gac atg cag ctg ggc ttc ctg cgg gct ttg ccg gag      1392
Leu Gln Glu Arg Asp Met Gln Leu Gly Phe Leu Arg Ala Leu Pro Glu
    450                 455                 460 ctg ggc ccc ggg ggt gac cag cag tcc tat gag ttt ttc cac ctc agc      1440
Leu Gly Pro Gly Gly Asp Gln Gln Ser Tyr Glu Phe Phe His Leu Ser
465                 470                 475                 480 ctc ctc acc tgt aaa act ggg atc cca gta tagactttgg aaatcagtag        1490
Leu Leu Thr Cys Lys Thr Gly Ile Pro Val
                485                 490 acaccatatg cttcaaaaaa cagggctat taaaatgaca tcaggagcca gaaagtctca     1550
tggctgtgct ttctcttgaa gtttatacaa caaccagatc accgatgtcg gagccagact   1610
gggaaaaaac aaaataacaa gtgaaggagg gaagtatctc gccctggctg tgaagaacag   1670
caaatcaatc tctgaggttg ggatgtgggg caatcaagtt ggggatgaag gagcaaaagc   1730
cttcgcagag gctctgcgga accacccag cttgaccacc ctgagtcttg cgtccaacgg    1790
catctccaca gaaggaggaa agagccttgc gagggccctg cagcagaaca cgtctctaga   1850
aatactgtgg ctgacccaaa atgaactcaa cgatgaagtg gcagagagtt tggcagaaat   1910
gttgaaagtc aaccagacgt taaagcattt atggcttatc cagaatcaga tcacagtctt   1970
ttgtgtcagt gtcttaaagg ggcctgcgca ggcgggacta tcaggagtcc actgcctcca   2030
tgatgcaagc cagcttcctg tgcagaaggt ctggtcggca aactccctaa gtacccgcta   2090
caattctgca gaaaagaat gtgtcttgcg agctgttgta gttacagtaa atacactgtg    2150
aagagacttt attgcctatt ataattattt ttatctgaag ctagaggaat aaagctgtga   2210
gcaaacagag gaggccagcc tcacctcatt ccaacacctg ccatagggac caacgggagc   2270
gagttggtca ccgctctttt cattgaagag ttgaggatgt ggcacaaagt tggtgccaag   2330
cttcttgaat aaaacgtgtt tgatggatta gtattatacc tgaaatattt tcttccttct   2390
cagcactttc ccatgtattg atactggtcc cacttcacag ctggagacac cggagtatgt   2450
gcagtgtggg atttgactcc tccaaggttt tgtggaaagt taatgtcaag gaaggatgc    2510 accacgggct tttaattta atcctggagt ctcactgtct gctggcaaag atagagaatg    2570
ccctcagctc ttagctggtc taagaatgac gatgccttca aaatgctgct tccactcagg   2630
gcttctcctc tgctaggcta ccctcctcta gaaggctgag taccatgggc tacagtgtct   2690
ggccttggga agaagtgatt ctgtccctcc aaagaaatag gcatggctt gcccctgtgg    2750 ccctggcatc caaatggctg cttttgtctc ccttacctcg tgaagagggg aagtctcttc   2810
ctgcctccca agcagctgaa gggtgactaa acgggcgcca agactcaggg gatcggctgg   2870
gaactgggcc agcagagcat gttggacacc ccccaccatg gtgggcttgt ggtggctgct   2930
ccatgagggt gggggtgata ctactagatc acttgtcctc ttgccagctc atttgttaat   2990
aaaatactga aacacaaaa aaaaaaaaaa aaaaaaaaaa aaaaaaaaaa aaaaaaaaaa    3050
aaaaaaaaaa aaaaaaaaa aaaaaaaaa                                      3080
```

<210> SEQ ID NO 26
<211> LENGTH: 490
<212> TYPE: PRT

```
<213> ORGANISM: Homo sapiens

<400> SEQUENCE: 26

His Ala Ser Asp Leu Leu Lys Asn Asp Tyr Phe Ser Ala Glu Asp Ala
  1               5                  10                  15

Glu Ile Val Cys Ala Cys Pro Thr Gln Pro Asp Lys Val Arg Lys Ile
                 20                  25                  30

Leu Asp Leu Val Gln Ser Lys Gly Glu Val Ser Glu Phe Phe Leu
         35                  40                  45

Tyr Leu Leu Gln Gln Leu Ala Asp Ala Tyr Val Asp Leu Arg Pro Trp
 50                      55                  60

Leu Leu Glu Ile Gly Phe Ser Pro Ser Leu Leu Thr Gln Ser Lys Val
 65                  70                      75                  80

Val Val Asn Thr Asp Pro Val Ser Arg Tyr Thr Gln Gln Leu Arg His
                 85                  90                  95

His Leu Gly Arg Asp Ser Lys Phe Val Leu Cys Tyr Ala Gln Lys Glu
                100                 105                 110

Glu Leu Leu Leu Glu Glu Ile Tyr Met Asp Thr Ile Met Glu Leu Val
             115                 120                 125

Gly Phe Ser Asn Glu Ser Leu Gly Ser Leu Asn Ser Leu Ala Cys Leu
130                 135                 140

Leu Asp His Thr Thr Gly Ile Leu Asn Glu Gln Gly Glu Thr Ile Phe
145                 150                 155                 160

Ile Leu Gly Asp Ala Gly Val Gly Lys Ser Met Leu Leu Gln Arg Leu
                165                 170                 175

Gln Ser Leu Trp Ala Thr Gly Arg Leu Asp Ala Gly Val Lys Phe Phe
            180                 185                 190

Phe His Phe Arg Cys Arg Met Phe Ser Cys Phe Lys Glu Ser Asp Arg
            195                 200                 205

Leu Cys Leu Gln Asp Leu Leu Phe Lys His Tyr Cys Tyr Pro Glu Arg
        210                 215                 220

Asp Pro Glu Glu Val Phe Ala Phe Leu Leu Arg Phe Pro His Val Ala
225                 230                 235                 240

Leu Phe Thr Phe Asp Gly Leu Asp Glu Leu His Ser Asp Leu Asp Leu
                245                 250                 255

Ser Arg Val Pro Asp Ser Ser Cys Pro Trp Glu Pro Ala His Pro Leu
                260                 265                 270

Val Leu Leu Ala Asn Leu Leu Ser Gly Lys Leu Leu Lys Gly Ala Ser
            275                 280                 285

Lys Leu Leu Thr Ala Arg Thr Gly Ile Glu Val Pro Arg Gln Phe Leu
290                 295                 300

Arg Lys Lys Val Leu Leu Arg Gly Phe Ser Pro Ser His Leu Arg Ala
305                 310                 315                 320

Tyr Ala Arg Arg Met Phe Pro Glu Arg Ala Leu Gln Asp Arg Leu Leu
                325                 330                 335

Ser Gln Leu Glu Ala Asn Pro Asn Leu Cys Ser Leu Cys Ser Val Pro
            340                 345                 350

Leu Phe Cys Trp Ile Ile Phe Arg Cys Phe Gln His Phe Arg Ala Ala
        355                 360                 365

Phe Glu Gly Ser Pro Gln Leu Pro Asp Cys Thr Met Thr Leu Thr Asp
370                 375                 380

Val Phe Leu Leu Val Thr Glu Val His Leu Asn Arg Met Gln Pro Ser
385                 390                 395                 400
```

```
Ser Leu Val Gln Arg Asn Thr Arg Ser Pro Val Glu Thr Leu His Ala
                405                 410                 415
Gly Arg Asp Thr Leu Cys Ser Leu Gly Gln Val Ala His Arg Gly Met
            420                 425                 430
Glu Lys Ser Leu Phe Val Phe Thr Gln Glu Glu Val Gln Ala Ser Gly
        435                 440                 445
Leu Gln Glu Arg Asp Met Gln Leu Gly Phe Leu Arg Ala Leu Pro Glu
    450                 455                 460
Leu Gly Pro Gly Gly Asp Gln Gln Ser Tyr Glu Phe Phe His Leu Ser
465                 470                 475                 480
Leu Leu Thr Cys Lys Thr Gly Ile Pro Val
                485                 490

<210> SEQ ID NO 27
<211> LENGTH: 1470
<212> TYPE: DNA
<213> ORGANISM: Homo sapiens

<400> SEQUENCE: 27
cacgcgtccg acttgctgaa gaatgactac ttctcggccg aagatgcgga gattgtgtgt      60
gcctgcccca cccagcctga caaggtccgc aaaattctgg acctggtaca gagcaagggc     120
gaggaggtgt ccgagttctt cctctacttg ctccagcaac tcgcagatgc ctacgtggac     180
ctcaggcctt ggctgctgga gatcggcttc tccccttccc tgctcactca gagcaaagtc     240
gtggtcaaca ctgacccagt gagcaggtat acccagcagc tgcgacacca tctgggccgt     300
gactccaagt tcgtgctgtg ctatgcccag aaggaggagc tgctgctgga ggagatctac     360
atggacacca tcatggagct ggttggcttc agcaatgaga gcctgggcag cctgaacagc     420
ctggcctgcc tcctggacca caccaccggc atcctcaatg agcagggtga gaccatcttc     480
atcctgggtg atgctggggt gggcaagtcc atgctgctac agcggctgca gagcctctgg     540
gccacgggcc ggctagacgc agggtcaaa ttcttcttcc actttcgctg ccgcatgttc      600
agctgcttca ggaaagtga caggctgtgt ctgcaggacc tgctcttcaa gcactactgc     660
tacccagagc gggaccccga ggaggtgttt gccttcctgc tgcgcttccc ccacgtggcc     720
ctcttcacct tcgatggcct ggacgagctg cactcggact tggacctgag ccgcgtgcct     780
gacagctcct gccccgggga gcctgcccac ccctggtct tgctggccaa cctgctcagt     840
gggaagctgc tcaaggggc tagcaagctg ctcacagccc gcacaggcat cgaggtcccg     900
cgccagttcc tgcggaagaa ggtgcttctc cggggcttct ccccagcca cctgcgcgcc     960 tatgccagga ggatgttccc cgagcgggcc ctgcaggacc gcctgctgag ccagctggag    1020 gccaaccca acctctgcag cctgtgctct gtgccctct tctgctggat catcttccgg     1080
tgcttccagc acttccgtgc tgcctttgaa ggctcaccac agctgcccga ctgcacgatg    1140
accctgacag atgtcttcct cctggtcact gaggtccatc tgaacaggat gcagcccagc    1200
agcctggtgc agcggaacac acgcagccca gtggagaccc tccacgccgg ccgggacact    1260
ctgtgctcgc tggggcaggt ggcccaccgg ggcatggaga gagcctctt tgtcttcacc    1320 caggaggagg tgcaggcctc cgggctgcag gagagagaca tgcagctggg cttcctgcgg    1380
gctttgccgg agctgggccc cggggtgac cagcagtcct atgagttttt ccacctcagc    1440
ctcctcacct gtaaaactgg gatcccagta                                     1470

<210> SEQ ID NO 28
<211> LENGTH: 74
```

```
<212> TYPE: PRT
<213> ORGANISM: Homo sapiens

<400> SEQUENCE: 28

His Ala Ser Asp Leu Leu Lys Asn Asp Tyr Phe Ser Ala Glu Asp Ala
1               5                   10                  15

Glu Ile Val Cys Ala Cys Pro Thr Gln Pro Asp Lys Val Arg Lys Ile
            20                  25                  30

Leu Asp Leu Val Gln Ser Lys Gly Glu Glu Val Ser Glu Phe Phe Leu
        35                  40                  45

Tyr Leu Leu Gln Gln Leu Ala Asp Ala Tyr Val Asp Leu Arg Pro Trp
    50                  55                  60

Leu Leu Glu Ile Gly Phe Ser Pro Ser Leu
65                  70

<210> SEQ ID NO 29
<211> LENGTH: 8
<212> TYPE: PRT
<213> ORGANISM: Homo sapiens

<400> SEQUENCE: 29

Gly Asp Ala Gly Val Gly Lys Ser
1               5

<210> SEQ ID NO 30
<211> LENGTH: 5
<212> TYPE: PRT
<213> ORGANISM: Homo sapiens

<400> SEQUENCE: 30

Leu Phe Thr Phe Asp
1               5

<210> SEQ ID NO 31
<211> LENGTH: 94
<212> TYPE: PRT
<213> ORGANISM: Homo sapiens

<400> SEQUENCE: 31

Ala Gln Glu Arg Pro Ser Glu Thr Thr Asp Arg Glu Arg Lys Arg Leu
1               5                   10                  15

Val Glu Thr Leu Gln Ala Asp Ser Gly Leu Leu Leu Asp Ala Leu Leu
            20                  25                  30

Ala Arg Gly Val Leu Thr Gly Pro Glu Tyr Glu Ala Leu Asp Ala Leu
        35                  40                  45

Pro Asp Ala Glu Arg Arg Val Arg Arg Leu Leu Leu Val Gln Gly
    50                  55                  60

Lys Gly Glu Ala Ala Cys Gln Glu Leu Leu Arg Cys Ala Gln Arg Thr
65                  70                  75                  80

Ala Gly Ala Pro Asp Pro Ala Trp Asp Trp Gln His Val Gly
                    85                  90

<210> SEQ ID NO 32
<211> LENGTH: 89
<212> TYPE: PRT
<213> ORGANISM: Homo sapiens

<400> SEQUENCE: 32

Met Ala Ser Asp Asp Leu Ser Leu Ile Arg Lys Asn Arg Met Ala Leu
1               5                   10                  15
```

Phe Gln Gln Leu Thr Cys Val Leu Pro Ile Leu Asp Asn Leu Leu Lys
            20                  25                  30

Ala Asn Val Thr Asn Lys Gln Glu His Asp Ile Ile Lys Gln Lys Thr
         35                  40                  45

Gln Ile Pro Leu Gln Ala Arg Glu Leu Ile Asp Thr Ile Trp Val Lys
     50                  55                  60

Gly Asn Ala Ala Ala Asn Ile Phe Lys Asn Cys Leu Lys Glu Ile Asp
 65                  70                  75                  80

Ser Thr Leu Tyr Lys Asn Leu Phe Val
             85

<210> SEQ ID NO 33
<211> LENGTH: 89
<212> TYPE: PRT
<213> ORGANISM: Homo sapiens

<400> SEQUENCE: 33

Lys Glu Ser Asn Asp Leu Leu Ile Arg Lys Asn Arg Met Ala Leu
 1               5                  10                  15

Phe Gln His Leu Thr Cys Val Ile Pro Ile Leu Asp Ser Leu Leu Thr
            20                  25                  30

Ala Gly Ile Ile Asn Glu Gln Glu His Asp Val Ile Lys Gln Lys Thr
         35                  40                  45

Gln Thr Ser Leu Gln Ala Arg Glu Leu Ile Asp Thr Ile Leu Val Lys
     50                  55                  60

Gly Asn Ile Ala Ala Thr Val Phe Arg Asn Ser Leu Gln Glu Ala Glu
 65                  70                  75                  80

Ala Val Leu Tyr Glu His Leu Phe Val
             85

<210> SEQ ID NO 34
<211> LENGTH: 24
<212> TYPE: DNA
<213> ORGANISM: Homo sapiens

<400> SEQUENCE: 34
ccctggtact tgcccctccg gtag                                      24

<210> SEQ ID NO 35
<211> LENGTH: 18
<212> TYPE: DNA
<213> ORGANISM: Homo sapiens

<400> SEQUENCE: 35
cctggtactt gcccctcc                                             18

<210> SEQ ID NO 36
<211> LENGTH: 23
<212> TYPE: DNA
<213> ORGANISM: Homo sapiens

<400> SEQUENCE: 36
tcgttaagcc cttgaagaca gtg                                       23

<210> SEQ ID NO 37
<211> LENGTH: 30
<212> TYPE: DNA
<213> ORGANISM: Homo sapiens

<400> SEQUENCE: 37

-continued

```
tcgttagccc ttgaagacca gtgagtgtag                                              30

<210> SEQ ID NO 38
<211> LENGTH: 4302
<212> TYPE: DNA
<213> ORGANISM: Homo sapiens
<220> FEATURE:
<221> NAME/KEY: CDS
<222> LOCATION: (438)...(1184)
<221> NAME/KEY: misc_feature
<222> LOCATION: (1)...(4302)
<223> OTHER INFORMATION: n = A,T,C or G

<400> SEQUENCE: 38
cccgcgtccg cgtccccgga ccatggcgct ctccgggctc ttctctagct ctcagcggct           60
gcgaagtctg tnaacctggt ggccaagtga ttgtaagtca ggagactttc cttcggtttc          120
tgcctttgat ggcaagaggt ggagattgtg gcggcgatta cagaaaacat ctgggaagac          180
aagttgctgt ttttatggga atcgcaggct tggaagagac agaagcaatt ccagaaataa          240
attggaaatt gaagatttaa acaatgttgt tttaaaatat tctaacttca agaatgatg           300 ccagaaactt aaaaggggc tgcgcagagt agcagggggcc ctggagggcg cggcctgaat          360
cctgattgcc cttctgctga gaggacacac gcagctgaag atgaatttgg gaaaagtagc          420
cgcttgctac tttaact atg gaa gag cag ggc cac agt gag atg gaa ata             470
                 Met Glu Glu Gln Gly His Ser Glu Met Glu Ile
                   1               5                  10 atc cca tca gag tct cac ccc cac att caa tta ctg aaa agc aat cgg           518
Ile Pro Ser Glu Ser His Pro His Ile Gln Leu Leu Lys Ser Asn Arg
        15                  20                  25 gaa ctt ctg gtc act cac atc cgc aat act cag tgt ctg gtg gac aac           566
Glu Leu Leu Val Thr His Ile Arg Asn Thr Gln Cys Leu Val Asp Asn
            30                  35                  40 ttg ctg aag aat gac tac ttc tcg gcc gaa gat gcg gag att gtg tgt           614
Leu Leu Lys Asn Asp Tyr Phe Ser Ala Glu Asp Ala Glu Ile Val Cys
        45                  50                  55 gcc tgc ccc acc cag cct gac aag gtc cgc aaa att ctg gac ctg gta           662
Ala Cys Pro Thr Gln Pro Asp Lys Val Arg Lys Ile Leu Asp Leu Val
60                  65                  70                  75 cag agc aag ggc gag gag gtg tcc gag ttc ttc ctc tac ttg ctc cag           710
Gln Ser Lys Gly Glu Glu Val Ser Glu Phe Phe Leu Tyr Leu Leu Gln
                80                  85                  90 caa ctc gca gat gcc tac gtg gac ctc agg cct tgg ctg ctg gag atc           758
Gln Leu Ala Asp Ala Tyr Val Asp Leu Arg Pro Trp Leu Leu Glu Ile
            95                 100                 105 ggc ttc tcc cct tcc ctg ctc act cag agc aaa gtc gtg gtc aac act           806
Gly Phe Ser Pro Ser Leu Leu Thr Gln Ser Lys Val Val Val Asn Thr
        110                 115                 120 gac cca gtg agc agg tat acc cag cag ctg cga cac cat ctg ggc cgt           854
Asp Pro Val Ser Arg Tyr Thr Gln Gln Leu Arg His His Leu Gly Arg
125                 130                 135 gac tcc aag ttc gtg ctg tgc tat gcc cag aag gag gag ctg ctg ctg           902
Asp Ser Lys Phe Val Leu Cys Tyr Ala Gln Lys Glu Glu Leu Leu Leu
140                 145                 150                 155 gag gag atc tac atg gac acc atc atg gag ctg gtt ggc ttc agc aat           950
Glu Glu Ile Tyr Met Asp Thr Ile Met Glu Leu Val Gly Phe Ser Asn
                160                 165                 170 gag agc ctg ggc agc ctg aac agc ctg gcc tgc ctc ctg gac cac acc           998
Glu Ser Leu Gly Ser Leu Asn Ser Leu Ala Cys Leu Leu Asp His Thr
            175                 180                 185 acc ggc atc ctc aat gag cag gct gct tca agg aaa gtg aca ggc tgt          1046
```

-continued

```
Thr Gly Ile Leu Asn Glu Gln Ala Ala Ser Arg Lys Val Thr Gly Cys
    190                 195                 200 gtc tgc agg acc tgc tct tca agc act act gct acc cag agc ggg acc      1094
Val Cys Arg Thr Cys Ser Ser Ser Thr Thr Ala Thr Gln Ser Gly Thr
    205                 210                 215 ccg agg agg tgt ttg cct tcc tgc tgc gct tcc ccc acg tgg ccc tct      1142
Pro Arg Arg Cys Leu Pro Ser Cys Cys Ala Ser Pro Thr Trp Pro Ser
220                 225                 230                 235 tca cct tcg atg gcc tgg acg agc tgc act cgg act tgg acc              1184
Ser Pro Ser Met Ala Trp Thr Ser Cys Thr Arg Thr Trp Thr
                240                 245 tgagccgcgt gcctgacagc tcctgcccct gggagcctgc ccaccccctg gtcttgctgg    1244
ccaacctgct cagtgggaag ctgctcaagg gggctagcaa gctgctcaca gcccgcacag    1304
gcatcgaggt cccgcgccag ttcctgcgga agaaggtgct tctccggggc ttctccccca    1364
gccacctgcg cgcctatgcc aggaggatgt tccccgagcg ggccctgcag gaccgcctgc    1424
tgagccagct ggaggccaac cccaacctct gcagcctgtg ctctgtgccc ctcttctgct    1484
ggatcatctt ccggtgcttc cagcacttcc gtgctgcctt tgaaggctca ccacagctgc    1544
ccgactgcac gatgaccctg acagatgtct tcctcctggt cactgaggtc catctgaaca    1604
ggatgcagcc cagcagcctg gtgcagcgga acacgcag cccagtggag accctccacg     1664
ccggccggga cactctgtgc tcgctgggc aggtggccca ccggggcatg gagaagagcc     1724
tctttgtctt cacccaggag gaggtgcagg cctccgggct gcaggagaga cacatgcagc    1784
tgggcttcct gcgggctttg ccggagctgg gccccggggg tgaccagcag tcctatgagt    1844
ttttccacct caccctccag gccttcttta cagccttctt cctcgtgctg acgacaggg    1904 tgggcactca ggagctgctc aggttcttcc aggagtggat gccccctgcg ggggcagcga    1964
ccacgtcctg ctatcctccc ttcctcccgt tccagtgcct gcagggcagt ggtccggcgc    2024
gggaagacct cttcaagaac aaggatcact tccagttcac caacctcttc ctgtgcgggc    2084
tgttgkccaa agccaaacag aaactcctgc ggcatctggt gccgcggca gccctgagga    2144 gaaagcgcaa ggccctgtgg gcacacctgt tttccagcct gcggggctac ctgaagagcc    2204
tgccccgcgt tcaggtcgaa agcttcaacc aggtgcaggc catgcccacg ttcatctgga    2264
tgctgcgctg catctacgag acacagagcc agaaggtggg gcagctggcg gccaggggca    2324
tctgcgccaa ctacctcaag ctgacctact gcaacgcctg ctcggccgac tgcagcgccc    2384
tctccttcgt cctgcatcac ttccccaagc ggctggccct agacctagac aacaacaatc    2444
tcaacgacta cggcgtgcgg gagctgcagc cctgcttcag ccgcctcact gttctcagac    2504
tcagcgtaaa ccagatcact gacggtgggg taaaggtgct aagcgaagag ctgaccaaat    2564
acaaaattgt gacctatttg ggtttataca acaaccagat caccgatgtc ggagccaggt    2624
acgtcaccaa aatcctggat gaatgcaaag gcctcacgca tcttaaactg ggaaaaaaca    2684
aaataacaag tgaaggaggg aagtatctcg ccctggctgt gaagaacagc aaatcaatct    2744
ctgaggttgg gatgtgggc aatcaagttg gggatgaagg agcaaaagcc ttcgcagagg     2804
ctctgcggaa ccaccccagc ttgaccaccc tgagtcttgc gtccaacggc atctccacag    2864
aaggaggaaa gagccttgcg agggccctgc agcagaacac gtctctagaa atactgtggc    2924
tgacccaaaa tgaactcaac gatgaagtgg cagagagttt ggcagaaatg ttgaaagtca    2984
accagacgtt aaagcattta tggcttatcc agaatcasat cacagctwar gggactgccc    3044
agctggcaga tgcgttacag agcaacactg gcataacaga gatttgccta aatggaaacc    3104
```

```
tgataaaacc agaggaggcc aaagtctatg aagatgagaa gcggattatc tgtttctgag    3164
aggatgcttt cctgttcatg gggttttttgc cctggagcct cagcagcaaa tgccactytg   3224
ggcagtcttt tgtgtcagtg tcttaaaggg gcctgcgcag gcgggactat caggagtcca    3284
ctgcctccat gatgcaagcc agcttcctgt gcagaaggtc tggtcggcaa actccctaag    3344
tacccgctac aattctgcag aaaaagaatg tgtcttgcga gctgttgtag ttacagtaaa    3404
tacactgtga agagacttta ttgcctatta taattatttt tatctgaagc tagaggaata    3464
aagctgtgag caaacagagg aggccagcct caccctcattc caacacctgc cataggggacc  3524 aacgggagcg agttggtcac cgctcttttc attgaagagt tgaggatgtg cacaaagtt    3584 ggtgccaagc ttcttgaata aaacgtgttt gatggattag tattatacct gaaatatttt    3644
cttccttctc agcactttcc catgtattga tactggtccc acttcacagc tggagacacc    3704
ggagtatgtg cagtgtggga tttgactcct ccaaggtttt gtggaaagtt aatgtcaagg    3764
aaaggatgca ccacgggctt ttaatttttaa tcctggagtc tcactgtctg ctggcaaaga   3824
tagagaatgc cctcagctct tagctggtct aagaatgacg atgccttcaa aatgctgctt    3884
ccactcaggg cttctcctct gctaggctac cctcctctag aaggctgagt accatgggct    3944
acagtgtctg gccttgggaa gaagtgattc tgtccctcca aagaaatagg gcatggcttg    4004
cccctgtggc cctggcatcc aaatggctgc ttttgtctcc cttacctcgt gaagagggga    4064
agtctcttcc tgcctcccaa gcagctgaag ggtgactaaa cgggcgccaa gactcagggg    4124
atcggctggg aactgggcca gcagagcatg ttggacaccc cccaccatgg tgggcttgtg    4184
gtggctgctc catgagggtg gggtgatac tactagatca cttgtcctct tgccagctca    4244
tttgttaata aaatactgaa aacccaaaaa aaaaaaaaa aaaaaaaaaa aagggcgg      4302
```

<210> SEQ ID NO 39
<211> LENGTH: 249
<212> TYPE: PRT
<213> ORGANISM: Homo sapiens

<400> SEQUENCE: 39

```
Met Glu Glu Gln Gly His Ser Glu Met Glu Ile Ile Pro Ser Glu Ser
 1               5                  10                  15

His Pro His Ile Gln Leu Leu Lys Ser Asn Arg Glu Leu Leu Val Thr
            20                  25                  30

His Ile Arg Asn Thr Gln Cys Leu Val Asp Asn Leu Leu Lys Asn Asp
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Leu Leu Gln Gln Leu Ala Asp Ala
                85                  90                  95

Tyr Val Asp Leu Arg Pro Trp Leu Leu Glu Ile Gly Phe Ser Pro Ser
            100                 105                 110

Leu Leu Thr Gln Ser Lys Val Val Asn Thr Asp Pro Val Ser Arg
        115                 120                 125

Tyr Thr Gln Gln Leu Arg His His Leu Gly Arg Asp Ser Lys Phe Val
    130                 135                 140

Leu Cys Tyr Ala Gln Lys Glu Leu Leu Glu Glu Ile Tyr Met
145                 150                 155                 160

Asp Thr Ile Met Glu Leu Val Gly Phe Ser Asn Glu Ser Leu Gly Ser
```

-continued

```
                  165                 170                 175
Leu Asn Ser Leu Ala Cys Leu Leu Asp His Thr Thr Gly Ile Leu Asn
                180                 185                 190

Glu Gln Ala Ala Ser Arg Lys Val Thr Gly Cys Val Cys Arg Thr Cys
            195                 200                 205

Ser Ser Ser Thr Thr Ala Thr Gln Ser Gly Thr Pro Arg Arg Cys Leu
        210                 215                 220

Pro Ser Cys Cys Ala Ser Pro Thr Trp Pro Ser Ser Pro Ser Met Ala
225                 230                 235                 240

Trp Thr Ser Cys Thr Arg Thr Trp Thr
                245
```

<210> SEQ ID NO 40
<211> LENGTH: 1400
<212> TYPE: DNA
<213> ORGANISM: Homo sapiens
<220> FEATURE:
<221> NAME/KEY: CDS
<222> LOCATION: (489)...(980)
<221> NAME/KEY: misc_feature
<222> LOCATION: (1)...(1400)
<223> OTHER INFORMATION: n = A,T,C or G

<400> SEQUENCE: 40

```
cacgcgtccg cgctactgcg ggagcagcgt cctcccgggc cacggcgctt cccggccccg     60
gcgtccccgg accatggcgc tctccgggct cttctctagc tctcagcggc tgcgaagtct    120
gtaaacctgg tggccaagtg attgtaagtc aggagacttt ccttcggttt ctgcctttga    180
tggcaagagg tggagattgt ggcggcgatt acagaaaaca tctgggaaga caagttgctg    240
tttttatggg aatcgcaggc ttggaagaga cagaagcaat tccagaaata aattggaaat    300
tgaagattta acaatgttg ttttaaaata ttctaacttc aaagaatgat gccagaaact    360 taaaagggg ctgcgcagag tagcagggc cctggagggc gcggcctgaa tcctgattgc    420
ccttctgctg agaggacaca cgcagctgaa gatgaatttg ggaaaagtag ccgcttgcta    480 ctttaact atg gaa gag cag ggc cac agt gag atg gaa ata atc cca tca     530
         Met Glu Glu Gln Gly His Ser Glu Met Glu Ile Ile Pro Ser
             1               5                  10 gag tct cac ccc cac att caa tta ctg aaa agc aat cgg gaa ctt ctg      578
Glu Ser His Pro His Ile Gln Leu Leu Lys Ser Asn Arg Glu Leu Leu
 15              20                  25                  30 gtc act cac atc cgc aat act cag tgt ctg gtg gac aac ttg ctg aag      626
Val Thr His Ile Arg Asn Thr Gln Cys Leu Val Asp Asn Leu Leu Lys
                 35                  40                  45 aat gac tac ttc tcg gcc gaa gat gcg gag att gtg tgt gcc tgc ccc      674
Asn Asp Tyr Phe Ser Ala Glu Asp Ala Glu Ile Val Cys Ala Cys Pro
             50                  55                  60 acc cag cct gac aag gtc cgc aaa att ctg gac ctg gta cag agc aag      722
Thr Gln Pro Asp Lys Val Arg Lys Ile Leu Asp Leu Val Gln Ser Lys
         65                  70                  75 ggc gag gag gtg tcc gag ttc ttc ctc tac ttg ctc cag caa ctc gca      770
Gly Glu Glu Val Ser Glu Phe Phe Leu Tyr Leu Leu Gln Gln Leu Ala
     80                  85                  90 gat gcc tac gtg gac ctc agg cct tgg ctg ctg gag atc ggc ttc tcc      818
Asp Ala Tyr Val Asp Leu Arg Pro Trp Leu Leu Glu Ile Gly Phe Ser
 95                 100                 105                 110 cct tcc ctg ctc act cag agc aaa gtc gtg gtc aac act gac cca ggt      866
Pro Ser Leu Leu Thr Gln Ser Lys Val Val Val Asn Thr Asp Pro Gly
                115                 120                 125
```

```
agg agt cag ccc cag caa gac cgc agg cac cag tgc aag cag ggc cct    914
Arg Ser Gln Pro Gln Gln Asp Arg Arg His Gln Cys Lys Gln Gly Pro
        130                 135                 140 ggg ggg ttt ggt aat ggc tgg gcc agc cct gag tgc cac ctc agg aag    962
Gly Gly Phe Gly Asn Gly Trp Ala Ser Pro Glu Cys His Leu Arg Lys
            145                 150                 155 cag gcc cag gtg cta ttt tgattttaga aggaacagc tgaatcctgt           1010
Gln Ala Gln Val Leu Phe
        160 ctcccaagtg cagcccaggt ggctgcgatt gaactgccca cacctcgatg gtctggttta 1070 tagaggggcc tttggaagta tgggaatggc ctgtgttctg accccttgct tcttcctat  1130 tctgacatat gtagacattt taatggttgc acaaattcaa ggttgtattt ttttttcttt 1190 aaaaaaatct ttagctggac atggtagcac acacctgtag ttccagctac tcaggaggct 1250 gaggcaagag gactgcttga gccccagagt ctaaggctgc agcgagctat gattgtgccc  1310 ctacactcca cagcctgggt tttagagtga gaccctgtct ctaaaaaaaa aaaaaaaaaa 1370 aaaaaaaaaa aaaaaaaaaa aaangggcgg                                  1400

<210> SEQ ID NO 41
<211> LENGTH: 164
<212> TYPE: PRT
<213> ORGANISM: Homo sapiens

<400> SEQUENCE: 41

Met Glu Glu Gln Gly His Ser Glu Met Glu Ile Ile Pro Ser Glu Ser
 1               5                  10                  15

His Pro His Ile Gln Leu Leu Lys Ser Asn Arg Glu Leu Leu Val Thr
            20                  25                  30

His Ile Arg Asn Thr Gln Cys Leu Val Asp Asn Leu Leu Lys Asn Asp
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Leu Leu Gln Gln Leu Ala Asp Ala
                85                  90                  95

Tyr Val Asp Leu Arg Pro Trp Leu Leu Glu Ile Gly Phe Ser Pro Ser
            100                 105                 110

Leu Leu Thr Gln Ser Lys Val Val Asn Thr Asp Pro Gly Arg Ser
        115                 120                 125

Gln Pro Gln Gln Asp Arg Arg His Gln Cys Lys Gln Pro Gly Gly
    130                 135                 140

Phe Gly Asn Gly Trp Ala Ser Pro Glu Cys His Leu Arg Lys Gln Ala
145                 150                 155                 160

Gln Val Leu Phe

<210> SEQ ID NO 42
<211> LENGTH: 4141
<212> TYPE: DNA
<213> ORGANISM: Mus musculus
<220> FEATURE:
<221> NAME/KEY: CDS
<222> LOCATION: (261)...(3119)

<400> SEQUENCE: 42
ccacgcgtcc gcggaccgcg agcggtagcg ccctccctcc cagctgttgt cccgcccgat    60
```

-continued

```
ccgcgaccct agtccccgga tccccttgct gagagtcacc gtactccagg gccaactgag      120
ccaaagtcct gccaacttgg gtcagcaatg aaaggcagga tcctgggtgg tggccctgaa      180
tcctgatttg tctgccctgc cagcgagaca catgtggtca agatgaatt tgagaaaagt       240 agctgctggc tacttgaaca atg gag gaa cac ggc cat cat gag atg gaa ggc     293
              Met Glu Glu His Gly His His Glu Met Glu Gly
                1              5               10 acc cca ttg ggt tgt cac tcc cac att aaa ctg ctg aag atc aac agg        341
Thr Pro Leu Gly Cys His Ser His Ile Lys Leu Leu Lys Ile Asn Arg
             15              20              25 gaa cat ctg gtc acc aac att cgg aac act cag tgt ctg gtg gac aac        389
Glu His Leu Val Thr Asn Ile Arg Asn Thr Gln Cys Leu Val Asp Asn
         30              35              40 ttg ctg gag aat ggc tac ttc tca gcc gaa gat gca gag att gtg tgt        437
Leu Leu Glu Asn Gly Tyr Phe Ser Ala Glu Asp Ala Glu Ile Val Cys
     45              50              55 gcc tgt ccc acc aag cct gac aag gtc cga aag atc ctt gac ctg gtg        485
Ala Cys Pro Thr Lys Pro Asp Lys Val Arg Lys Ile Leu Asp Leu Val
 60              65              70              75 cag agc aaa ggc gag gag gtg tct gag ttc ttc ctc tac gtg ctg cag        533
Gln Ser Lys Gly Glu Glu Val Ser Glu Phe Phe Leu Tyr Val Leu Gln
             80              85              90 cag ctg gag gat gct tac gtg gac ctc agg ctg tgg ctc tca gaa att        581
Gln Leu Glu Asp Ala Tyr Val Asp Leu Arg Leu Trp Leu Ser Glu Ile
         95              100             105 ggc ttc tcc cct tcc cag ctc att cgg acc aaa act atc gtc aat act        629
Gly Phe Ser Pro Ser Gln Leu Ile Arg Thr Lys Thr Ile Val Asn Thr
     110             115             120 gac cca gta agc agg tat acc caa cag ctg cga cac caa ctg ggc cgc        677
Asp Pro Val Ser Arg Tyr Thr Gln Gln Leu Arg His Gln Leu Gly Arg
     125             130             135 gac tcc aag ttc atg ctg tgc tac gcc cag aag gag gac ctg ctg ctg        725
Asp Ser Lys Phe Met Leu Cys Tyr Ala Gln Lys Glu Asp Leu Leu Leu
140             145             150             155 gag gag acc tat atg gac aca ctc atg ggg ctg gta ggc ttc aac aat        773
Glu Glu Thr Tyr Met Asp Thr Leu Met Gly Leu Val Gly Phe Asn Asn
             160             165             170 gaa aac ctg ggc agc cta gga ggc ctg gat tgc ctg ctg gac cac agt        821
Glu Asn Leu Gly Ser Leu Gly Gly Leu Asp Cys Leu Leu Asp His Ser
         175             180             185 acg ggc gtc ctc aac gag cat ggc gag act gtc ttc gtg ttc ggg gac        869
Thr Gly Val Leu Asn Glu His Gly Glu Thr Val Phe Val Phe Gly Asp
     190             195             200 gcg gga gtg ggc aag tcc atg ctg ctg cag agg ttg cag agc ctc tgg        917
Ala Gly Val Gly Lys Ser Met Leu Leu Gln Arg Leu Gln Ser Leu Trp
 205             210             215 gcg tca ggc agg ttg acc tcc aca gcc aaa ttc ttc ttc cac ttc cgc        965
Ala Ser Gly Arg Leu Thr Ser Thr Ala Lys Phe Phe Phe His Phe Arg
220             225             230             235 tgc cgc atg ttc agc tgc ttc aag gag agc gac atg ctg agt ctg cag       1013
Cys Arg Met Phe Ser Cys Phe Lys Glu Ser Asp Met Leu Ser Leu Gln
             240             245             250 gac ctg ctc ttc aag cat ttc tgc tac ccg gag cag gac ccc gag gag       1061
Asp Leu Leu Phe Lys His Phe Cys Tyr Pro Glu Gln Asp Pro Glu Glu
         255             260             265 gtg ttc tcc ttc ttg ctg cgc ttt ccc cac aca gcg ctc ttc act ttt       1109
Val Phe Ser Phe Leu Leu Arg Phe Pro His Thr Ala Leu Phe Thr Phe
     270             275             280 gac ggc ctg gat gag ctg cac tca gac ttc gac ctg agc cgc gtg ccg       1157
```

```
Asp Gly Leu Asp Glu Leu His Ser Asp Phe Asp Leu Ser Arg Val Pro
    285                 290                 295 gat agc tgc tgc ccc tgg gag ccg gct cac cct ctg gtc ctg ctg gct    1205
Asp Ser Cys Cys Pro Trp Glu Pro Ala His Pro Leu Val Leu Leu Ala
300                 305                 310                 315 aac ctc cta agt ggg agg ctg ctc aag ggt gcc ggc aaa ttg ctc act    1253
Asn Leu Leu Ser Gly Arg Leu Leu Lys Gly Ala Gly Lys Leu Leu Thr
                320                 325                 330 gct cgc aca ggc gtg gag gtc ccc cgc cag ctc ctg cgc aaa aag gtg    1301
Ala Arg Thr Gly Val Glu Val Pro Arg Gln Leu Leu Arg Lys Lys Val
            335                 340                 345 ctg ctc cgg ggc ttc tcc cca agt cac ctg cgc gcc tat gcc cgc cgg    1349
Leu Leu Arg Gly Phe Ser Pro Ser His Leu Arg Ala Tyr Ala Arg Arg
        350                 355                 360 atg ttc ccc gag cgc aca gcg cag gag cat ctg ctg cag cag ctg gat    1397
Met Phe Pro Glu Arg Thr Ala Gln Glu His Leu Leu Gln Gln Leu Asp
365                 370                 375 gcc aac ccc aac ctc tgc agc ctg tgc ggg gtg ccg ctc ttc tgt tgg    1445
Ala Asn Pro Asn Leu Cys Ser Leu Cys Gly Val Pro Leu Phe Cys Trp
380                 385                 390                 395 atc atc ttc cgt tgt ttc cag cac ttc cag acg gtc ttc gag ggc tcc    1493
Ile Ile Phe Arg Cys Phe Gln His Phe Gln Thr Val Phe Glu Gly Ser
                400                 405                 410 tct tca cag ttg ccg gac tgt gct gtg acc ctg acc gat gtc ttt ctg    1541
Ser Ser Gln Leu Pro Asp Cys Ala Val Thr Leu Thr Asp Val Phe Leu
            415                 420                 425 ctg gtc act gag gtg cat ctg aac agg ccg cag ccc agc agc ctg gtg    1589
Leu Val Thr Glu Val His Leu Asn Arg Pro Gln Pro Ser Ser Leu Val
        430                 435                 440 cag cgc aac acg cgc agc ccg gcg gaa acc cta cgt gca ggc tgg cgc    1637
Gln Arg Asn Thr Arg Ser Pro Ala Glu Thr Leu Arg Ala Gly Trp Arg
    445                 450                 455 acg ctg cat gcg ctg gga gag gtg gct cac cga ggc acc gac aag agc    1685
Thr Leu His Ala Leu Gly Glu Val Ala His Arg Gly Thr Asp Lys Ser
460                 465                 470                 475 ctc ttt gtg ttt ggc cag gag gag gtg cag gcg tcg aag ctg cag gaa    1733
Leu Phe Val Phe Gly Gln Glu Glu Val Gln Ala Ser Lys Leu Gln Glu
                480                 485                 490 gga gat ctg cag ctg ggc ttc ctg cgg gct ttg ccc gat gtg ggc cct    1781
Gly Asp Leu Gln Leu Gly Phe Leu Arg Ala Leu Pro Asp Val Gly Pro
            495                 500                 505 gag cag ggc cag tct tac gaa ttt ttc cac ctt acg ctc cag gcc ttc    1829
Glu Gln Gly Gln Ser Tyr Glu Phe Phe His Leu Thr Leu Gln Ala Phe
        510                 515                 520 ttc acc gcc ttc ttc ctg gta gca gat gac aaa gtg agc acc cgg gag    1877
Phe Thr Ala Phe Phe Leu Val Ala Asp Asp Lys Val Ser Thr Arg Glu
    525                 530                 535 ttg ctg agg ttc ttt cga gaa tgg acg tct cct gga gag gca aca agc    1925
Leu Leu Arg Phe Phe Arg Glu Trp Thr Ser Pro Gly Glu Ala Thr Ser
540                 545                 550                 555 tcg tcc tgc cat tct tcc ttc ttc tcc ttc cag tgc ctg ggc ggc aga    1973
Ser Ser Cys His Ser Ser Phe Phe Ser Phe Gln Cys Leu Gly Gly Arg
                560                 565                 570 agc cgg ttg ggc cct gat cct ttc agg aac aaa gat cac ttc cag ttc    2021
Ser Arg Leu Gly Pro Asp Pro Phe Arg Asn Lys Asp His Phe Gln Phe
            575                 580                 585 acc aac ctc ttc gtg tgc ggg cta ctg gcc aaa gcc cga cag aaa ctc    2069
Thr Asn Leu Phe Val Cys Gly Leu Leu Ala Lys Ala Arg Gln Lys Leu
        590                 595                 600
```

```
ctt cgg cag ctg gtg ccc aag gct atc ctg agg agg aag cgc aag gcc     2117
Leu Arg Gln Leu Val Pro Lys Ala Ile Leu Arg Arg Lys Arg Lys Ala
        605                 610                 615 ctg tgg gct cac ctg ttt gct agc ctg cgc tcc tac ttg aag agc cta     2165
Leu Trp Ala His Leu Phe Ala Ser Leu Arg Ser Tyr Leu Lys Ser Leu
620                 625                 630                 635 cct cgg gtc cag tct gga ggc ttt aac cag gtg cat gcc atg ccc aca     2213
Pro Arg Val Gln Ser Gly Gly Phe Asn Gln Val His Ala Met Pro Thr
                640                 645                 650 ttc ctg tgg atg ctg cgc tgc atc tat gag acg cag agc cag aag gtg     2261
Phe Leu Trp Met Leu Arg Cys Ile Tyr Glu Thr Gln Ser Gln Lys Val
        655                 660                 665 ggg cgc ctc gcc gcc agg ggc atc agt gcg gac tac ctc aag ctg gcc     2309
Gly Arg Leu Ala Ala Arg Gly Ile Ser Ala Asp Tyr Leu Lys Leu Ala
            670                 675                 680 ttt tgc aac gct tgc tct gcg gac tgc agc gcc ctg tcc ttc gtc ctg     2357
Phe Cys Asn Ala Cys Ser Ala Asp Cys Ser Ala Leu Ser Phe Val Leu
        685                 690                 695 cat cac ttc cac agg cag ctg gcc cta gac ctg gac aac aac aac ctc     2405
His His Phe His Arg Gln Leu Ala Leu Asp Leu Asp Asn Asn Asn Leu
700                 705                 710                 715 aat gac tat ggc gtg cag gag ctg cag cct tgc ttt agc cgt ctc acg     2453
Asn Asp Tyr Gly Val Gln Glu Leu Gln Pro Cys Phe Ser Arg Leu Thr
                720                 725                 730 gtt atc aga ctc agc gtc aac cag atc acc gac acg ggg gtg aag gtg     2501
Val Ile Arg Leu Ser Val Asn Gln Ile Thr Asp Thr Gly Val Lys Val
        735                 740                 745 cta tgt gag gaa ctg acc aag tat aag atc gtg acg ttc ctg ggt tta     2549
Leu Cys Glu Glu Leu Thr Lys Tyr Lys Ile Val Thr Phe Leu Gly Leu
            750                 755                 760 tac aac aac cag ata act gat atc gga gcc agg tat gtg gcc caa atc     2597
Tyr Asn Asn Gln Ile Thr Asp Ile Gly Ala Arg Tyr Val Ala Gln Ile
        765                 770                 775 ctg gat gaa tgc aga ggc ctc aag cac ctt aaa cta ggg aaa aac aga     2645
Leu Asp Glu Cys Arg Gly Leu Lys His Leu Lys Leu Gly Lys Asn Arg
780                 785                 790                 795 ata aca agt gag ggc ggg aag tgt gtg gct ttg gct gtg aag aac agc     2693
Ile Thr Ser Glu Gly Gly Lys Cys Val Ala Leu Ala Val Lys Asn Ser
                800                 805                 810 acc tcc atc gtt gat gtt ggg atg tgg ggt aat cag att gga gac gaa     2741
Thr Ser Ile Val Asp Val Gly Met Trp Gly Asn Gln Ile Gly Asp Glu
        815                 820                 825 ggg gca aag gcc ttc gca gag gca ttg aag gac cac ccc agc ctg acc     2789
Gly Ala Lys Ala Phe Ala Glu Ala Leu Lys Asp His Pro Ser Leu Thr
            830                 835                 840 act ctc agt ctt gca ttc aat ggc atc tct ccg gag gga ggg aag agc     2837
Thr Leu Ser Leu Ala Phe Asn Gly Ile Ser Pro Glu Gly Gly Lys Ser
        845                 850                 855 ctt gcg cag gcc ctg aag cag aac acc aca ctg aca gta atc tgg ctg     2885
Leu Ala Gln Ala Leu Lys Gln Asn Thr Thr Leu Thr Val Ile Trp Leu
860                 865                 870                 875 acc aaa aat gaa ctt aat gat gag tct gca gag tgc ttc gct gag atg     2933
Thr Lys Asn Glu Leu Asn Asp Glu Ser Ala Glu Cys Phe Ala Glu Met
                880                 885                 890 ctg aga gtg aac cag acg cta cgg cat tta tgg ctg atc cag aat cgc     2981
Leu Arg Val Asn Gln Thr Leu Arg His Leu Trp Leu Ile Gln Asn Arg
        895                 900                 905 atc aca gcc aag ggg aca gcg cag ctg gcg agg gca ctg cag aag aac     3029
Ile Thr Ala Lys Gly Thr Ala Gln Leu Ala Arg Ala Leu Gln Lys Asn
            910                 915                 920
```

-continued

| | |
|---|---|
| aca gcc ata aca gag att tgt ctc aat gga aac ttg att aag ccc gag<br>Thr Ala Ile Thr Glu Ile Cys Leu Asn Gly Asn Leu Ile Lys Pro Glu<br>925 930 935 | 3077 |
| gag gcc aaa gtc ttc gag aat gag aag aga atc atc tgc ttc<br>Glu Ala Lys Val Phe Glu Asn Glu Lys Arg Ile Ile Cys Phe<br>940 945 950 | 3119 |
| tgacggacgc tcctgggcag gatctttgtc ctaggttgct cctcagtcac agacagcact | 3179 |
| gtgcagtcag cagggtagca ggatgctgtg cagcgcctgc agcaaggtgc ctgtcaggag | 3239 |
| cccacacctc cacagtgcac accgatgtcc cctgctcatg cttggactgg tagcacccgc | 3299 |
| gccgcggctg agaccctgca gacgcaggga gtcttaggaa ccatcgtcac cactcaaagc | 3359 |
| cagcagggca tcttctgtac aaagatctcc ctgcatatcc actagacgga agctgaagga | 3419 |
| acgcaacagc agaggaggcc aacagacgcc tggctgaagg ctccgtggga ccaacggtgt | 3479 |
| caccttcaga aaagagctgg gaacttgagc agagccgatg gtaacttctt ggggaaagaa | 3539 |
| ggcacccagt gactgcatgg ttattctgag tcctccttcc tctgcttagt ccctctcact | 3599 |
| gtacaggtct gtttcttcct cgcagctgtg gctgctgaag taggtccact gtggggagag | 3659 |
| ctcatcacag actttggttc ggttctggat tctcagtggt ggcaaccgag agtcagacga | 3719 |
| tacctctag gtcagtctca gaggatctct atgctgtgag agggttgagg gcccacccag | 3779 |
| aatttttttt ttttaccagt ttttactgtg cctgccccag gagggagaat tacttcccag | 3839 |
| cctccacagc agcaggcatg gcttgcctca atggtcctga gatcccaaca aaactctctc | 3899 |
| ccttgcctgt gagcagaaag tatcttcatg tcctcagaag ttggagggtg actggacaca | 3959 |
| gttaagactc agagagccag ctgatagctc aaagcaaagc atggcacata cccaccacca | 4019 |
| taccatggtg cgcatgggat gggacagttg gaatgttgca gataacgtgt tcttttgcca | 4079 |
| gttcatttgt taataaaata tttaaaacgt taaaaaaaaa aaaaaaaaaa aaaaagggc | 4139 |
| gg | 4141 |

<210> SEQ ID NO 43
<211> LENGTH: 953
<212> TYPE: PRT
<213> ORGANISM: Mus musculus

<400> SEQUENCE: 43

```
Met Glu Glu His Gly His His Glu Met Glu Gly Thr Pro Leu Gly Cys
  1               5                  10                  15

His Ser His Ile Lys Leu Leu Lys Ile Asn Arg Glu His Leu Val Thr
             20                  25                  30

Asn Ile Arg Asn Thr Gln Cys Leu Val Asp Asn Leu Leu Glu Asn Gly
         35                  40                  45

Tyr Phe Ser Ala Glu Asp Ala Glu Ile Val Cys Ala Cys Pro Thr Lys
 50                  55                  60

Pro Asp Lys Val Arg Lys Ile Leu Asp Leu Val Gln Ser Lys Gly Glu
 65                  70                  75                  80

Glu Val Ser Glu Phe Phe Leu Tyr Val Leu Gln Gln Leu Glu Asp Ala
                 85                  90                  95

Tyr Val Asp Leu Arg Leu Trp Leu Ser Glu Ile Gly Phe Ser Pro Ser
            100                 105                 110

Gln Leu Ile Arg Thr Lys Thr Ile Val Asn Thr Asp Pro Val Ser Arg
        115                 120                 125

Tyr Thr Gln Gln Leu Arg His Gln Leu Gly Arg Asp Ser Lys Phe Met
    130                 135                 140
```

```
Leu Cys Tyr Ala Gln Lys Glu Asp Leu Leu Glu Glu Thr Tyr Met
145                 150                 155                 160

Asp Thr Leu Met Gly Leu Val Gly Phe Asn Asn Glu Asn Leu Gly Ser
            165                 170                 175

Leu Gly Gly Leu Asp Cys Leu Leu Asp His Ser Thr Gly Val Leu Asn
                180                 185                 190

Glu His Gly Glu Thr Val Phe Val Phe Gly Asp Ala Gly Val Gly Lys
            195                 200                 205

Ser Met Leu Leu Gln Arg Leu Gln Ser Leu Trp Ala Ser Gly Arg Leu
210                 215                 220

Thr Ser Thr Ala Lys Phe Phe His Phe Arg Cys Arg Met Phe Ser
225                 230                 235                 240

Cys Phe Lys Glu Ser Asp Met Leu Ser Leu Gln Asp Leu Leu Phe Lys
                245                 250                 255

His Phe Cys Tyr Pro Glu Gln Asp Pro Glu Glu Val Phe Ser Phe Leu
            260                 265                 270

Leu Arg Phe Pro His Thr Ala Leu Phe Thr Phe Asp Gly Leu Asp Glu
        275                 280                 285

Leu His Ser Asp Phe Asp Leu Ser Arg Val Pro Asp Ser Cys Cys Pro
290                 295                 300

Trp Glu Pro Ala His Pro Leu Val Leu Leu Ala Asn Leu Leu Ser Gly
305                 310                 315                 320

Arg Leu Leu Lys Gly Ala Gly Lys Leu Leu Thr Ala Arg Thr Gly Val
                325                 330                 335

Glu Val Pro Arg Gln Leu Leu Arg Lys Lys Val Leu Leu Arg Gly Phe
            340                 345                 350

Ser Pro Ser His Leu Arg Ala Tyr Ala Arg Arg Met Phe Pro Glu Arg
        355                 360                 365

Thr Ala Gln Glu His Leu Leu Gln Gln Leu Asp Ala Asn Pro Asn Leu
        370                 375                 380

Cys Ser Leu Cys Gly Val Pro Leu Phe Cys Trp Ile Ile Phe Arg Cys
385                 390                 395                 400

Phe Gln His Phe Gln Thr Val Phe Glu Gly Ser Ser Gln Leu Pro
            405                 410                 415

Asp Cys Ala Val Thr Leu Thr Asp Val Phe Leu Leu Val Thr Glu Val
                420                 425                 430

His Leu Asn Arg Pro Gln Pro Ser Ser Leu Val Gln Arg Asn Thr Arg
            435                 440                 445

Ser Pro Ala Glu Thr Leu Arg Ala Gly Trp Arg Thr Leu His Ala Leu
450                 455                 460

Gly Glu Val Ala His Arg Gly Thr Asp Lys Ser Leu Phe Val Phe Gly
465                 470                 475                 480

Gln Glu Glu Val Gln Ala Ser Lys Leu Gln Glu Gly Asp Leu Gln Leu
                485                 490                 495

Gly Phe Leu Arg Ala Leu Pro Asp Val Gly Pro Glu Gln Gly Gln Ser
            500                 505                 510

Tyr Glu Phe Phe His Leu Thr Leu Gln Ala Phe Phe Thr Ala Phe Phe
            515                 520                 525

Leu Val Ala Asp Asp Lys Val Ser Thr Arg Glu Leu Leu Arg Phe Phe
        530                 535                 540

Arg Glu Trp Thr Ser Pro Gly Glu Ala Thr Ser Ser Ser Cys His Ser
545                 550                 555                 560
```

-continued

```
Ser Phe Phe Ser Phe Gln Cys Leu Gly Gly Arg Ser Arg Leu Gly Pro
            565                 570                 575

Asp Pro Phe Arg Asn Lys Asp His Phe Gln Phe Thr Asn Leu Phe Val
            580                 585                 590

Cys Gly Leu Leu Ala Lys Ala Arg Gln Lys Leu Leu Arg Gln Leu Val
            595                 600                 605

Pro Lys Ala Ile Leu Arg Arg Lys Arg Lys Ala Leu Trp Ala His Leu
610                 615                 620

Phe Ala Ser Leu Arg Ser Tyr Leu Lys Ser Leu Pro Arg Val Gln Ser
625                 630                 635                 640

Gly Gly Phe Asn Gln Val His Ala Met Pro Thr Phe Leu Trp Met Leu
            645                 650                 655

Arg Cys Ile Tyr Glu Thr Gln Ser Gln Lys Val Gly Arg Leu Ala Ala
            660                 665                 670

Arg Gly Ile Ser Ala Asp Tyr Leu Lys Leu Ala Phe Cys Asn Ala Cys
            675                 680                 685

Ser Ala Asp Cys Ser Ala Leu Ser Phe Val Leu His His Phe His Arg
            690                 695                 700

Gln Leu Ala Leu Asp Leu Asp Asn Asn Asn Leu Asn Asp Tyr Gly Val
705                 710                 715                 720

Gln Glu Leu Gln Pro Cys Phe Ser Arg Leu Thr Val Ile Arg Leu Ser
            725                 730                 735

Val Asn Gln Ile Thr Asp Thr Gly Val Lys Val Leu Cys Glu Glu Leu
            740                 745                 750

Thr Lys Tyr Lys Ile Val Thr Phe Leu Gly Leu Tyr Asn Asn Gln Ile
            755                 760                 765

Thr Asp Ile Gly Ala Arg Tyr Val Ala Gln Ile Leu Asp Glu Cys Arg
            770                 775                 780

Gly Leu Lys His Leu Lys Leu Gly Lys Asn Arg Ile Thr Ser Glu Gly
785                 790                 795                 800

Gly Lys Cys Val Ala Leu Ala Val Lys Asn Ser Thr Ser Ile Val Asp
            805                 810                 815

Val Gly Met Trp Gly Asn Gln Ile Gly Asp Glu Gly Ala Lys Ala Phe
            820                 825                 830

Ala Glu Ala Leu Lys Asp His Pro Ser Leu Thr Thr Leu Ser Leu Ala
            835                 840                 845

Phe Asn Gly Ile Ser Pro Glu Gly Gly Lys Ser Leu Ala Gln Ala Leu
850                 855                 860

Lys Gln Asn Thr Thr Leu Thr Val Ile Trp Leu Thr Lys Asn Glu Leu
865                 870                 875                 880

Asn Asp Glu Ser Ala Glu Cys Phe Ala Glu Met Leu Arg Val Asn Gln
            885                 890                 895

Thr Leu Arg His Leu Trp Leu Ile Gln Asn Arg Ile Thr Ala Lys Gly
            900                 905                 910

Thr Ala Gln Leu Ala Arg Ala Leu Gln Lys Asn Thr Ala Ile Thr Glu
            915                 920                 925

Ile Cys Leu Asn Gly Asn Leu Ile Lys Pro Glu Glu Ala Lys Val Phe
            930                 935                 940

Glu Asn Glu Lys Arg Ile Ile Cys Phe
945                 950

<210> SEQ ID NO 44
<211> LENGTH: 19
<212> TYPE: DNA
```

```
<213> ORGANISM: Artificial Sequence
<220> FEATURE:
<223> OTHER INFORMATION: oligonucleotide for PCR

<400> SEQUENCE: 44
agaaggtctg gtcggcaaa                                                19

<210> SEQ ID NO 45
<211> LENGTH: 18
<212> TYPE: DNA
<213> ORGANISM: Artificial Sequence
<220> FEATURE:
<223> OTHER INFORMATION: oligonucleotide for PCR

<400> SEQUENCE: 45
aagccctgag tggaagca                                                 18

<210> SEQ ID NO 46
<211> LENGTH: 409
<212> TYPE: PRT
<213> ORGANISM: Artificial Sequence
<220> FEATURE:
<223> OTHER INFORMATION: majority sequence
<221> NAME/KEY: VARIANT
<222> LOCATION: (1)...(409)
<223> OTHER INFORMATION: Xaa = Any Amino Acid

<400> SEQUENCE: 46
```

Met Glu Glu Gln Gly His Ser Glu Met Glu Ile Ile Pro Ser Glu Ser
 1               5                  10                  15

His Pro His Ile Gln Leu Leu Lys Ser Asn Arg Glu Leu Leu Val Thr
                20                  25                  30

His Ile Arg Asn Thr Gln Cys Leu Val Asp Asn Leu Leu Lys Asn Asp
            35                  40                  45

Tyr Phe Ser Ala Glu Asp Ala Glu Ile Val Cys Ala Cys Pro Thr Gln
        50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Leu Leu Gln Gln Leu Ala Asp Ala
                85                  90                  95

Tyr Val Asp Leu Arg Pro Trp Leu Leu Glu Ile Gly Phe Ser Pro Ser
            100                 105                 110

Leu Leu Thr Gln Ser Lys Val Val Asn Thr Asp Pro Val Ser Arg
        115                 120                 125

Tyr Thr Gln Gln Leu Arg His His Leu Gly Arg Asp Ser Lys Phe Val
    130                 135                 140

Leu Cys Tyr Ala Gln Lys Glu Glu Leu Leu Leu Glu Glu Ile Tyr Met
145                 150                 155                 160

Asp Thr Ile Met Met Glu Leu Val Gly Phe Ser Asn Glu Ser Leu Gly
                165                 170                 175

Ser Leu Asn Ser Leu Ala Cys Leu Leu Asp His Thr Thr Gly Ile Leu
            180                 185                 190

Asn Glu Gln Xaa Xaa Xaa Xaa Xaa Cys Lys Xaa Xaa Xaa Cys Xaa Cys
        195                 200                 205

Xaa Xaa Cys Xaa Xaa Xaa Thr Xaa Xaa Thr Xaa Xaa Xaa Xaa Pro Arg
    210                 215                 220

Arg Cys Leu Pro Xaa Cys Gly Pro Gly Gly Phe Xaa Xaa Xaa Trp Xaa
225                 230                 235                 240

Xaa Pro Cys Xaa Xaa Pro Xaa Trp Xaa Xaa Xaa Pro Xaa Xaa Xaa Trp

```
            245                 250                 255
Xaa Xaa Cys Xaa Xaa Xaa Glu Cys Xaa Trp Xaa Xaa Xaa Xaa Xaa
            260                 265                 270

Xaa Xaa Xaa Xaa Xaa Xaa Xaa Xaa Leu Arg Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Leu Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Phe
            405

<210> SEQ ID NO 47
<211> LENGTH: 966
<212> TYPE: PRT
<213> ORGANISM: Artificial Sequence
<220> FEATURE:
<223> OTHER INFORMATION: majority sequence

<400> SEQUENCE: 47

Met Glu Glu Gln Gly His Ser Glu Met Glu Gly Ile Pro Leu Gly Ser
1               5                   10                  15

His Ser His Ile Gln Leu Leu Lys Ile Asn Arg Glu Leu Leu Val Thr
            20                  25                  30

Asn Ile Arg Asn Thr Gln Cys Leu Val Asp Asn Leu Leu Glu Asn Gly
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Val Leu Gln Gln Leu Ala Asp Ala
                85                  90                  95

Tyr Val Asp Leu Arg Leu Trp Leu Leu Glu Ile Gly Phe Ser Pro Ser
            100                 105                 110

Leu Leu Ile Gln Ser Lys Val Val Asn Thr Asp Pro Val Ser Arg
        115                 120                 125

Tyr Thr Gln Gln Leu Arg His Gln Leu Gly Arg Asp Ser Lys Phe Val
    130                 135                 140

Leu Cys Tyr Ala Gln Lys Glu Asp Leu Leu Glu Glu Ile Tyr Met
145                 150                 155                 160

Asp Thr Leu Met Gly Leu Val Gly Phe Ser Asn Glu Ser Leu Gly Ser
                165                 170                 175

Leu Gly Gly Leu Ala Cys Leu Leu Asp His Ser Thr Gly Val Leu Asn
            180                 185                 190

Glu Gln Gly Glu Thr Val Phe Val Leu Gly Asp Ala Gly Val Gly Lys
```

-continued

```
                195                 200                 205
Ser Met Leu Leu Gln Arg Leu Gln Ser Leu Trp Ala Ser Gly Arg Leu
    210                 215                 220
Thr Ala Gly Ala Lys Phe Phe His Phe Arg Cys Arg Met Phe Ser
225                 230                 235                 240
Cys Phe Lys Glu Ser Asp Arg Leu Ser Leu Gln Asp Leu Leu Phe Lys
                245                 250                 255
His Phe Cys Tyr Pro Glu Gln Asp Pro Glu Val Phe Ala Phe Leu
            260                 265                 270
Leu Arg Phe Pro His Val Ala Leu Phe Thr Phe Asp Gly Leu Asp Glu
            275                 280                 285
Leu His Ser Asp Leu Asp Leu Ser Arg Val Pro Asp Ser Ser Cys Pro
    290                 295                 300
Trp Glu Pro Ala His Pro Leu Val Leu Leu Ala Asn Leu Leu Ser Gly
305                 310                 315                 320
Lys Leu Leu Lys Gly Ala Gly Lys Leu Leu Thr Ala Arg Thr Gly Val
                325                 330                 335
Glu Val Pro Arg Gln Leu Leu Arg Lys Val Leu Leu Arg Gly Phe
            340                 345                 350
Ser Pro Ser His Leu Arg Ala Tyr Ala Arg Arg Met Phe Pro Glu Arg
    355                 360                 365
Ala Ala Gln Asp His Leu Leu Ser Gln Leu Asp Ala Asn Pro Asn Leu
    370                 375                 380
Cys Ser Leu Cys Gly Pro Val Leu Phe Cys Trp Ile Ile Phe Arg Cys
385                 390                 395                 400
Phe Gln His Phe Gln Ala Ala Phe Glu Gly Ser Ser Ser Gln Leu Pro
                405                 410                 415
Asp Cys Ala Val Thr Leu Thr Asp Val Phe Leu Leu Val Thr Glu Val
            420                 425                 430
His Leu Asn Arg Met Gln Pro Ser Ser Leu Val Gln Arg Asn Thr Arg
            435                 440                 445
Ser Pro Ala Glu Thr Leu His Ala Gly Arg Asp Thr Leu His Ala Leu
    450                 455                 460
Gly Glu Val Ala His Arg Gly Thr Asp Lys Ser Leu Phe Val Phe Gly
465                 470                 475                 480
Gln Glu Glu Val Gln Ala Ser Gly Leu Gln Glu Gly Asp Leu Gln Leu
                485                 490                 495
Gly Phe Leu Arg Ala Leu Pro Asp Val Gly Pro Gly Asp Gly Gln
            500                 505                 510
Ser Tyr Glu Phe Phe His Leu Thr Leu Gln Ala Phe Phe Thr Ala Phe
    515                 520                 525
Phe Leu Val Ala Asp Asp Lys Val Gly Thr Gln Glu Leu Leu Arg Phe
    530                 535                 540
Phe Gln Glu Trp Thr Ser Pro Gly Gly Ala Ala Ser Ser Cys His
545                 550                 555                 560
Ser Ser Phe Leu Ser Phe Gln Cys Leu Gly Gly Ser Gly Arg Ala Gly
                565                 570                 575
Glu Asp Leu Phe Lys Asn Lys Asp His Phe Gln Phe Thr Asn Leu Phe
            580                 585                 590
Val Cys Gly Leu Leu Ala Lys Ala Lys Gln Lys Leu Leu Arg Gln Leu
            595                 600                 605
Val Pro Ala Ala Ala Leu Arg Arg Lys Arg Lys Ala Leu Trp Ala His
    610                 615                 620
```

-continued

```
Leu Phe Ala Ser Leu Arg Gly Tyr Leu Lys Ser Leu Pro Arg Val Gln
625                 630                 635                 640

Val Gly Gly Phe Asn Gln Val Gln Ala Met Pro Thr Phe Leu Trp Met
                645                 650                 655

Leu Arg Cys Ile Tyr Glu Thr Gln Ser Gln Lys Val Gly Gln Leu Ala
                660                 665                 670

Ala Arg Gly Ile Ser Ala Asp Tyr Leu Lys Leu Ala Phe Cys Asn Ala
            675                 680                 685

Cys Ser Ala Asp Cys Ser Ala Leu Ser Phe Val Leu His His Phe His
        690                 695                 700

Lys Gln Leu Ala Leu Asp Leu Asp Asn Asn Asn Leu Asn Asp Tyr Gly
705                 710                 715                 720

Val Gln Glu Leu Gln Pro Cys Phe Ser Arg Leu Thr Val Leu Arg Leu
                725                 730                 735

Ser Val Asn Gln Ile Thr Asp Gly Gly Val Lys Val Leu Ser Glu Glu
                740                 745                 750

Leu Thr Lys Tyr Lys Ile Val Thr Phe Leu Gly Leu Tyr Asn Asn Gln
            755                 760                 765

Ile Thr Asp Val Gly Ala Arg Tyr Val Ala Gln Ile Leu Asp Glu Cys
        770                 775                 780

Lys Gly Leu Thr His Leu Ser Leu Tyr Asn Asn Gln Ile Thr Asp Val
785                 790                 795                 800

Gly Ala Lys Leu Gly Lys Asn Lys Ile Thr Ser Glu Gly Gly Lys Tyr
                805                 810                 815

Val Ala Leu Ala Val Lys Asn Ser Thr Ser Ile Val Asp Val Gly Met
                820                 825                 830

Trp Gly Asn Gln Val Gly Asp Glu Gly Ala Lys Ala Phe Ala Glu Ala
            835                 840                 845

Leu Lys Asp His Pro Ser Leu Thr Thr Leu Ser Leu Ala Ser Asn Gly
        850                 855                 860

Ile Ser Thr Glu Gly Gly Lys Ser Leu Ala Gln Ala Leu Gln Gln Asn
865                 870                 875                 880

Thr Ser Leu Thr Val Leu Trp Leu Thr Gln Asn Glu Leu Asn Asp Glu
                885                 890                 895

Val Ala Glu Ser Leu Ala Glu Met Leu Lys Val Asn Gln Thr Leu Lys
                900                 905                 910

His Leu Trp Leu Ile Gln Asn Gln Ile Thr Ala Lys Gly Thr Ala Gln
            915                 920                 925

Leu Ala Asp Ala Leu Gln Ser Asn Thr Gly Ile Thr Glu Ile Cys Leu
        930                 935                 940

Asn Gly Asn Leu Ile Lys Pro Glu Glu Ala Lys Val Phe Glu Asp Glu
945                 950                 955                 960

Lys Arg Ile Ile Cys Phe
                965
```

MOLECULES OF THE CARD-RELATED PROTEIN FAMILY AND USES THEREOF

CROSS REFERENCE TO RELATED APPLICATIONS

This application is a divisional of application Ser. No. 09/207,359, filed Dec. 8, 1998, now U.S. Pat. No. 6,469,140, which is a continuation-in-part of application Ser. No. 09/099,041, filed Jun. 17, 1998, now U.S. Pat. No. 6,340,576, which is a continuation-in-part of application Ser. No. 09/019,942, now U.S. Pat. No. 6,033,855, filed Feb. 6, 1998.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as C. elegans, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are cysteine protease having specificity for aspartate at the substrate cleavage site. These proteases are primarily responsible for the degradation of cellular proteins that lead to the morphological changes seen in cells undergoing apoptosis. For example, one of the caspases identified in humans was previously known as the interleukin-1β (IL-1β) converting enzyme (ICE), a cysteine protease responsible for the processing of pro-IL-1β to the active cytokine. Overexpression of ICE in Rat-1 fibroblasts induces apoptosis (Miura et al., Cell 75:653 [1993]).

Many caspases and proteins that interact with caspases possess domains of about 60 amino acids called a caspase recruitment domain (CARD). Hofmann et al. (TIBS 22:155 [1997]) and others have postulated that certain apoptotic proteins bind to each other via their CARDs and that different subtypes of CARDs may confer binding specificity, regulating the activity of various caspases, for example.

The functional significance of CARDs have been demonstrated in recent publications. Duan et al. (Nature 385:86 [1997]) showed that deleting the CARD at the N-terminus of RAIDD, a newly identified protein involved in apoptosis, abolished the ability of RAIDD to bind to caspases. In addition, Li et al. (Cell 91:479 [1997]) showed that the N-terminal 97 amino acids of apoptotic protease activating factor-1 (Apaf-1) was sufficient to confer caspase-9-binding ability. Inohara et al. (J. Biol. Chem. 273:12296–12300, 1998) showed that Apaf-1 can bind several other caspases such as caspase-4 and caspase-8. Apaf-1 can interact with caspases via CARD-CARD interaction (Li et al., supra, Hu et al., PNAS, 95:4386–4391, 1998).

Nuclear factor-(kappa)B (NF-κB) is a transcription factor expressed in many cell types and which activates homologous or heterologous genes that have kB sites in their promoters. Quiescent NF-κB resides in the cytoplasm as a heterodimer between proteins referred to as p50 and p65 and is complexed with the regulatory protein IkB. NF-κB binding to IkB causes NF-κB to remain in the cytoplasm. At least two dozen stimuli that activate NF-κB are known (New England Journal of Medicine 336:1066 [1997]) and they include cytokines, protein kinase C activators, oxidants, viruses, and immune system stimuli. NF-κB activating stimuli activate specific IkB kinases that phosphorylate IkB leading to its degradation. Once liberated from IkB, NFκB translocates to the nucleus and activates genes with kB sites in their promoters. How all of these NF-κB activating stimuli act is unknown at the present time and it is presumed that novel NF-κB pathway components are involved. NF-κB and the NF-κB pathway has been implicated in mediating chronic inflammation in inflammatory diseases such as asthma, ulcerative colitis, rheumatoid arthritis (New England Journal of Medicine 336:1066 [1997]) and inhibiting NF-κB or NF-κB pathways may be an effective way of treating these diseases. NF-κB and the NF-κB pathway has also been implicated in atherosclerosis (American Journal of Cardiology 76:18C [1995]), especially in mediating fatty streak formation, and inhibiting NF-κB or NF-κB pathways may be an effective therapy for atherosclerosis.

SUMMARY OF THE INVENTION

The present invention is based, at least in part, on the discovery of genes encoding CARD-3 and CARD-4. The CARD-4 gene can express a long transcript that encodes CARD-4L, a short transcript that encodes partial CARD-4S, or two CARD-4 splice variants. A murine full length cDNA sequence for the murine ortholog of CARD-4L is also presented. CARD-3 and CARD-4 are intracellular proteins that are predicted to be involved in regulating caspase activation. CARD-4 is found to activate the NF-KB pathway and to enhance caspase 9-mediate cell death. In addition, proteins that bind to CARD-4 are presented including CARD-3, hNUDC, caspase 9, BCLX, and CARD-4.

The CARD-3 cDNA described below (SEQ ID NO:1) has a 1620 open reading frame (nucleotides 214 to 1833 of SEQ ID NO:1; SEQ ID NO:3) which encodes a 540 amino acid protein (SEQ ID NO:2). CARD-3 contains a kinase domain which extends from amino acid 1 to amino acid 300 of SEQ ID NO:2; SEQ ID NO:4, followed by a linker domain at amino acid 301 to amino acid 431 of SEQ ID NO:2; SEQ ID NO:5 and a CARD at amino acid 432 to amino acid 540 of SEQ ID NO:2; SEQ ID NO:6.

At least four forms of CARD-4 exist in the cell, a long form, CARD-4L, a short form, CARD-4S, and two splice variants, CARD-4Y and CARD-4Z. The cDNA of CARD-4L described below (SEQ ID NO:7) has a 2859 nucleotide open reading frame (nucleotides 35 245–3103 of SEQ ID NO:7; SEQ ID NO:9) which encodes a 953 amino acid protein (SEQ ID NO:8). CARD-4L protein possesses a CARD domain (amino acids 15–114; SEQ ID NO:10). The nucleotide sequence of the full length cDNA corresponding to the murine ortholog of human CARD-4L is presented (SEQ ID NO:42) as is the predicted amino acid sequence of murine CARD-4L (SEQ ID NO:43). A comparison between the predicted amino acid sequences of human CARD-4L and murine CARD-4L is also depicted in FIGS. 17A–17B.

Human CARD-4L is also predicted to have a nucleotide binding domain which extends from about amino acid 198 to about amino acid 397 of SEQ ID NO:8; SEQ ID NO:11, a Walker Box "A", which extends from about amino acid 202 to about amino acid 209 of SEQ ID NO:8; SEQ ID NO:12, a Walker Box "B", which extends from about amino acid 280 to about amino acid 284, of SEQ ID NO:8; SEQ ID NO:13, a kinase 3a subdomain, which extends from about amino acid 327 to about amino acid 338 of SEQ ID NO:8; SEQ ID NO:14, and ten Leucine-rich repeats which extend from about amino acid 674 to about amino acid 950 of SEQ ID NO:8. The first Leucine-rich repeat extends from about amino acid 674 to about amino acid 701 of SEQ ID NO:8; SEQ ID NO:15. The second Leucine-rich repeat extends from about amino acid 702 to about amino acid 727 of SEQ ID NO:8; SEQ ID NO:16. The third Leucine-rich repeat extends from about amino acid 728 to about amino acid 754 of SEQ ID NO:8; SEQ ID NO:17. The fourth Leucine-rich repeat extends from about amino acid 755 to about amino acid 782 of SEQ ID NO:8; SEQ ID NO:18. The fifth Leucine-rich repeat extends from about amino acid 783 to about amino acid 810 of SEQ ID NO:8; SEQ ID NO:19. The sixth Leucine-rich repeat extends from about amino acid 811 to about amino acid 838 of SEQ ID NO:8; SEQ ID NO:20. The seventh Leucine-rich repeat extends from about amino acid 839 to about amino acid 866 of SEQ ID NO:8; SEQ ID NO:21. The eighth Leucine-rich repeat extends from about amino acid 867 to about amino acid 894 of SEQ ID NO:8; SEQ ID NO:22. The ninth Leucine-rich repeat extends from about amino acid 895 to about amino acid 922 of SEQ ID NO:8; SEQ ID NO:23 and the tenth leucine-rich repeat extends from about amino acid 923 to about amino acid 950 of SEQ ID NO:8; SEQ ID NO:24.

The partial cDNA of CARD-4S described below (SEQ ID NO:25) has a 1470 nucleotide open reading frame (nucleotides 1–1470 of SEQ ID NO:25; SEQ ID NO:27) which encodes a 490 amino acid protein (SEQ ID NO:26). CARD-4S protein possesses a CARD domain (amino acids 1–74 of SEQ ID NO:26; SEQ ID NO:28). CARD-4S is predicted to have a P-Loop which extends from about amino acid 163 to about amino acid 170 of SEQ ID NO:26; SEQ ID NO:29, and a Walker Box "B" which extends form about amino acid 241 to about amino acid 245 of a SEQ ID NO:26; SEQ ID NO:30.

A human CARD-4Y nucleotide cDNA sequence is presented (SEQ ID NO:38) as is the amino acid sequence of the predicted CARD-4Y product (SEQ ID NO:39). A human CARD-4Z nucleotide cDNA sequence is presented (SEQ ID NO:40) as is the amino acid sequence of the predicted CARD-4Z product (SEQ ID NO:41). A comparison of the CARD-4Y, CARD-4Z, and human CARD-4L predicted amino acid sequences is also shown in FIGS. 14A–14G.

Like other proteins containing a CARD domain, both CARD-3 and CARD-4 are expected to participate in the network of interactions that lead to caspase activity. Human CARD-4L is expected to play a functional role in caspase activation similar to that of Apaf-1 (Zou et al., Cell, 90:405–413, 1997). For example, upon activation, CARD-4L might bind a nucleotide, thus allowing CARD-4L to bind and activate a CARD-containing caspase via a CARD-CARD interaction, leading to apoptotic death of the cell. For example, in Example 10, CARD-4 is shown to enhance caspase 9 activity and in Example 12, CARD-4 is shown to physically associate with caspase 9. Accordingly, CARD-3 and CARD-4 molecules are useful as modulating agents in regulating a variety of cellular processes including cell growth and cell death. In one aspect, this invention provides isolated nucleic acid molecules encoding CARD-3 or CARD-4 proteins or biologically active portions thereof, as well as nucleic acid fragments suitable as primers or hybridization probes for the detection of CARD-3 or CARD-4 encoding nucleic acids.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, or abnormal activity of a caspase by administering a compound that modulates the expression of CARD-3 or CARD-4 (at the DNA, mRNA or protein level, e.g., by altering mRNA splicing) or by altering the activity of CARD-3 or CARD-4. Examples of such compounds include small molecules, antisense nucleic acid molecules, ribozymes, and polypeptides.

Certain disorders are associated with an increased number of surviving cells, which are produced and continue to survive or proliferate when apoptosis is inhibited. These disorders include cancer (particularly follicular lymphomas, carcinomas associated with mutations in p53, and hormone-dependent tumors such as breast cancer, prostate cancer, and ovarian cancer), autoimmune disorders (such as systemic lupus erythematosis, immune-mediated glomerulonephritis), and viral infections (such as those caused by herpesviruses, poxviruses, and adenoviruses).

Failure to remove autoimmune cells that arise during development or that develop as a result of somatic mutation during an immune response can result in autoimmune disease. One of the molecules that plays a critical role in regulating cell death in lymphocytes is the cell surface receptor for Fas.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

The invention features a nucleic acid molecule which is at least 45% (or 55%, 65%, 75%, 85%, 95%, or 98%) identical to the nucleotide sequence shown in SEQ ID NO:1, SEQ ID NO:3, SEQ ID NO:7, SEQ ID NO:9, SEQ ID:25, SEQ ID NO:27, SEQ ID NO:38, SEQ ID NO:40, and SEQ ID NO:42, the nucleotide sequence of the cDNA insert of the plasmid deposited with ATCC as Accession Number (the "cDNA of ATCC 203037"), the nucleotide sequence of the cDNA insert of the plasmid deposited with ATCC as Accession Number (the "cDNA of ATCC 203035"), the nucleotide sequence of the cDNA insert of the plasmid deposited with ATCC as Accession Number (the "cDNA of ATCC 203036"), or a complement thereof.

The invention features a nucleic acid molecule which includes a fragment of at least 150 (300, 325, 350, 375, 400, 425, 450, 500, 550, 600, 650, 700, 800, 900, 1000, 1300, 1600 or 1931) nucleotides of the nucleotide sequence shown in SEQ ID NO:1, or SEQ ID NO:3, or the nucleotide sequence of the cDNA ATCC 203037, or a complement thereof.

The invention also features a nucleic acid molecule which includes a fragment of at least 150 (350, 400, 450, 500, 550, 600, 650, 700, 800, 900, 1000, 1300, 1600, 1900, 2100, 2400, 2700, 3000, or 3382) nucleotides of the nucleotide sequence shown in SEQ ID NO:7, SEQ ID NO:9, SEQ ID NO:42 or the nucleotide sequence of the cDNA ATCC 203035, or a complement thereof.

Also within the invention is a nucleic acid molecule which includes a fragment of at least 150 (350, 400, 450, 500, 550, 600, 650, 700, 800, 900, 1000, 1300, 1600, 1900, 2100, 2400, 2700, and 3080) nucleotides of the nucleotide sequence shown in SEQ ID NO:25, SEQ ID NO:27, SEQ ID NO:38, SEQ ID NO:40, or the nucleotide sequence of the cDNA ATCC 203036, or a complement thereof.

The invention features a nucleic acid molecule which includes a nucleotide sequence encoding a protein having an amino acid sequence that is at least 45% (or 55%, 65%, 75%, 85%, 95%, or 98%) identical to the amino acid sequence of SEQ ID NO:2, SEQ ID NO:8, SEQ ID NO:26, SEQ ID NO:39, SEQ ID NO:41, and SEQ ID NO:43, or the amino acid sequence encoded by the cDNA of ATCC 203037, the amino acid sequence encoded by the cDNA of ATCC 203035, or the amino acid sequence encoded by the cDNA of ATCC 203036.

In an embodiment, a CARD-3 nucleic acid molecule has the nucleotide sequence shown in SEQ ID NO:1, or SEQ ID NO:3, or the nucleotide sequence of the cDNA of ATCC 203037. In another embodiment, a CARD-4L nucleic acid molecule has the nucleotide sequence shown in SEQ ID NO:7, or SEQ ID NO:9, or the nucleotide sequence of the cDNA of ATCC 203035. In yet another embodiment, a CARD-4S nucleic acid molecule has the nucleotide sequence shown in SEQ ID NO:25, or SEQ ID NO:27, or the nucleotide sequence of the cDNA of ATCC 203036. In another embodiment, a murine CARD-4L nucleic acid molecule has the nucleotide sequence shown in SEQ ID NO:42.

In another embodiment, a CARD-4Y nucleic acid molecule has the nucleotide sequence shown in SEQ ID NO:38 or the nucleotide sequence of the cDNA of ATCC 203036. In another embodiment, a CARD-4Z nucleic acid molecule has the nucleotide sequence shown in SEQ ID NO:40 or the nucleotide sequence of the cDNA of ATCC 203036.

Also within the invention is a nucleic acid molecule which encodes a fragment of a polypeptide having the amino acid sequence of SEQ ID NO:2 or SEQ ID NO:8 or SEQ ID NO:26 or SEQ ID NO:39 or SEQ ID NO:41 or SEQ ID NO:43, the fragment including at least 15 (25, 30, 50, 100, 150, 300, 400 or 540, 600, 700, 800, 953) contiguous amino acids of SEQ ID NO:2 or SEQ ID NO:8 or SEQ ID NO:26 or SEQ ID NO:39 or SEQ ID NO:41 or SEQ ID NO:43 or the polypeptide encoded by the cDNA of ATCC Accession Number 203037, or the polypeptide encoded by the cDNA of ATCC Accession Number 203035 or the polypeptide encoded by the cDNA of ATCC Accession Number 203037.

The invention includes a nucleic acid molecule which encodes a naturally occurring allelic variant of a polypeptide comprising the amino acid sequence of SEQ ID NO:2 or SEQ ID NO:39 or SEQ ID NO:41 or SEQ ID NO:43 or an amino acid sequence encoded by the cDNA of ATCC Accession Number 203037, wherein the nucleic acid molecule hybridizes to a nucleic acid molecule comprising SEQ ID NO:1 or SEQ ID NO:3 or SEQ ID NO:38 or SEQ ID NO:40 or SEQ ID NO:42 under stringent conditions. The invention also includes a nucleic acid molecule which encodes a naturally occurring allelic variant of a polypeptide comprising the amino acid sequence of SEQ ID NO:8 or an amino acid sequence encoded by the cDNA of ATCC Accession Number 203035, wherein the nucleic acid molecule hybridizes to a nucleic acid molecule comprising SEQ ID NO:7 or SEQ ID NO:9 under stringent conditions.

The invention also includes a nucleic acid molecule which encodes a naturally occurring allelic variant of a polypeptide comprising the amino acid sequence of SEQ ID NO:26 or an amino acid sequence encoded by the cDNA of ATCC Accession Number 203036, wherein the nucleic acid molecule hybridizes to a nucleic acid molecule comprising SEQ ID NO:25 or SEQ ID NO:27 under stringent conditions. In general, an allelic variant of a gene will be readily identifiable as mapping to the same chromosomal location as said gene. For example, in Example 6, the chromosomal location of the human CARD-4 gene is discovered to be chromosome 7 close to the SHGC-31928 genetic marker. Allelic variants of human CARD-4 will be readily identifiable as mapping to the human CARD-4 locus on chromosome 7 near genetic marker SHGC-31928.

Also within the invention are: an isolated CARD-3 protein having an amino acid sequence that is at least about 65%, preferably 75%, 85%, 95%, or 98% identical to the amino acid sequence of SEQ ID NO:2; an isolated CARD-3 protein having an amino acid sequence that is at least about 85%, 95%, or 98% identical to the kinase domain of SEQ ID NO:2 (e.g., about amino acid residues 1 to 300 of SEQ ID NO:2; SEQ ID NO:4); and an isolated CARD-3 protein having an amino acid sequence that is at least about 85%, 95%, or 98% identical to the linker domain of SEQ ID NO:2 (e.g., about amino acid residues 301 to 431 of SEQ ID NO:2; SEQ ID NO:5); an isolated CARD-3 protein having an amino acid sequence that is at least about 85%, 95%, or 98% identical to the CARD domain of SEQ ID NO:2 (e.g., about amino acid residues 432 to 540 of SEQ ID NO:2; SEQ ID NO:6); an isolated CARD-4L protein having an amino acid sequence that is at least about 65%, preferably 75%, 85%, 95%, or 98% identical to the amino acid sequence of SEQ ID NO:8; an isolated CARD-4L protein having an amino acid sequence that is at least about 85%, 95%, or 98% identical to the CARD domain of SEQ ID NO:8 (e.g., about amino acid residues 15 to 114 of SEQ ID NO:8; SEQ ID NO:10); an isolated CARD-4L protein having an amino acid sequence that is at least about 85%, 95%, or 98% identical to the nucleotide binding domain of SEQ ID NO:8 (e.g., about amino acid residues 198 to 397 of SEQ ID NO:8; SEQ ID NO:11; an isolated CARD-4L protein having an amino acid sequence that is at least about 85%, 95%, or 98% identical to a kinase 3a subdomain of SEQ ID NO:8 (e.g., about amino acid residues 327 to 338 of SEQ ID NO:8; SEQ ID NO:14); an isolated CARD-4L protein having an amino acid sequence that is at least about 85%, 95%, or 98% identical to the Leucine-rich repeats of SEQ ID NO:8 (e.g., about amino acid residues 674 to 701 of SEQ ID NO:8; SEQ ID NO:15; from amino acid 702 to amino acid 727 of SEQ ID NO:8; SEQ ID NO:16; which extends from amino acid 728 to amino acid 754 SEQ ID NO:8; SEQ ID NO:17; from amino acid 755 to amino acid 782 of SEQ ID NO:8; SEQ ID NO:18; from amino acid 783 to amino acid 810 of SEQ ID NO:8; SEQ ID NO:19; from amino acid 811 to amino acid 838 of SEQ ID NO:8; SEQ ID NO:20 from amino acid 839 to amino acid 866 of SEQ ID NO:8; SEQ ID NO:21; from amino acid 867 to amino acid 894 of SEQ ID NO:8; SEQ ID NO:22; from amino acid 895 to amino acid 922 of SEQ ID NO:8; SEQ ID NO:23; and from amino acid 923 to amino acid 950 of SEQ ID NO:8; SEQ ID NO:24); an isolated CARD-4S protein having an amino acid sequence that is at least about 65%, preferably 75%, 85%, 95%, or 98% identical to the amino acid sequence of SEQ ID NO:26; an isolated CARD-4S protein having an amino acid sequence that is at least about 85%, 95%, or 98% identical to the CARD domain of SEQ ID NO:26 (e.g., about amino acid residues 1 to 74 of SEQ ID NO:26; SEQ ID NO:28). Also within the invention are: an isolated murine CARD-4L protein having an amino acid sequence that is at least about 65%, preferably 75%, 85%, 95%, or 98% identical to the amino acid sequence of SEQ ID NO:44. Also within the invention are: an isolated CARD-4Y protein having an amino acid sequence that is at least about 65%, preferably 75%, 85%, 95%, or 98% identical to the amino acid sequence of SEQ ID NO:40. Also within the invention are: an isolated CARD-4Z protein having an amino acid sequence that is at least about 65%, preferably 75%, 85%, 95%, or 98% identical to the amino acid sequence of SEQ ID NO:42.

Also within the invention are: an isolated CARD-3 protein which is encoded by a nucleic acid molecule having a nucleotide sequence that is at least about 65%, preferably 75%, 85%, or 95% identical to SEQ ID NO:3 or the cDNA of ATCC 203037; an isolated CARD-3 protein which is encoded by a nucleic acid molecule having a nucleotide sequence at least about 65% preferably 75%, 85%, or 95% identical to the kinase domain encoding portion of SEQ ID NO:1 (e.g., about nucleotides 213 to 1113 of SEQ ID NO:1); an isolated CARD-3 protein which is encoded by a nucleic acid molecule having a nucleotide sequence at least about 65% preferably 75%, 85%, or 95% identical the linker domain encoding portion of SEQ ID NO:1 (e.g., about nucleotides 11 14 to 1506 of SEQ ID NO:1); and an isolated CARD-3 protein which is encoded by a nucleic acid molecule having a nucleotide sequence at least about 65% preferably 75%, 85%, or 95% identical the CARD domain encoding portion of SEQ ID NO:1 (e.g., about nucleotides 1507 to 1833 of SEQ ID NO:1); and an isolated CARD-3 protein which is encoded by a nucleic acid molecule having a nucleotide sequence which hybridizes under stringent hybridization conditions to a nucleic acid molecule having the nucleotide sequence of SEQ ID NO:3 or the non-coding strand of the cDNA of ATCC 203037. Also within the invention are: an isolated CARD-4Y protein which is encoded by a nucleic acid molecule having a nucleotide sequence that is at least about 65%, preferably 75%, 85%, or 95% identical to SEQ ID NO:39 or the cDNA of ATCC 203035.

Also within the invention are: an isolated CARD-4Z protein which is encoded by a nucleic acid molecule having a nucleotide sequence that is at least about 65%, preferably 75%, 85%, or 95% identical to SEQ ID NO:41 or the cDNA of ATCC 203036. Also within the invention are: an isolated murine CARD-4L protein which is encoded by a nucleic acid molecule having a nucleotide sequence that is at least about 65%, preferably 75%, 85%, or 95% identical to SEQ ID NO:43.

Also within the invention are: an isolated CARD-4L protein which is encoded by a nucleic acid molecule having a nucleotide sequence that is at least about 65%, preferably 75%, 85%, or 95% identical to SEQ ID NO:9 or the cDNA of ATCC 203035; an isolated CARD-4L protein which is encoded by a nucleic acid molecule having a nucleotide sequence at least about 65% preferably 75%, 85%, or 95% identical the CARD domain encoding portion of SEQ ID NO:7 (e.g., about nucleotides 287 to 586 of SEQ ID NO:7); an isolated CARD-4L protein which is encoded by a nucleic acid molecule having a nucleotide sequence at least about 65% preferably 75%, 85%, or 95% identical the nucleotide binding domain encoding portion of SEQ ID NO:7 (e.g., about nucleotides 836 to 1436 of SEQ ID NO:7); an isolated CARD-4L protein which is encoded by a nucleic acid molecule having a kinase 3a subdomain at least about 65% preferably 75%, 85%, or 95% identical the nucleotide binding domain encoding portion of SEQ ID NO:7 (e.g., about nucleotides 1223 to 1258 of SEQ ID NO:7); an isolated CARD-4L protein which is encoded by a nucleic acid molecule having a nucleotide sequence at least about 65% preferably 75%, 85%, or 95% identical the Leucine-rich repeats encoding portion of SEQ ID NO:7 (e.g., about nucleotides 2264 to 2347 of SEQ ID NO:7; about nucleotides 2348 to 2425 of SEQ ID NO:7; about nucleotides 2426 to 2506 of SEQ ID NO:7; about nucleotides 2507 to 2590 of SEQ ID NO:7; about nucleotides 2591 to 2674 of SEQ ID NO:7; about nucleotides 2675 to 2758 of SEQ ID NO:7; about nucleotides 2759 to 2842 of SEQ ID NO:7; about nucleotides 2843 to 2926 of SEQ ID NO:7; about nucleotides 2927 to 3010 of SEQ ID NO:7; about nucleotides 3011 to 3094 of SEQ ID NO:7; and an isolated CARD-4L protein which is encoded by a nucleic acid molecule having a nucleotide sequence which hybridizes under stringent hybridization conditions to a nucleic acid molecule having the nucleotide sequence of SEQ ID NO:9 or the non-coding strand of the cDNA of ATCC 203035.

Also within the invention are: an isolated CARD-4S protein which is encoded by a nucleic acid molecule having a nucleotide sequence that is at least about 65%, preferably 75%, 85%, or 95% identical to SEQ ID NO:27 or the cDNA of ATCC 203036; an isolated CARD-3 protein which is encoded by a nucleic acid molecule having a nucleotide sequence at least about 65% preferably 75%, 85%, or 95% identical the CARD domain encoding portion of SEQ ID NO:25 (e.g., about nucleotides 1 to 222 of SEQ ID NO:25);

an isolated CARD-3 protein which is encoded by a nucleic acid molecule having a nucleotide sequence at least about 65% preferably 75%, 85%, or 95% identical the P-Loop encoding portion of SEQ ID NO:25 (e.g., about nucleotides 485 to 510 of SEQ ID NO:25).

Also within the invention is a polypeptide which is a naturally occurring allelic variant of a polypeptide that includes the amino acid sequence of SEQ ID NO:2 or an amino acid sequence encoded by the cDNA insert of the plasmid deposited with ATCC as Accession Number 203037, wherein the polypeptide is encoded by a nucleic acid molecule which hybridizes to a nucleic acid molecule comprising SEQ ID NO:1 or SEQ ID NO:3 under stringent conditions.

Also within the invention is a polypeptide which is a naturally occurring allelic variant of polypeptide that includes the amino acid sequence of SEQ ID NO:8 or an amino acid sequence encoded by the cDNA insert of the plasmid deposited with ATCC as Accession Number 203035, wherein the polypeptide is encoded by a nucleic acid molecule which hybridizes to a nucleic acid molecule comprising SEQ ID NO:7 or SEQ ID NO:9 under stringent conditions.

Also within the invention is a polypeptide which is a naturally occurring allelic variant of a polypeptide that includes the amino acid sequence of SEQ ID NO:26 or an amino acid sequence encoded by the cDNA insert of the plasmid deposited with ATCC as Accession Number 203036, wherein the polypeptide is encoded by a nucleic acid molecule which hybridizes to a nucleic acid molecule comprising SEQ ID NO:25 or SEQ ID NO:27 under stringent conditions.

Another embodiment of the invention features CARD-3 or CARD-4 nucleic acid molecules which specifically detect CARD-3 or CARD-4 nucleic acid molecules, relative to nucleic acid molecules encoding other members of the CARD superfamily. For example, in one embodiment, a CARD-4L nucleic acid molecule hybridizes under stringent conditions to a nucleic acid molecule comprising the nucleotide sequence of SEQ ID NO:7, SEQ ID NO:9, or the cDNA of ATCC 203035, or a complement thereof. In another embodiment, the CARD-4L nucleic acid molecule is at least 300 (350, 400, 450, 500, 550, 600, 650, 700, 800, 900, 1000, 1300, 1600, 1900, 2100, 2400, 2700, 3000, or 3382) nucleotides in length and hybridizes under stringent conditions to a nucleic acid molecule comprising the nucleotide sequence shown in SEQ ID NO:7, SEQ ID NO:9, the cDNA of ATCC 203035, or a complement thereof. In another embodiment, an isolated CARD-4L nucleic acid molecule comprises nucleotides 287 to 586 of SEQ ID NO:7, encoding the CARD domain of CARD-4L, or a complement thereof. In yet another embodiment, the invention provides an isolated nucleic acid molecule Which is antisense to the coding strand of a CARD-4L nucleic acid.

Another aspect of the invention provides a vector, e.g., a recombinant expression vector, comprising a CARD-3 or a CARD-4L nucleic acid molecule of the invention. In another embodiment the invention provides a host cell containing such a vector. The invention also provides a method for producing CARD-3 or CARD-4 protein by culturing, in a suitable medium, a host cell of the invention containing a recombinant expression vector such that a CARD-3 or CARD-4 protein is produced.

Another aspect of this invention features isolated or recombinant CARD-3 or CARD-4 proteins and polypeptides. Preferred CARD-3 or CARD-4 proteins and polypeptides possess at least one biological activity possessed by naturally occurring human CARD-3 or CARD-4, e.g., (1) the ability to form protein:protein interactions with proteins in the apoptotic signaling pathway; (2) the ability to form CARD-CARD interactions with proteins in the apoptotic signaling pathway; (3) the ability to bind the CARD-3 or CARD-4 ligand; (4) the ability to bind to an intracellular target; and (5) the ability to bind to caspases. Other activities include: (1) modulation of cellular proliferation, (2) modulation of cellular differentiation and (3) modulation of cellular death (4) modulation of the NF-KB pathway.

The CARD-3 or CARD-4 proteins of the present invention, or biologically active portions thereof, can be operatively linked to a non-CARD-3 or non-CARD-4 polypeptide (e.g., heterologous amino acid sequences) to form CARD-3 or CARD-4 fusion proteins, respectively. The invention further features antibodies that specifically bind CARD-3 or CARD-4 proteins, such as monoclonal or polyclonal antibodies. In addition, the CARD-3 or CARD-4 proteins or biologically active portions thereof can be incorporated into pharmaceutical compositions, which optionally include pharmaceutically acceptable carriers.

In another aspect, the present invention provides a method for detecting the presence of CARD-3 or CARD-4 activity or expression in a biological sample by contacting the biological sample with an agent capable of detecting an indicator of CARD-3 or CARD-4 activity such that the presence of CARD-3 or CARD-4 activity is detected in the biological sample.

In another aspect, the invention provides a method for modulating CARD-3 or CARD-4 activity comprising contacting a cell with an agent that modulates (inhibits or stimulates) CARD-3 or CARD-4 activity or expression such that CARD-3 or CARD-4 activity or expression in the cell is modulated. In one embodiment, the agent is an antibody that specifically binds to CARD-3 or CARD-4 protein. In another embodiment, the agent modulates expression of CARD-3 or CARD-4 by modulating transcription of a CARD-3 or CARD-4 gene, splicing of a CARD-3 or CARD-4 mRNA, or translation of a CARD-3 or CARD-4 mRNA. In yet another embodiment, the agent is a nucleic acid molecule having a nucleotide sequence that is antisense to the coding strand of the CARD-3 or CARD-4 mRNA or the CARD-3 or CARD-4 gene.

In one embodiment, the methods of the present invention are used to treat a subject having a disorder characterized by aberrant CARD-3 or CARD-4 protein or nucleic acid expression or activity by administering an agent which is a CARD-3 or CARD-4 modulator to the subject. In one embodiment, the CARD-3 or CARD-4 modulator is a CARD-3 or CARD-4 protein. In another embodiment the CARD-3 or CARD-4 modulator is a CARD-3 or CARD-4 nucleic acid molecule. In other embodiments, the CARD-3 or CARD-4 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-3 or CARD-4 protein; (ii) mis-regulation of a gene encoding a CARD-3 or CARD-4 protein; and (iii) aberrant post-translational modification of a CARD-3 or CARD-4 protein, wherein a wild-type form of the gene encodes a protein with a CARD-3 or CARD-4 activity.

In another aspect, the invention provides a method for identifying a compound that binds to or modulates the activity of a CARD-3 or CARD-4 protein. In general, such methods entail measuring a biological activity of a CARD-3 or CARD-4 protein in the presence and absence of a test compound and identifying those compounds which alter the activity of the CARD-3 or CARD-4 protein.

The invention also features methods for identifying a compound which modulates the expression of CARD-3 or CARD-4 by measuring the expression of CARD-3 or CARD-4 in the presence and absence of a compound.

Other features and advantages of the invention will be apparent from the following detailed description and claims.

BRIEF DESCRIPTION OF THE DRAWINGS

FIG. 1 depicts the cDNA sequence (SEQ ID NO:1) of human CARD-3. The open reading frame of CARD-3 (SEQ ID NO:1) extends from nucleotide 213 to nucleotide 1833 nucleotide (SEQ ID NO:3).

Figure 2:
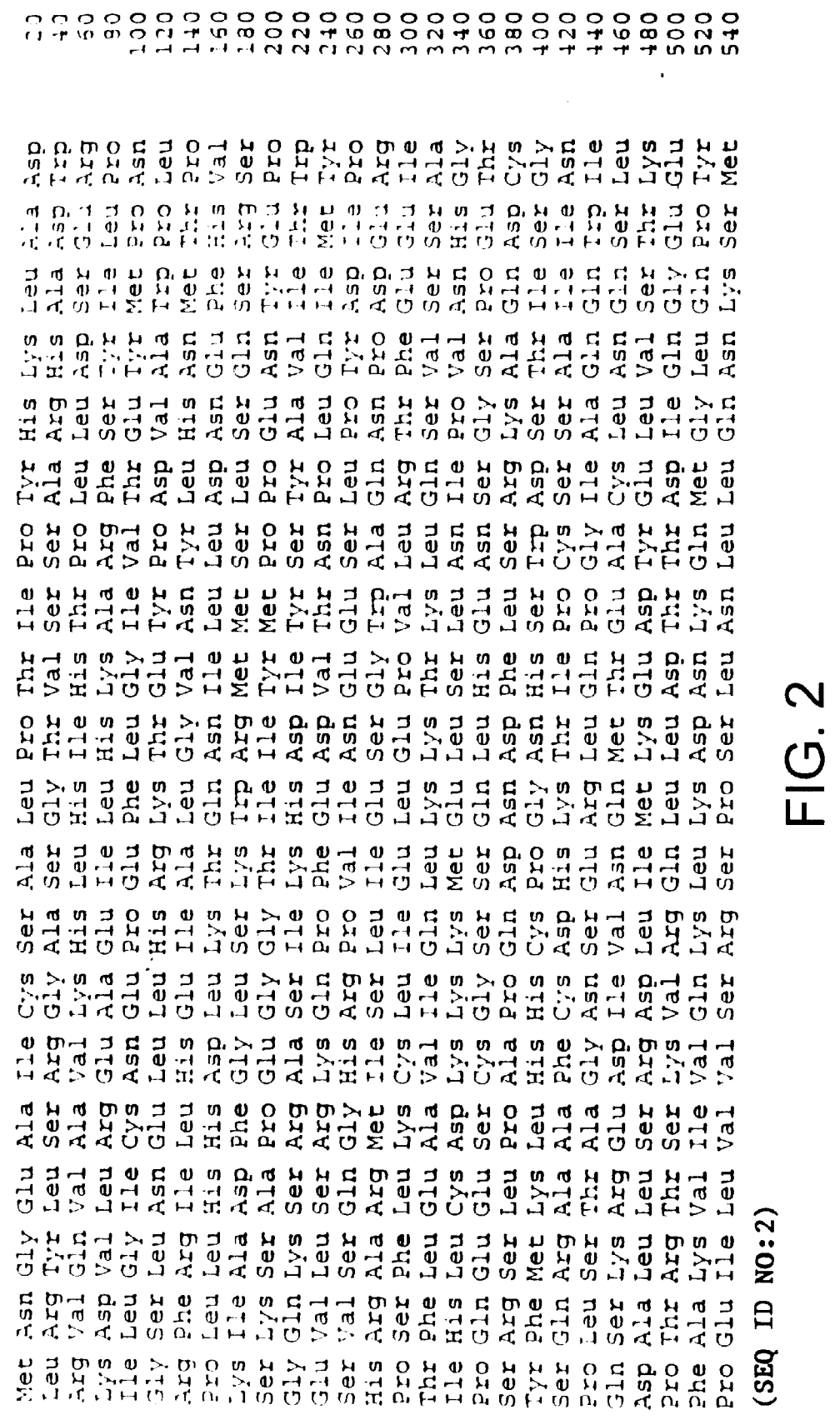

FIG. 2 depicts the predicted amino acid sequence (SEQ ID NO:2) of human CARD-3.

FIGS. 3A–3B depict the cDNA sequence (SEQ ID NO:7) of CARD-4L. The open reading frame of SEQ ID NO:7 extends from nucleotide 245 to nucleotide 3103 (SEQ ID NO:9).

FIG. 4 depicts the predicted amino acid sequence (SEQ ID NO:8) of human CARD-4L.

FIG. 5 depicts the partial cDNA sequence (SEQ ID NO:25) of CARD-4S and the predicted amino acid sequence (SEQ ID NO:25) of human CARD-4S. The open reading frame of CARD-4 (SEQ ID NO:25) extends from nucleotide 1 to nucleotide 1470 (SEQ ID NO:27).

FIG. 6 depicts the predicted amino acid sequence (SEQ ID NO:26) of human CARD-4S.

FIG. 7 depicts an alignment of the CARD domains of CARD-4 (SEQ ID NO:10), CARD-3 (SEQ ID NO:6), ARC-CARD (SEQ ID NO:31), cIAP1-CARD (SEQ ID NO:32), and cIAP2-CARD (SEQ ID NO:33).

FIGS. 10A–10C depict the cDNA sequence (SEQ ID NO:38) of the human CARD-4Y splice variant clone. The predicted open reading frame of the human CARD-4Y splice variant clone extends from nucleotide 438 to nucleotide 1184.

FIG. 11 depicts the amino acid sequence (SEQ ID NO:39) of the protein predicted to be encoded by the human CARD-4Y cDNA open reading frame.

FIG. 12 depicts the cDNA sequence (SEQ ID NO:40) of the human CARD-4Z splice variant clone. The predicted open reading frame of the human CARD-4Z splice variant clone extends from nucleotide 489 to nucleotide 980.

FIG. 13 depicts the amino sequence (SEQ ID NO:42) of the protein predicted to be encoded by the human CARD-4Z cDNA open reading frame.

FIGS. 14A–14G depict an alignment of human CARD-4L (SEQ ID NO:8), the predicted amino acid sequence of human CARD-4Y (SEQ ID NO:39), and the predicted amino acid sequence of human CARD-4Z (SEQ ID NO:41).

FIGS. 15A–15C depict the nucleotide sequence of the murine CARD-4L cDNA (SEQ ID NO:43).

FIGS. 17A–17B depict an alignment of human CARD-4L (SEQ ID NO:8) and the predicted amino acid sequence of murine CARD-4L (SEQ ID NO:44).

DETAILED DESCRIPTION OF THE INVENTION

Figure 8:
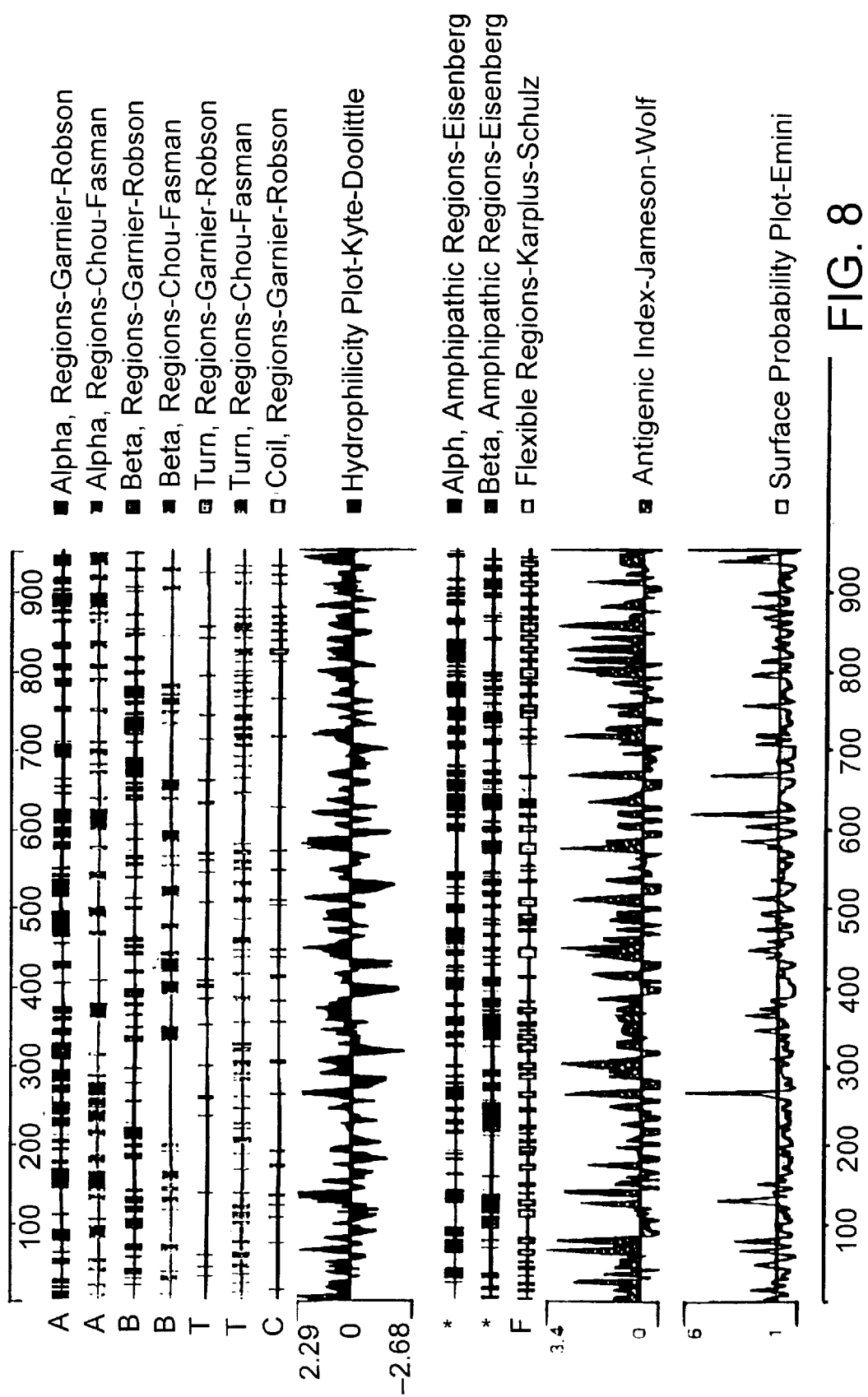
FIG. 8 is a plot showing predicted structural features of human CARD-4L.

The present invention is based, in part, on the discovery of cDNA molecules encoding human CARD-3, human CARD-4 and partial murine CARD-4L proteins. A nucleotide sequence encoding a human CARD-3 protein is shown in FIG. 1 (SEQ ID NO:1; SEQ ID NO:3 includes the open reading frame only). A predicted amino acid sequence of CARD-3 protein is also shown in FIG. 2 (SEQ ID NO:2). CARD-4 has at least two forms, a long form, CARD-4L, and a short form, CARD-4S, as well as two or more splice variants. A nucleotide sequence encoding a human CARD-4L protein is shown in FIGS. 3A–3B (SEQ ID NO:7; SEQ ID NO:9 includes the open reading frame only). A predicted amino acid sequence of CARD-4L protein is also shown in FIG. 4 (SEQ ID NO:8). A nucleotide sequence encoding a human CARD-4S protein is shown in FIG. 5 (SEQ ID NO:25; SEQ ID NO:27 includes the open reading frame only). A predicted amino acid sequence of CARD-4S protein is also shown in FIG. 6 (SEQ ID NO:26). Two additional splice variants of human CARD-4 are provided in FIGS. 10A–10C and 11 (human CARD-4Y) and FIGS. 12 and 13 (human CARD-4Z) (predicted amino acid sequences: SEQ ID NO:40 and SEQ ID NO:42 and nucleic acid sequences: SEQ ID NO:39 and SEQ ID NO:41). These two splice variants are predicted to contain 249 and 164 amino acids, respectively. An alignment of human CARD-4Y, human CARD-4Z and human CARD-4L is shown in FIGS. 14A–14G.

In addition to the human CARD-4 proteins, a full length nucleotide sequence of the murine ortholog of human CARD-4L is provided in FIGS. 15A–15C (SEQ ID NO:43). An alignment of murine CARD-4L with human CARD-4L is shown in FIGS. 17A–17B.

The human CARD-3 cDNA of FIG. 1 (SEQ ID NO:1), which is approximately 1931 nucleotides long including untranslated regions, encodes a protein amino acid having a molecular weight of approximately 61 kDa (excluding post-translational modifications). A plasmid containing a cDNA encoding human CARD-3 (pXE17A) was deposited with American Type Culture Collection (ATCC), 10801 University Boulevard, Manassas, Va. on May 14, 1998, and assigned Accession Number 203037. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human CARD-4L cDNA of FIGS. 3A–3B (SEQ ID NO:7), which is approximately 3382 nucleotides long including untranslated regions, encodes a protein amino acid having a molecular weight of approximately 108 kDa (excluding post-translational modifications). A plasmid containing a cDNA encoding human CARD-4L (pC4L1) was deposited with American Type Culture Collection (ATCC), 10801 University Boulevard, Manassas, Va. on May 14, 1998, and assigned Accession Number 203035. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human CARD-4S cDNA of FIG. 5 (SEQ ID NO:25), which is 3082 nucleotides long including untranslated regions. A plasmid containing a cDNA encoding human CARD-4S (pDB33E) was deposited with American Type Culture Collection (ATCC), 10801 University Boulevard, Manassas, Va. on May 14, 1998, and assigned Accession Number 203036. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 7:
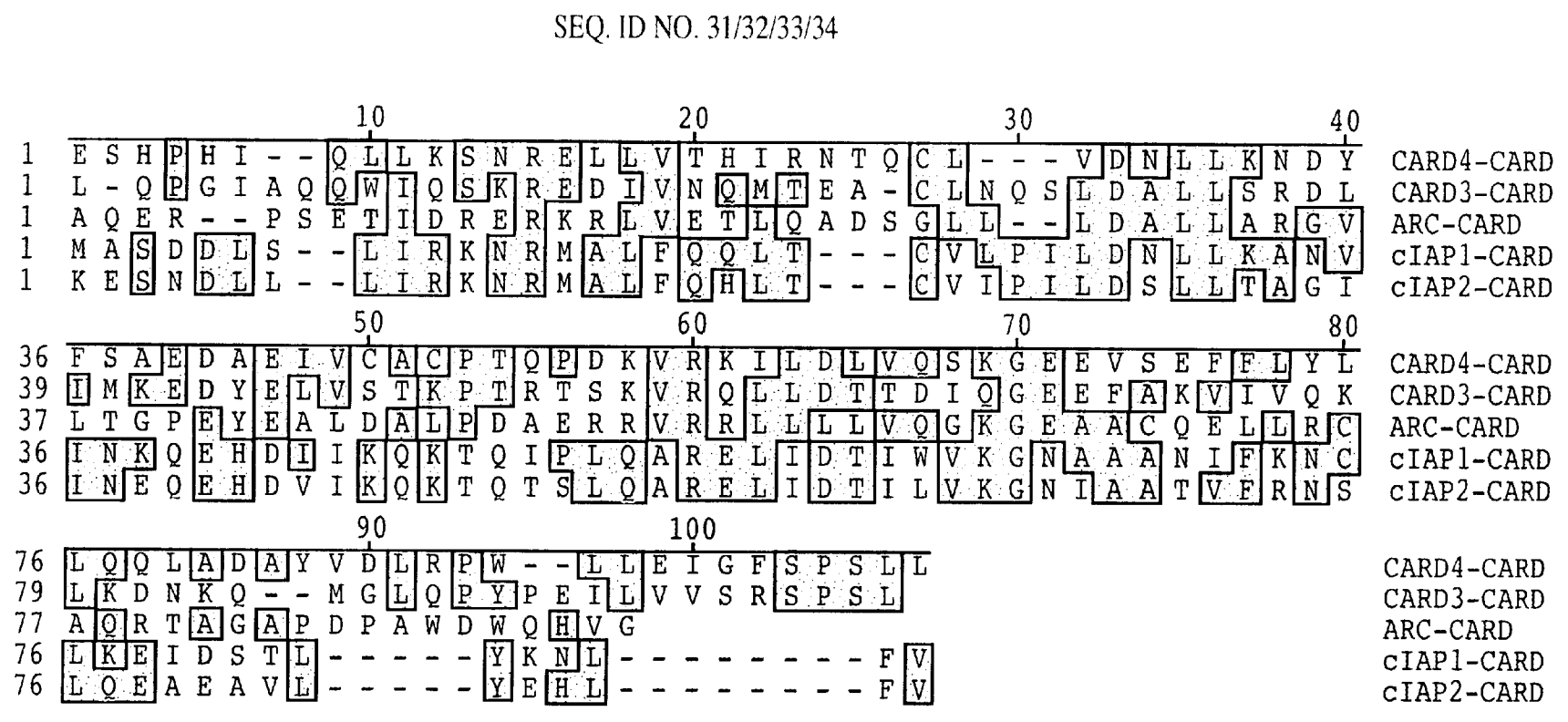

A region of human CARD-4L protein (SEQ ID NO:8) bears some similarity to a CARD domain of CARD-3 (SEQ ID NO:6), ARC-CARD (SEQ ID NO:31), cIAP1-CARD (SEQ ID NO:32), cIAP1-CARD (SEQ ID NO:33) and cIAP2-CARD (SEQ ID NO:34). This comparison is depicted in FIG. 7.

Human CARD-3 or CARD-4 are members of a family of molecules (the "CARD family") having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a CARD-3 or CARD-4 protein includes a CARD domain having at least about 65%, preferably at least about 75%, and more preferably about 85%, 95%, or 98% amino acid sequence identity to the CARD domain of SEQ ID NO:6 or the CARD domain of SEQ ID NO:10 or the CARD domain of SEQ ID NO:28.

Preferred CARD-3 or CARD-4 polypeptides of the present invention have an amino acid sequence sufficiently identical to the CARD domain consensus amino acid sequence of SEQ ID NO:6, SEQ ID NO:10, SEQ ID NO:28, respectively. The CARD-3 polypeptide also has an amino acid sequence sufficiently identical to the kinase domain consensus sequence of SEQ ID NO:4, and an amino acid sequence that is sufficiently identical to the linker domain of SEQ ID NO:5. The CARD-4L polypeptide has an amino acid sequence sufficiently identical to the nucleotide binding domain of SEQ ID NO:11, an amino acid sequence sufficiently identical to the Walker Box "A" of SEQ ID NO:12 or Walker Box "B" of SEQ ID NO:13, or an amino acid sequence sufficiently identical to the kinase 3a subdomain of SEQ ID NO:14, or an amino acid sequence sufficiently identical to the Leucine-rich repeats of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-3 or CARD-4 activity", "biological activity of CARD-3 or CARD-4" or "functional activity of CARD-3 or CARD-4", refers to an activity exerted by a CARD-3 or CARD-4 protein, polypeptide or nucleic acid molecule on a CARD-3 or CARD-4 responsive cell as determined in vivo, or in vitro, according to standard techniques. A CARD-3 or CARD-4 activity can be a direct activity, such as an association with or an enzymatic activity on a second protein or an indirect activity, such as a cellular signaling activity mediated by interaction of the CARD-3 or CARD-4 protein with a second protein. In an embodiment, a CARD-3 or CARD-4 activity includes at least one or more of the following activities: (i) interaction with proteins in the apoptotic signaling pathway (ii) interaction with a CARD-3 or CARD-4 ligand; or (iii) interaction with an intracellular target protein; (iv) interaction with caspases. For example, in example 4, CARD-3-containing proteins were shown to associate with CARD-4-containing proteins. In example 9, CARD-4 proteins were shown to induce NF-κB-mediated transcription. In example 10, CARD-4 was shown to enhance caspase 9 activity.

Accordingly, another embodiment of the invention features isolated CARD-3 or CARD-4 proteins and polypeptides having a CARD-3 or CARD-4 activity.

Various aspects of the invention are described in further detail in the following subsections.

I. Isolated Nucleic Acid Molecules

One aspect of the invention pertains to isolated nucleic acid molecules that encode CARD-3 or CARD-4 proteins or biologically active portions thereof, as well as nucleic acid molecules sufficient for use as hybridization probes to identify CARD-3 or CARD-4-encoding nucleic acids (e.g., CARD-3 or CARD-4 mRNA) and fragments for use as PCR primers for the amplification or mutation of CARD-3 or CARD-4 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated CARD-3 or CARD-4L/S nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:7, SEQ ID NO:9, SEQ ID NO:25, SEQ ID NO:26, SEQ ID NO:39, SEQ ID NO:41, SEQ ID NO:43, the cDNA of ATCC 203037, the cDNA of ATCC 203035, the cDNA of ATCC 203036, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:7, SEQ ID NO:9, SEQ ID NO:25, SEQ ID NO:26, SEQ ID NO:39, SEQ ID NO:41, SEQ ID NO:43, the cDNA of ATCC 203037 or the cDNA of ATCC 203035, or the cDNA of ATCC 203036, as a hybridization probe, CARD-3 or CARD-4 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard r PCR amplification techniques. The nucleic acid so amplified can be cloned into an appropriate vector and characterized by DNA sequence analysis. Furthermore, oligonucleotides corresponding to CARD-3 or CARD-4 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, SEQ ID NO:7, SEQ ID NO:9, SEQ ID NO:25, SEQ ID NO:26, SEQ ID NO:39, SEQ ID NO:41, SEQ ID NO:43, the cDNA of ATCC 203037 or the cDNA of ATCC 203035, or the cDNA of ATCC 203036, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding CARD-3 or CARD-4, for example, a fragment which can be used as a probe or primer or a fragment encoding a biologically active portion of CARD-3 or CARD-4. The nucleotide sequence determined from the cloning of the human CARD-3 or CARD-4, and the partial murine CARD-4 gene allows for the generation of probes and primers designed for use in identifying and/or cloning CARD-3 or CARD-4 homologues in other cell types, e.g., from other tissues, as well as CARD-3 or CARD-4 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:7, SEQ ID NO:9, the cDNA of ATCC 203037, the cDNA of ATCC 203035 or of a naturally occurring mutant of SEQ ID NO:1, SEQ ID NO:3, SEQ ID NO:7, SEQ ID NO:9, the cDNA of ATCC 203037, or the cDNA of ATCC 203035.

Probes based on the human CARD-3 or human CARD-4 or murine CARD-4 nucleotide sequence can be used to detect transcripts or genomic sequences encoding the same or identical proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-3 and CARD-4 proteins of the present invention, identifying cells or tissue which mis-express a CARD-3 or CARD-4 protein, such as by measuring a level of a CARD-3 or CARD-4-encoding nucleic acid in a sample of cells from a subject, e.g., detecting CARD-3 or CARD-4 mRNA levels or determining whether a genomic CARD-3 or CARD-4 gene has been mutated or deleted.

A nucleic acid fragment encoding a "biologically active portion of CARD-3 or CARD-4L" can be prepared by isolating a portion of SEQ ID NO:1, SEQ ID NO:3, SEQ ID NO:7, SEQ ID NO:9, or the nucleotide sequence of the cDNA of ATCC 203036, or the nucleotide sequence of the cDNA of ATCC 203035 which encodes a polypeptide having a CARD-3 or CARD-4 biological activity, expressing the encoded portion of CARD-3 or CARD-4 protein (e.g., by recombinant expression in vitro) and assessing the activity of the encoded portion of CARD-3 or CARD-4. For example, a nucleic acid fragment encoding a biologically active portion of CARD-3 or CARD-4 includes a CARD domain, e.g., SEQ ID NO:6 and SEQ ID NO:10 or SEQ ID NO:26.

The invention further encompasses nucleic acid molecules that differ from the nucleotide sequence of SEQ ID NO:1, SEQ ID NO:3, SEQ ID NO:7, SEQ ID NO:9, SEQ ID NO:25, SEQ ID NO:27, SEQ ID NO:39, SEQ ID NO:41, SEQ ID NO:43, the cDNA of ATCC 203037, or the cDNA of ATCC 203035, or the cDNA of ATCC 203036 due to degeneracy of the genetic code and thus encode the same CARD-3 or CARD-4 protein as that encoded by the nucleotide sequence shown in SEQ ID NO:1, SEQ ID NO:3, SEQ ID NO:7, SEQ ID NO:9, SEQ ID NO:25, SEQ ID NO:27, SEQ ID NO:39, SEQ ID NO:41, SEQ ID NO:43, the cDNA of ATCC 203037 or the cDNA of ATCC 203035, or the cDNA of ATCC 203036.

In addition to the human CARD-3 or CARD-4 nucleotide sequence shown in SEQ ID NO:1, SEQ ID NO:3, SEQ ID NO:7, SEQ ID NO:9, SEQ ID NO:25, SEQ ID NO:27, SEQ ID NO:39, SEQ ID NO:41, the cDNA of ATCC 203037, the cDNA of ATCC 203035, or the cDNA of ATCC 203036, and the murine CARD-4L cDNA sequence shown in SEQ ID NO:43 it will be appreciated by those skilled in the art that DNA sequence polymorphisms that lead to changes in the amino acid sequences of CARD-3 or CARD-4 may exist within a population (e.g., the human population). Such genetic polymorphism in the CARD-3 or CARD-4 gene may exist among individuals within a population due to natural allelic variation. As used herein, the terms "gene" and "recombinant gene" refer to nucleic acid molecules comprising an open reading frame encoding a CARD-3 or CARD-4 protein, preferably a mammalian CARD-3 or CARD-4 protein.

Such natural allelic variations can typically result in 1–5% variance in the nucleotide sequence of the CARD-3 or CARD-4 gene. Any and all such nucleotide variations and resulting amino acid polymorphisms in CARD-3 or CARD-4 that are the result of natural allelic variation and that do not alter the functional activity of CARD-3 or CARD-4 are intended to be within the scope of the invention.

Moreover, nucleic acid molecules encoding CARD-3 or CARD-4 proteins from other species (CARD-3 or CARD-4 orthologs/homologues), which have a nucleotide sequence which differs from that of a human CARD-3 or CARD-4, are intended to be within the scope of the invention. For example, Example 5 describes the murine CARD-4 ortholog. Nucleic acid molecules corresponding to natural allelic variants and homologues of the CARD-3 or CARD-4 cDNA of the invention can be isolated based on their identity to the human CARD-3 or human or murine CARD-4 nucleic acids disclosed herein using the human or murine cDNAs, or a portion thereof, as a hybridization probe according to standard hybridization techniques under stringent hybridization conditions. In general, an allelic variant of a gene will be readily identifiable as mapping to the same chromosomal location as said gene. For example, in Example 6, the chromosomal location of the human CARD-4 gene is discovered to be chromosome 7 close to the SHGC-31928 genetic marker. Allelic variants of human CARD-4 will be readily identifiable as mapping to the human CARD-4 locus on chromosome 7 near genetic marker SHGC-31928.

Accordingly, in another embodiment, an isolated nucleic acid molecule of the invention is at least 300 (325, 350, 375, 400, 425, 450, 500, 550, 600, 650, 700, 800, 900, 1000, 1300, 1600 or 1931) nucleotides in length and hybridizes under stringent conditions to the nucleic acid molecule comprising the nucleotide sequence, preferably the coding sequence, of SEQ ID NO:1, SEQ ID NO:3, or the cDNA of ATCC 203037. In yet another embodiment, an isolated nucleic acid molecule of the invention is at least 300 (325, 350, 375, 400, 425, 450, 500, 550, 600, 650, 700, 800, 900, 1000, or 1300, 1640, 1900, 2200, 2500, 2800, 3100, or 3382) nucleotides in length and hybridizes under stringent conditions to the nucleic acid molecule comprising the nucleotide sequence, preferably the coding sequence, of SEQ ID NO:7, SEQ ID NO:9, SEQ ID NO:39, SEQ ID NO:41, or the cDNA of ATCC 203035. Accordingly, in another embodiment, an isolated nucleic acid molecule of the invention is at least 300 (325, 350, 375, 400, 425, 450, 500, 550, 600, 650, 700, 800, 900, 1000, or 1300, 1640, 1900, 2200, 2500, 2800, 3100, 3300, 3600, 3900, 4200 or 4209) nucleotides in length and hybridizes under stringent conditions to the nucleic acid molecule comprising the nucleotide sequence, preferably the coding sequence, of SEQ ID NO:43.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, the cDNA of ATCC 203037 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CARD-3 or CARD-4 sequence that may exist in the population, the skilled artisan will further appreciate that changes can be introduced by mutation into the nucleotide sequence of SEQ ID NO:1, SEQ ID NO:3, SEQ ID NO:7, SEQ ID NO:9, SEQ ID NO:25, SEQ ID NO:26, SEQ ID NO:39, SEQ ID NO:41, SEQ ID NO:43, the cDNA of ATCC 203037, the cDNA of ATCC 203035, or the cDNA of ATCC 203036, thereby leading to changes in the amino acid sequence of the encoded CARD-3, CARD-4L/S protein, CARD-4 splice variant, or murine CARD-4 without altering the functional ability of the CARD-3, CARD-4L/S, CARD-4 splice variant, or murine CARD-4 protein. For example, one can make nucleotide substitutions leading to amino acid substitutions at "non-essential" amino acid residues. A "non-essential" amino acid residue is a residue that can be altered from the wild-type sequence of CARD-3, CARD-4L/S, CARD-4 splice variant, or murine CARD-4 protein (e.g., the sequence of SEQ ID NO:2, SEQ ID NO:8, SEQ ID NO:26, SEQ ID NO:40, SEQ ID NO:42 and SEQ ID NO:44) without altering the biological activity, whereas an "essential" amino acid residue is required for biological activity. For example, amino acid residues that are conserved among the CARD-3, CARD-4L/S, CARD-4 splice variant, or murine CARD-4 proteins of various species are predicted to be particularly unamenable to alteration.

For example, preferred CARD-3 or CARD-4 proteins of the present invention, contain at least one CARD domain. Additionally, a CARD-3 protein also contains at least one kinase domain or at least one linker domain. A CARD domain contains at least one nucleotide binding domain or Leucine-rich repeats. Such conserved domains are less likely to be amenable to mutation. Other amino acid residues, however, (e.g., those that are not conserved or only semi-conserved among CARD-3 or CARD-4 of various species) may not be essential for activity and thus are likely to be amenable to alteration.

Accordingly, another aspect of the invention pertains to nucleic acid molecules encoding CARD-3 or CARD-4 proteins that contain changes in amino acid residues that are not essential for activity. Such CARD-3 or CARD-4 proteins differ in amino acid sequence from SEQ ID NO:2, SEQ ID NO:8, SEQ ID NO:25, SEQ ID NO:40, SEQ ID NO:42, or SEQ ID NO:44 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, SEQ ID NO:8, SEQ ID NO:26, SEQ ID NO:40, SEQ ID NO:42 or SEQ ID NO:44.

An isolated nucleic acid molecule encoding a CARD-3 or CARD-4 proteins having a sequence which differs from that of SEQ ID NO:2, SEQ ID NO:8, SEQ ID NO:26, SEQ ID NO:40, SEQ ID NO:42 or SEQ ID NO:44, can be created by introducing one or more nucleotide substitutions, additions or deletions into the nucleotide sequence of CARD-3 (SEQ ID NO:1, SEQ ID NO:3, the cDNA of ATCC 203037) or CARD-4L (SEQ ID NO:7, SEQ ID NO:9, the cDNA of ATCC 203035), or CARD-4S (SEQ ID NO:25, SEQ ID NO:27, the cDNA of ATCC 203036), or murine CARD-4 (SEQ ID NO:43) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in CARD-3 or CARD-4 is preferably replaced with another amino acid residue from the same side chain family. Alternatively, mutations can be introduced randomly along all or part of a CARD-3 or CARD-4 coding sequence, such as by saturation mutagenesis, and the resultant mutants can be screened for CARD-3 or CARD-4 biological activity to identify mutants that retain activity. Following mutagenesis, the encoded protein can be expressed recombinantly and the activity of the protein can be determined.

In an embodiment, a mutant CARD-3 or CARD-4 protein can be assayed for: (1) the ability to form protein:protein interactions with proteins in the apoptotic signaling pathway; (2) the ability to bind a CARD-3 or CARD-4 ligand; or (3) the ability to bind to an intracellular target protein. For example, in Example 12, CARD-4 is shown to physically associate with the apoptotic pathway proteins caspase 9 and BCLX. For example, (1) in Example 7, a two-hybrid screening assay for the physical interaction of CARD-3 and CARD-4 is shown, (2) in Example 8, a two-hybrid system assay for the interaction between CARD-4 and its ligand hNUDC is described, and (3) in Example 12, coimmuno-precipitations assays for the interaction of CARD-3 with its ligand CARD-4 and for CARD-4 with its ligands CARD-3, CARD-4, caspase 9, and BCLX are shown. In yet another embodiment, a mutant CARD-3 or CARD-4 protein can be assayed for the ability to modulate cellular proliferation, cellular differentiation, or cellular death. For example, in Example 10, assays for the regulation of cellular death (apoptosis) are described. In yet another embodiment, a mutant CARD-3 or CARD-4 protein can be assayed for regulation of a cellular signal transduction pathway. For example, in Example 9, an assay for the regulation by CARD-4 of the NF-κB pathway is described.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CARD-3 or CARD-4 coding strand, or to only a portion thereof, e.g., all or part of the protein coding region (or open reading frame). An antisense nucleic acid molecule can be antisense to a noncoding region of the coding strand of a nucleotide sequence encoding CARD-3 or CARD-4. The noncoding regions ("5' and 3' untranslated regions") are the 5' and 3' sequences which flank the coding region and are not translated into amino acids.

Given the coding strand sequences encoding CARD-3 or CARD-4 disclosed herein (e.g., SEQ ID NO:1, SEQ ID NO:3, SEQ ID NO:7, SEQ ID NO:9, SEQ ID NO:25, SEQ ID NO:27, SEQ ID NO:38, SEQ ID NO:40, or SEQ ID NO:42), antisense nucleic acids of the invention can be designed according to the rules of Watson and Crick base pairing. The antisense nucleic acid molecule can be complementary to the entire coding region of CARD-3 or CARD-4L/S mRNA, but more preferably is an oligonucleotide which is antisense to only a portion of the coding or noncoding region of CARD-3 or CARD-4 mRNA. For example, the antisense oligonucleotide can be complementary to the region surrounding the translation start site of CARD-3 mRNA, e.g., an oligonucleotide having the sequence CCCTGGTACTTGCCCCTCCGGTAG (SEQ ID NO:34) or CCTGGTACTTGCCCCTCC (SEQ ID NO:35) or of the CARD-4L mRNA e.g., TCGTTAAGCCCTTGAA-GACAGTG (SEQ ID NO:36) and TCGTTAGCCCTTGAA-GACCAGTGAGTGTAG (SEQ ID NO:37). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxy-carboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARD-3 or CARD-4 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CARD-3 or CARD-4 mRNA transcripts to thereby inhibit translation of CARD-3 or CARD-4 mRNA. A ribozyme having specificity for a CARD-3 or CARD-4-encoding nucleic acid can be designed based upon the nucleotide sequence of a CARD-3 or CARD-4 cDNA disclosed herein (e.g., SEQ ID NO:1, SEQ ID NO:3, SEQ ID NO:7, SEQ ID NO:9, SEQ ID NO:25, SEQ ID NO:27, SEQ ID NO:39, SEQ ID NO:41, and SEQ ID NO:43). For example, a derivative of a Tetrahymena L-19 IVS RNA can be constructed in which the nucleotide sequence of the active site is complementary to the nucleotide sequence to be cleaved in a CARD-3 or CARD-4-encoding mRNA. See, e.g., Cech et al. U.S. Pat. No. 4,987,071; and Cech et al. U.S. Pat. No. 5,116,742. Alternatively, CARD-3 or CARD-4 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, CARD-3 or CARD-4 gene expression can be inhibited by targeting nucleotide sequences complementary to the regulatory region of the CARD-3 or CARD-4 (e.g., the CARD-3 or CARD-4 promoter and/or enhancers) to form triple helical structures that prevent transcription of the CARD-3 or CARD-4 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In preferred embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93: 14670–675.

PNAs of CARD-3 or CARD-4 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-3 or CARD-4 can also be used, e.g., in the analysis of single base pair mutations in a gene by, e.g., PNA directed PCR clamping; as 'artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of CARD-3 or CARD-4 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-3 or CARD-4 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in viva), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated CARD-3 or CARD-4 Proteins and Anti-CARD-3 or CARD-4 Antibodies

One aspect of the invention pertains to isolated CARD-3 or CARD-4 proteins, and biologically active portions thereof, as well as polypeptide fragments suitable for use as immunogens to raise anti-CARD-3 or CARD-4 antibodies. In one embodiment, native CARD-3 or CARD-4 proteins can be isolated from cells or tissue sources by an appropriate purification scheme using standard protein purification techniques. In another embodiment, CARD-3 or CARD-4 proteins are produced by recombinant DNA techniques. Alternative to recombinant expression, a CARD-3 or CARD-4 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-3 or CARD-4 protein is derived, or substantially free from chemical precursors or other chemicals when chemically synthesized. The language "substantially free of cellular material" includes preparations of CARD-3 or CARD-4 protein in which the protein is separated from cellular components of the cells from which it is isolated or recombinantly produced. Thus, CARD-3 or CARD-4 protein that is substantially free of cellular material includes preparations of CARD-3 or CARD-4 protein having less than about 30%, 20%, 10%, or 5% (by dry weight) of non-CARD-3 or CARD-4 protein (also referred to herein as a "contaminating protein"). When the CARD-3 or CARD-4 protein or biologically active portion thereof is recombinantly produced, it is also preferably substantially free of culture medium, i.e., culture medium represents less than about 20%, 10%, or 5% of the volume of the protein preparation. When CARD-3 or CARD-4 protein is produced by chemical synthesis, it is preferably substantially free of chemical precursors or other chemicals, i.e., it is separated from chemical precursors or other chemicals which are involved in the synthesis of the protein. Accordingly such preparations of CARD-3 or CARD-4 protein have less than about 30%, 20%, 10%, 5% (by dry weight) of chemical precursors or non-CARD-3 or CARD-4 chemicals.

Biologically active portions of a CARD-3 or CARD-4 protein include peptides comprising amino acid sequences sufficiently identical to or derived from the amino acid sequence of the CARD-3 or CARD-4 protein (e.g., the amino acid sequence shown in SEQ ID NO:2, SEQ ID NO:8, SEQ ID NO:26, SEQ ID NO:38, SEQ ID NO:40 or SEQ ID NO:42), which include less amino acids than the full length CARD-3 or CARD-4 proteins, and exhibit at least one activity of a CARD-3 or CARD-4 protein. Typically, biologically active portions comprise a domain or motif with at least one activity of the CARD-3 or CARD-4 protein. A biologically active portion of a CARD-3 or CARD-4 protein can be a polypeptide which is, for example, 10, 25, 50, 100 or more amino acids in length. Preferred biologically active polypeptides include one or more identified CARD-3 or CARD-4 structural domains, e.g., the CARD domain (SEQ ID NO:6 or SEQ ID NO:10 or SEQ ID NO:26).

Moreover, other biologically active portions, in which other regions of the protein are deleted, can be prepared by recombinant techniques and evaluated for one or more of the functional activities of a native CARD-3 or CARD-4 protein.

CARD-33 or CARD-4 protein has the amino acid sequence shown of SEQ ID NO:2, SEQ ID NO:8, SEQ ID NO:26, SEQ ID NO:39, SEQ ID NO:41 or SEQ ID NO:43. Other useful CARD-3 or CARD-4 proteins are substantially identical to SEQ ID NO:2 or SEQ ID NO:8 or SEQ ID NO:26, SEQ ID NO:39 or SEQ ID NO:41 or SEQ ID NO:43 and retain the functional activity of the protein of SEQ ID NO:2 or SEQ ID NO:8 or SEQ ID NO:26, SEQ ID NO:39 or SEQ ID NO:41 or SEQ ID NO:43 yet differ in amino acid sequence due to natural allelic variation or mutagenesis. CARD-3 and CARD-4 are involved in activating caspases in the apoptotic pathway. For example, in Example 10, CARD-4 is shown to enhance caspase 9 activity. Accordingly, a useful CARD-3 or CARD-4 protein is a protein which includes an amino acid sequence at least about 45%, preferably 55%, 65%, 75%, 85%, 95%, or 99% identical to the amino acid sequence of SEQ ID NO:2 or SEQ ID NO:8 or SEQ ID NO:26, SEQ ID NO:39 or SEQ ID NO:41 or SEQ ID NO:43 and retains the functional activity of the CARD-3 or CARD-4 proteins of SEQ ID NO:2 or SEQ ID NO:8 or SEQ ID NO:26, SEQ ID NO:39 or SEQ ID NO:41 or SEQ ID NO:43. In other instances, the CARD-3 or CARD-4 protein is a protein having an amino acid sequence 55%, 65%, 75%, 85%, 95%, or 98% identical to the CARD-3 or CARD-4L CARD domain (SEQ ID NO:6, SEQ ID NO:10 and SEQ ID NO:26). In an embodiment, the CARD-3 or CARD-4 protein retains a functional activity of the CARD-3 or CARD-4 protein of SEQ ID NO:2, SEQ ID NO:8 or SEQ ID NO:26, SEQ ID NO:39 or SEQ ID NO:41 or SEQ ID NO:43.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to CARD-3 or CARD-4 nucleic acid molecules of the invention. For example, Example 5 describes the use of the TBLASTN program to query a database of sequences of full length and partial cDNA sequences with the human CARD-4 polypeptide sequence leading to the discovery of murine CARD-4 and Example 4 describes the use of BLASTN to query a proprietary EST database with the 5' untranslated sequence of CARD-4 leading to the discovery of two human CARD-4 splice variants. BLAST protein searches can be performed with the XBLAST program, score=50, wordlength=3 to obtain amino acid sequences homologous to CARD-3 or CARD-4 protein molecules of the invention. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides CARD-3 or CARD-4 chimeric or fusion proteins. As used herein, a CARD-3 or CARD-4 "chimeric protein" or "fusion protein" comprises a CARD-3 or CARD-4 polypeptide operatively linked to a non-CARD-3 or CARD-4 polypeptide. A "CARD-3 or CARD-4 polypeptide" refers to a polypeptide having an amino acid sequence corresponding to CARD-3 or CARD-4L/S, murine CARD-4 or human CARD-4 splice variants, whereas a "non-CARD-3 or CARD-4 polypeptide" refers to a polypeptide having an amino acid sequence corresponding to a protein which is not substantially identical to the CARD-3 or CARD-4L/S protein, murine CARD-4, or human CARD-4 splice variants e.g., a protein which is different from the CARD-3 or CARD-4 proteins and which is derived from the same or a different organism. Within a CARD-3 or CARD-4L fusion protein, the CARD-3 or CARD-4 polypeptide can correspond to all or a portion of a CARD-3 or CARD-4 protein, preferably at least one biologically active portion of a CARD-3 or CARD-4 protein. Within the fusion protein, the term "operatively linked" is intended to indicate that the CARD-3 or CARD-4 polypeptide and the non-CARD-3 or non-CARD-4 polypeptide are fused in-frame to each other. The non-CARD-3 or non-CARD-4 polypeptide can be fused to the N-terminus or C-terminus of the CARD-3 or CARD-4 polypeptide.

One useful fusion protein is a GST-CARD-3 or GST-CARD-4 fusion protein in which the CARD-3 or CARD-4 sequences are fused to the C-terminus of the GST sequences. Such fusion proteins can facilitate the purification of recombinant CARD-3 or CARD-4.

In another embodiment, the fusion protein contains a signal sequence from another protein. In certain host cells (e.g., mammalian host cells), expression and/or secretion of CARD-3 or CARD-4 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a CARD-3 or CARD-4-immunoglobulin fusion protein in which all or part of CARD-3 or CARD-4 is fused to sequences derived from a member of the immunoglobulin protein family. The CARD-3 or CARD-4-immunoglobulin fusion proteins of the invention can be incorporated into pharmaceutical compositions and administered to a subject to inhibit an interaction between a CARD-3 or CARD-4 ligand and a CARD-3 or CARD-4 protein on the surface of a cell, to thereby suppress CARD-3 or CARD-4-mediated signal transduction in vivo. The CARD-3 or CARD-4-immunoglobulin fusion proteins can be used to affect the bioavailability of a CARD-3 or CARD-4 cognate ligand. Inhibition of the CARD-3 ligand/CARD-3 or CARD-4 ligand/CARD-4 interaction may be useful therapeutically for both the treatment of proliferative and differentiative disorders, as well as modulating (e.g. promoting or inhibiting) cell survival. Moreover, the CARD-3 or CARD-4-immunoglobulin fusion proteins of the invention can be used as immunogens to produce anti-CARD-3 or CARD-4 antibodies in a subject, to purify CARD-3 or CARD-4 ligands and in screening assays to identify molecules which inhibit the interaction of CARD-3 or CARD-4 with a CARD-3 or CARD-4 ligand.

Preferably, a CARD-3 or CARD-4 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-3 or CARD-4-encoding nucleic acid can be cloned into such an expression vector such that the fusion moiety is linked in-frame to the CARD-3 or CARD-4 protein.

The present invention also pertains to variants of the CARD-3 or CARD-4 proteins which function as either CARD-3 or CARD-4 agonists (mimetics) or as CARD-3 or CARD-4 antagonists. Variants of the CARD-3 or CARD-4 protein can be generated by mutagenesis, e.g., discrete point mutation or truncation of the CARD-3 or CARD-4 protein. An agonist of the CARD-3 or CARD-4 protein can retain substantially the same, or a subset, of the biological activities of the naturally occurring form of the CARD-3 or CARD-4 protein. An antagonist of the CARD-3 or CARD-4 protein can inhibit one or more of the activities of the naturally occurring form of the CARD-3 or CARD-4 protein by, for example, competitively binding to a downstream or upstream member of a cellular signaling cascade which includes the CARD-3 or CARD-4 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-3 or CARD-4 proteins.

Variants of the CARD-3 or CARD-4 protein which function as either CARD-3 or CARD-4 agonists (mimetics) or as CARD-3 or CARD-4 antagonists can be identified by screening combinatorial libraries of mutants, e.g., truncation mutants of the CARD-3 or CARD-4 protein for CARD-3 or CARD-4 protein agonist or antagonist activity. In one embodiment, a variegated library of CARD-3 or CARD-4 variants is generated by combinatorial mutagenesis at the nucleic acid level and is encoded by a variegated gene library. A variegated library of CARD-3 or CARD-4 variants can be produced by, for example, enzymatically ligating a mixture of synthetic oligonucleotides into gene sequences such that a degenerate set of potential CARD-3 or CARD-4 sequences is expressible as individual polypeptides, or alternatively, as a set of larger fusion proteins (e.g., for phage display) containing the set of CARD-3 or CARD-4 sequences therein. There are a variety of methods which can be used to produce libraries of potential CARD-3 or CARD-4 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-3 or CARD-4 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the CARD-3 or CARD-4 protein coding sequence can be used to generate a variegated population of CARD-3 or CARD-4 fragments for screening and subsequent selection of variants of a CARD-3 or CARD-4 protein. In one embodiment, a library of coding sequence fragments can be generated by treating a double stranded PCR fragment of a CARD-3 or CARD-4 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-3 or CARD-4 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-3 or CARD-4 proteins. The most widely used techniques, which are amenable to high through-put analysis, for screening large gene libraries typically include cloning the gene library into replicable expression vectors, transforming appropriate cells with the resulting library of vectors, and expressing the combinatorial genes-under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-3 or CARD-4 variants (Arkin and Yourvan (1992) Proc. Natl. Acad. Sci. USA 89:7811–7815; Delgrave et al. (1993) Protein Engineering 6(3):327–331).

An isolated CARD-3 or CARD-4 protein, or a portion or fragment thereof, can be used as an immunogen to generate antibodies that bind CARD-3 or CARD-4 using standard techniques for polyclonal and monoclonal antibody preparation. The full-length CARD-3 or CARD-4 protein can be used or, alternatively, the invention provides antigenic peptide fragments of CARD-3 or CARD-4 for use as immunogens. The antigenic peptide of CARD-3 or CARD-4 comprises at least 8 (preferably 10, 15, 20, or 30) amino acid residues of the amino acid sequence shown in SEQ ID NO:2, SEQ ID NO:8 or SEQ ID NO:26, or SEQ ID NO:40 or SEQ ID NO:42 or SEQ ID NO:44 or polypeptides including amino acids 128–139 or 287–298 of human CARD-4L and encompasses an epitope of CARD-3 or CARD-4 such that an antibody raised against the peptide forms a specific immune complex with CARD-3 or CARD-4.

Figure 9:
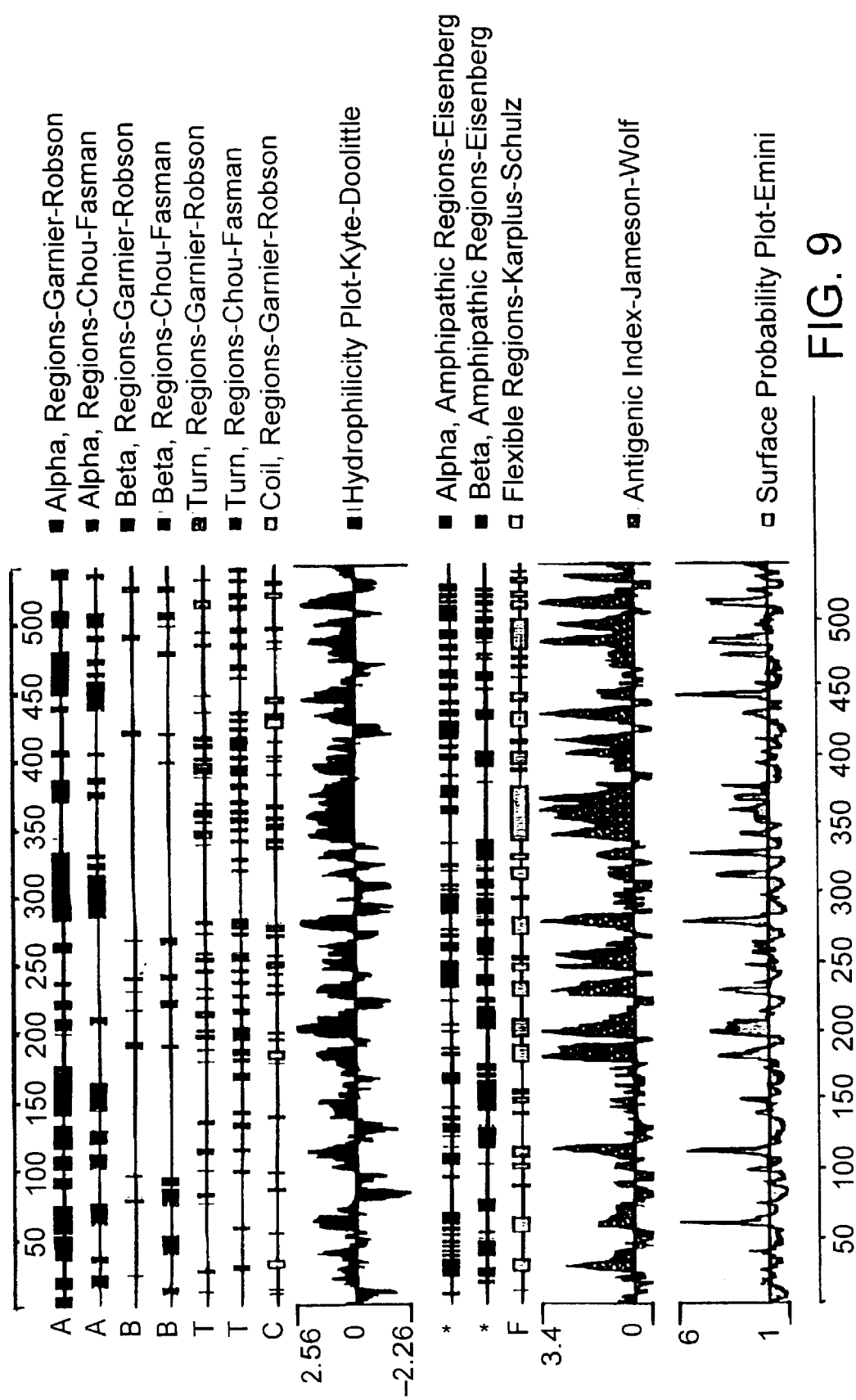
FIG. 9 is a plot showing predicted structural features of human CARD-4S.
Figure 14A:
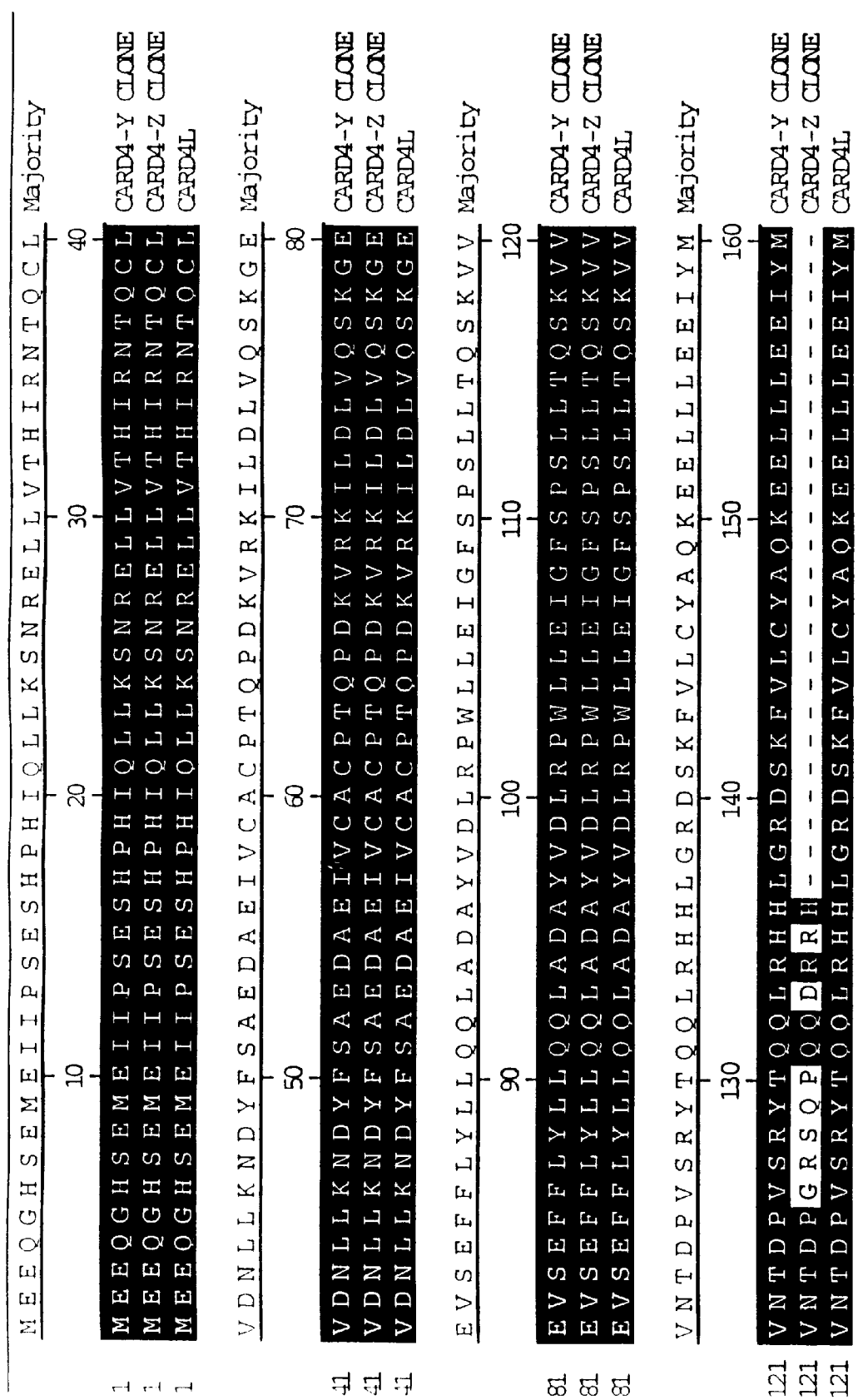
Figure 14C:
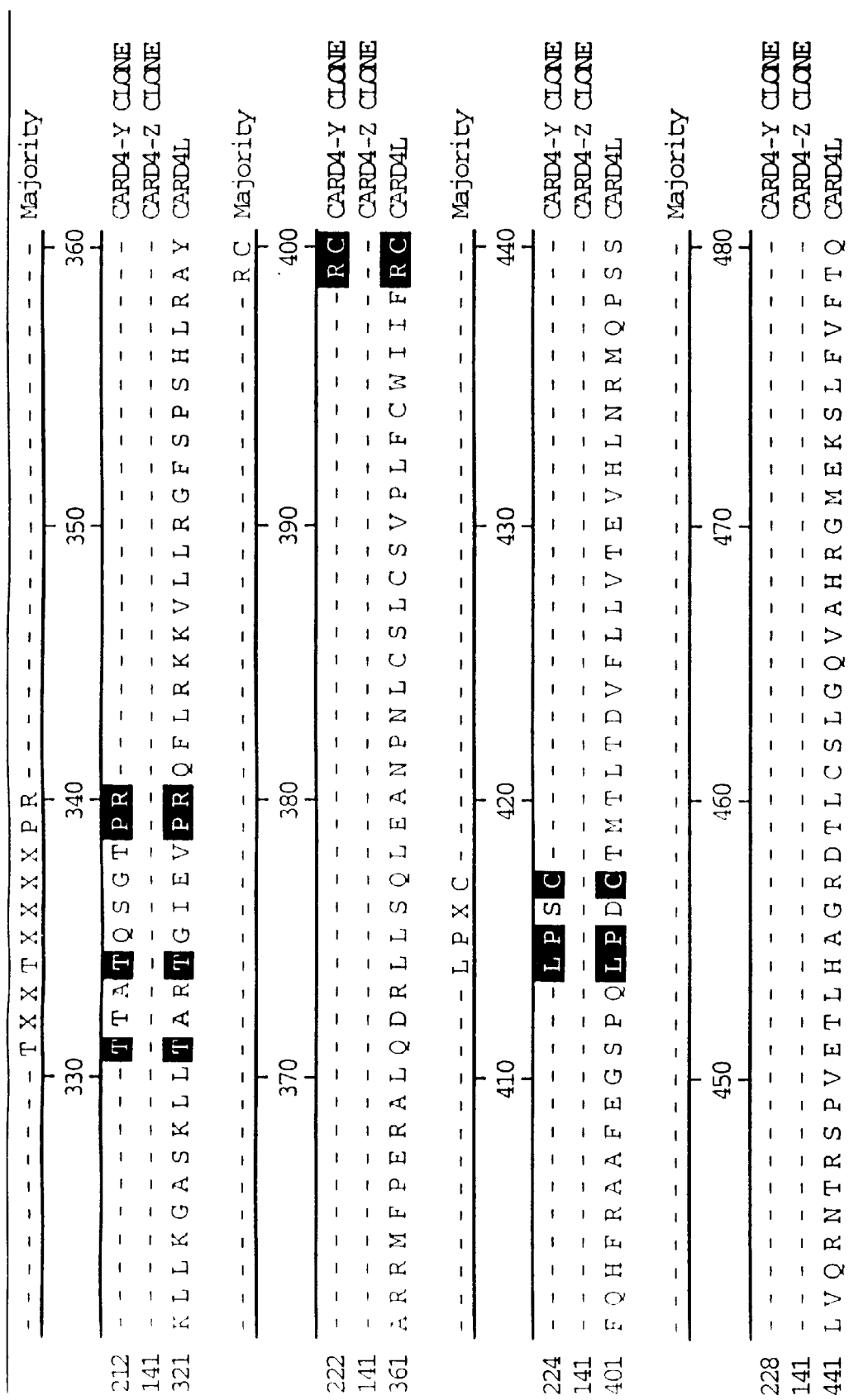
Figure 14D:
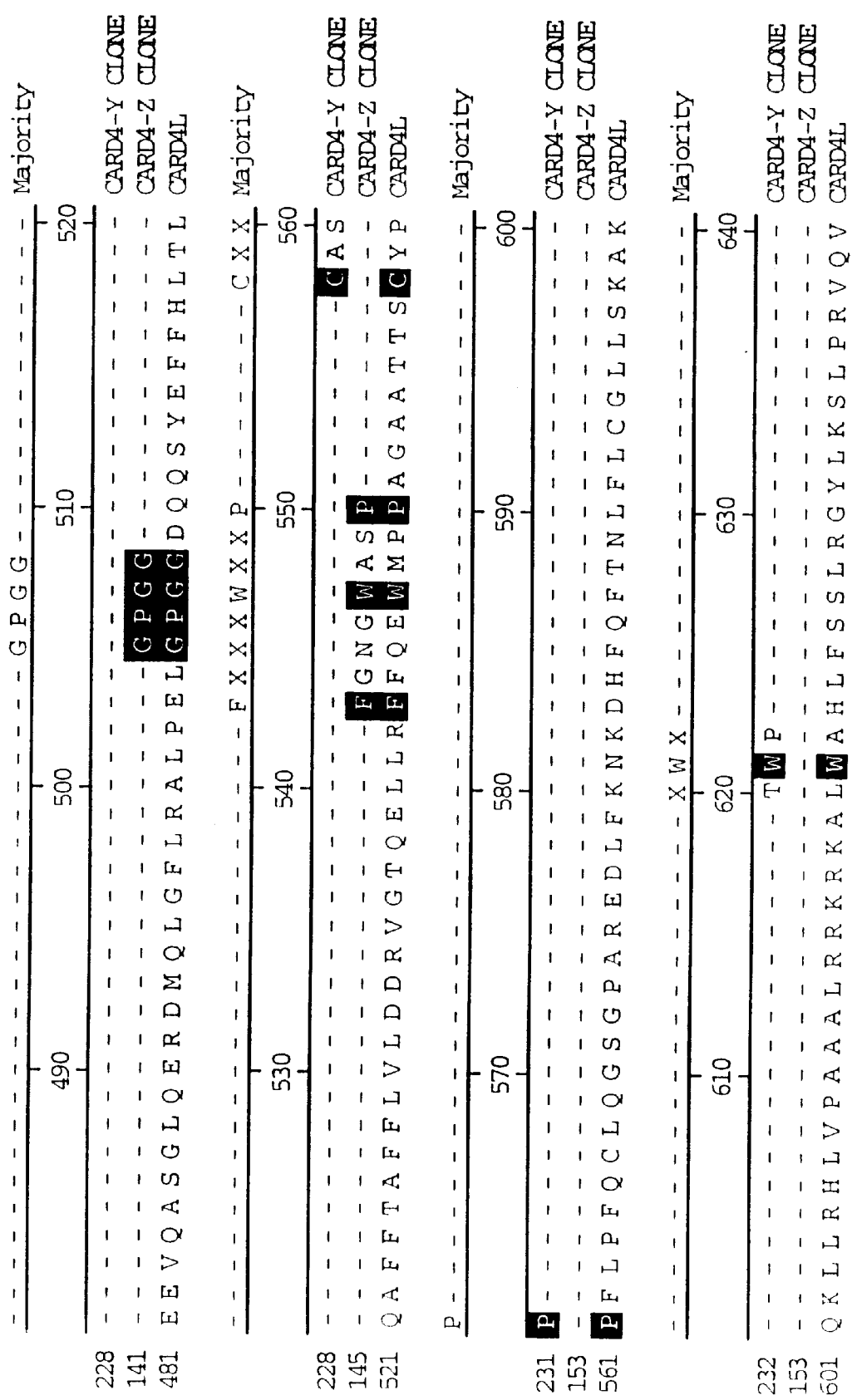
Figure 14E:
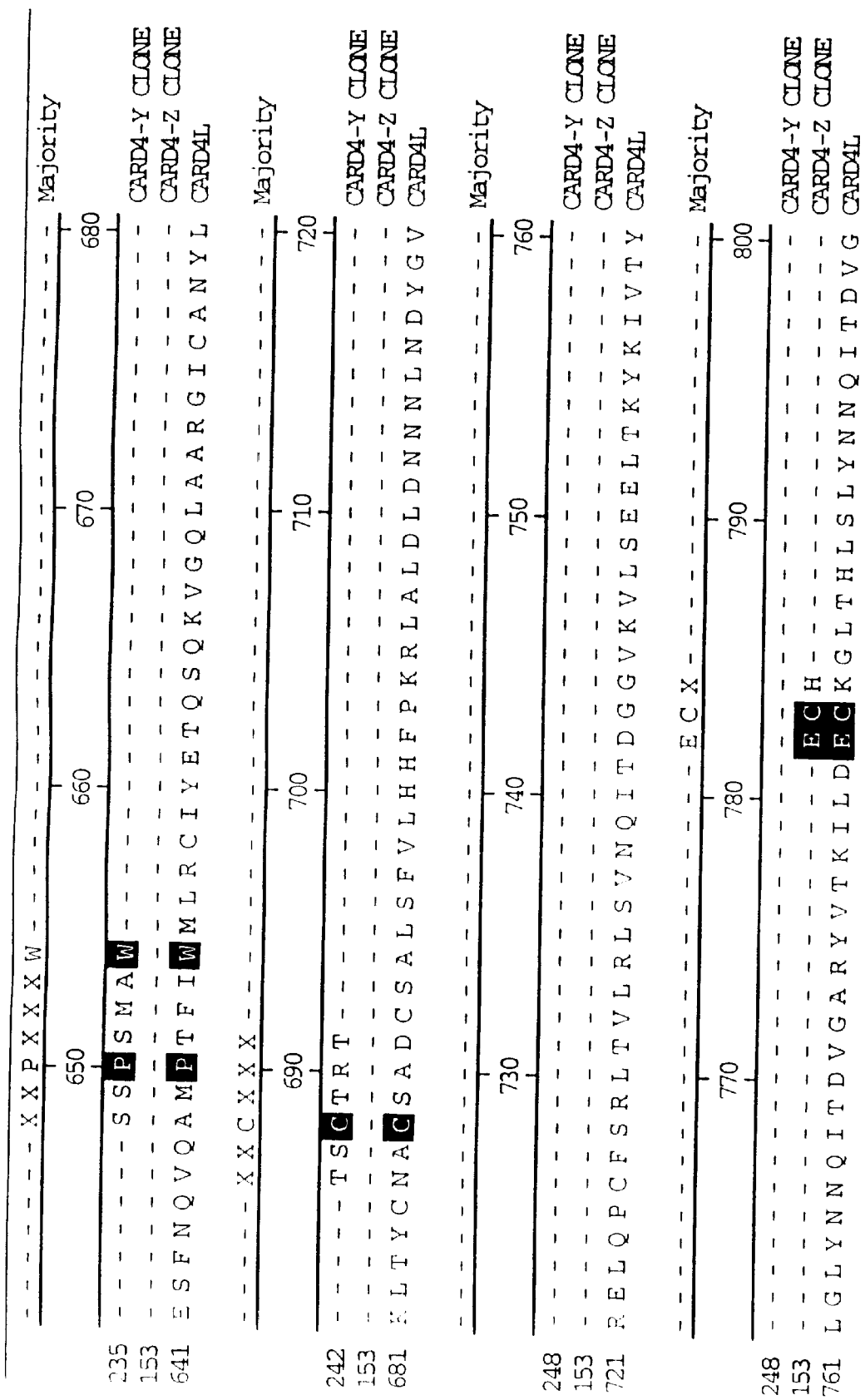
Figure 14F:
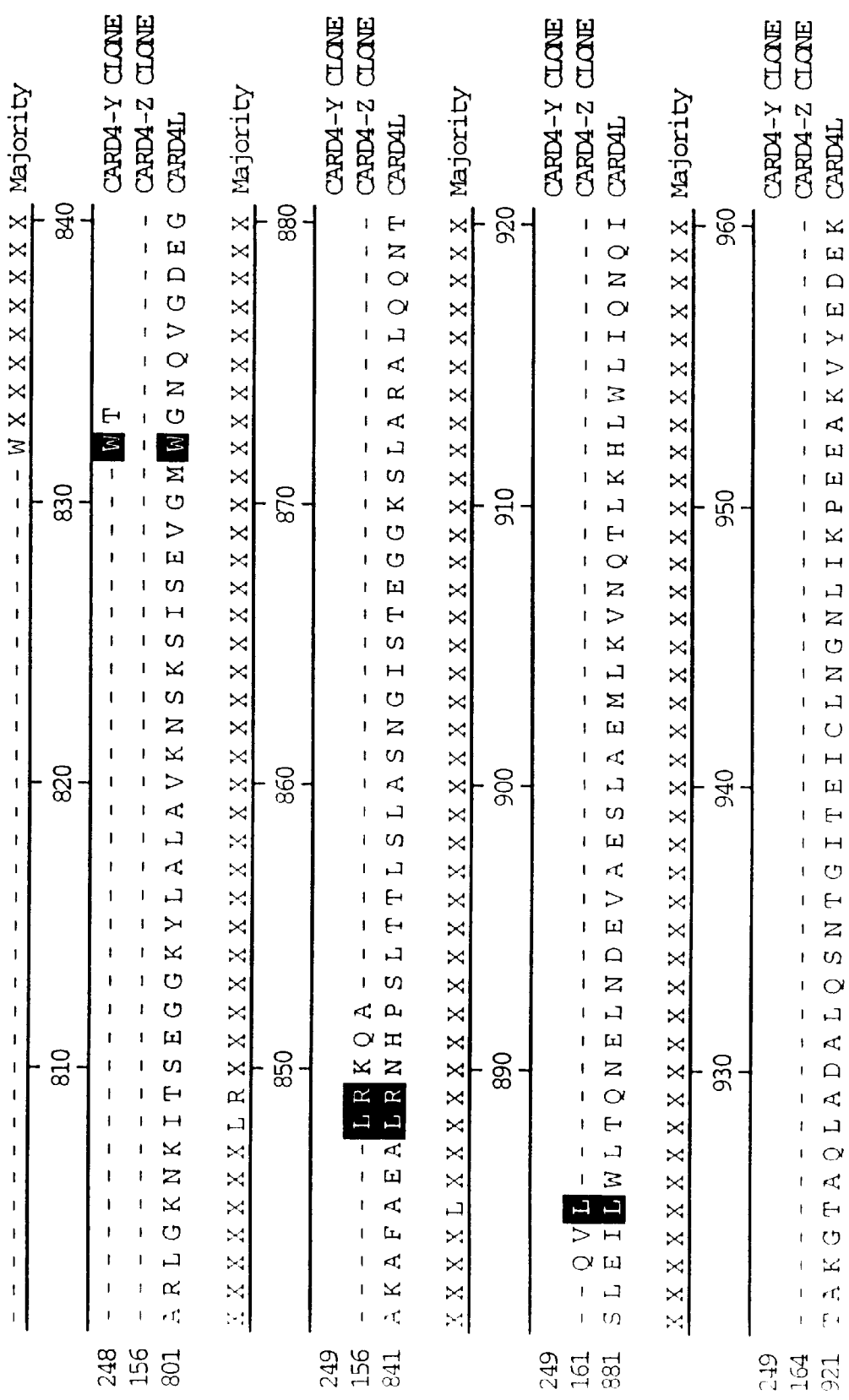

Preferred epitopes encompassed by the antigenic peptide are regions of CARD-3 or CARD-4 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIG. 8 and FIG. 9).

A CARD-3 or CARD-4 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-3 or CARD-4 protein or a chemically synthesized CARD-3 or CARD-4 polypeptide. The preparation can further include an adjuvant, such as Freund's complete or incomplete adjuvant, or similar immunostimulatory agent. Immunization of a suitable subject with an immunogenic CARD-3 or CARD-4 preparation induces a polyclonal anti-CARD-3 or CARD-4 antibody response. For example, polypeptides including amino acids 128–139 or 287–298 of human CARD-4L were conjugated to KLH and the resulting conjugates were used to immunize rabbits and polyclonal antibodies that specifically recognize the two immunogen peptides were generated.

Accordingly, another aspect of the invention pertains to anti-CARD-3 or CARD-4 antibodies. The term "antibody" as used herein refers to immunoglobulin molecules and immunologically active portions of immunoglobulin molecules, i.e., molecules that contain an antigen binding site which specifically binds an antigen, such as CARD-3 or CARD-4. A molecule which specifically binds to CARD-3 or CARD-4 is a molecule which binds CARD-3 or CARD-4, but does not substantially bind other molecules in a sample, e.g., a biological sample, which naturally contains CARD-3 or CARD-4. Examples of immunologically active portions of immunoglobulin molecules include F(ab) and F(ab')2 fragments which can be generated by treating the antibody with an enzyme such as pepsin. The invention provides polyclonal and monoclonal antibodies that bind CARD-3 or CARD-4. The term "monoclonal antibody" or "monoclonal antibody composition", as used herein, refers to a population of antibody molecules that contain only one species of an antigen binding site capable of immunoreacting with a particular epitope of CARD-3 or CARD-4. A monoclonal antibody composition thus typically displays a single binding affinity for a particular CARD-3 or CARD-4 protein with which it immunoreacts.

Polyclonal anti-CARD-3 or CARD-4 antibodies can be prepared as described above by immunizing a suitable subject with a CARD-3 or CARD-4 immunogen. The anti-CARD-3 or CARD-4 antibody titer in the immunized subject can be monitored over time by standard techniques, such as with an enzyme linked immunosorbent assay (ELISA) using immobilized CARD-3 or CARD-4. If desired, the antibody molecules directed against CARD-3 or CARD-4 can be isolated from the mammal (e.g., from the blood) and further purified by well-known techniques, such as protein A chromatography to obtain the IgG fraction. At an appropriate time after immunization, e.g., when the anti-CARD-3 or CARD-4 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CARD-3 or CARD-4 immunogen as described above, and the culture supernatants of the resulting hybridoma cells are screened to identify a hybridoma producing a monoclonal antibody that binds CARD-3 or CARD-4.

Any of the many well known protocols used for fusing lymphocytes and immortalized cell lines can be applied for the purpose of generating an anti-CARD-3 or CARD-4 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/0-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-3 or CARD-4, e.g., using a standard ELISA assay.

Alternative to preparing monoclonal antibody-secreting hybridomas, a monoclonal anti-CARD-3 or CARD-4 antibody can be identified and isolated by screening a recombinant combinatorial immunoglobulin library (e.g., an antibody phage display library) with CARD-3 or CARD-4 to thereby isolate immunoglobulin library members that bind CARD-3 or CARD-4. Kits for generating and screening phage display libraries are commercially available (e.g., the Pharmacia Recombinant Phage Antibody System, Catalog No. 27-9400-01; and the Stratagene SurfZAP? Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J 12:725–734.

Additionally, recombinant anti-CARD-3 or CARD-4 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125, 023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225, 539; Jones et al. (1986) Nature 321:552–525; Verhoeyan et al. (1988) Science 239:1534; and Beidler et al. (1988) J. Immunol. 141:4053–4060.

An anti-CARD-3 or CARD-4 antibody (e.g., monoclonal antibody) can be used to isolate CARD-3 or CARD-4 by standard techniques, such as affinity chromatography or immunoprecipitation. An anti-CARD-3 or CARD-4 antibody can facilitate the purification of natural CARD-3 or CARD-4 from cells and of recombinantly produced CARD-3 or CARD-4 expressed in host cells. Moreover, an anti-CARD-3 or CARD-4 antibody can be used to detect CARD-3 or CARD-4 protein (e.g., in a cellular lysate or cell supernatant) in order to evaluate the abundance and pattern of expression of the CARD-3 or CARD-4 protein. Anti-CARD-3 or CARD-4 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding CARD-3 or CARD-4 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CARD-3 or CARD-4 proteins, mutant forms of CARD-3 or CARD-4, fusion proteins, etc.).

The recombinant expression vectors of the invention can be designed for expression of CARD-3 or CARD-4 in prokaryotic or eukaryotic cells, e.g., bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include AGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301–315) and pET lid (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident ? prophage harboring a T7 gn1 gene under the transcriptional control of the lacUV5 promoter.

One strategy to maximize recombinant protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111–2118). Such alteration of nucleic acid sequences of the invention can be carried out by standard DNA synthesis techniques.

In another embodiment, the CARD-3 or CARD-4 expression vector is a yeast expression vector. Examples of vectors for expression in yeast *S. cerivisae* include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (InVitrogen Corp, San Diego, Calif.). For example, in Example 7 the expression of a fusion protein comprising amino acids 1–145 of human CARD-4L fused to the DNA-binding domain of *S. cerevisiae* transcription factor GAL4 from the yeast expression vector pGBT9 is described. In another example, Example 8 describes the expression of a fusion protein comprising amino acids 406–953 of human CARD-4L fused to the DNA-binding domain of *S. cerevisiae* transcription factor GAL4 from the yeast expression vector pGBT9. In yet another example, Example 7 describes the expression of a fusion protein comprising CARD-3 fused to the transcriptional activation domain of *S. cerevisiae* transcription factor GAL4 from the yeast expression vector pACTII.

Alternatively, CARD-3 or CARD-4 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra). For example, Example 9, Example 10, and Example 12 describe the expression of human CARD-4 or fragments thereof, CARD-3, or both from the mammalian expression vector pCI.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARD-3 or CARD-4 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-3 or CARD-4 protein can be expressed in bacterial cells such as E. coli, insect cells, yeast or mammalian cells (such as Chinese hamster ovary cells (CHO) or COS cells). Other suitable host cells are known to those skilled in the art. For example, in Example 7 a Saccharomyces cerevisiae host cell for recombinant CARD-4 and CARD-3 expression is described and in Examples 9, 10, and 12 293T host cells for expression of CARD4 or fragments thereof or CARD-3 are described.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-3 or CARD-4 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a (i.e., express) CARD-3 or CARD-4 protein. Accordingly, the invention further provides methods for producing CARD-3 or CARD-4 protein using the host cells of the invention. In one embodiment, the method comprises culturing the host cell of invention (into which a recombinant expression vector encoding CARD-3 or CARD-4 has been introduced) in a suitable medium such that CARD-3 or CARD-4 protein is produced. In another embodiment, the method further comprises isolating CARD-3 or CARD-4 from the medium or the host cell.

The host cells of the invention can also be used to produce nonhuman transgenic animals. For example, in one embodiment, a host cell of the invention is a fertilized oocyte or an embryonic stem cell into which CARD-3 or CARD-4-coding sequences have been introduced. Such host cells can then be used to create non-human transgenic animals in which exogenous CARD-3 or CARD-4 sequences have been introduced into their genome or homologous recombinant animals in which endogenous CARD-3 or CARD-4 sequences have been altered. Such animals are useful for studying the function and/or activity of CARD-3 or CARD-4 and for identifying and/or evaluating modulators of CARD-3 or CARD-4 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-3 or CARD-4 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-3 or CARD-4-encoding nucleic acid into the male pronuclei of a fertilized oocyte, e.g., by microinjection, retroviral infection, and allowing the oocyte to develop in a pseudopregnant female foster animal. The CARD-3 or CARD-4 cDNA sequence e.g., that of (SEQ ID NO:1, SEQ ID NO:3, SEQ ID NO:7, SEQ ID NO:9, SEQ ID NO:25, SEQ ID NO:27, SEQ ID NO:39, SEQ ID NO:41, SEQ ID NO:43 or the cDNA of ATCC 203037, or the cDNA of ATCC 203035, or the cDNA of ATCC 203036) can be introduced as a transgene into the genome of a non-human animal. Alternatively, a nonhuman homolog or ortholog of the human CARD-3 or CARD-4 gene, such as a mouse CARD-3 or CARD-4 gene, can be isolated based on hybridization to the human CARD-3 or CARD-4 cDNA and used as a transgene. For example, the mouse ortholog of CARD-4, FIGS. 15A–15C and SEQ ID NO:43 can be used to make a transgenic animal using standard methods. Intronic sequences and polyadenylation signals can also be included in the transgene to increase the efficiency of expression of the transgene. A tissue-specific regulatory sequence(s) can be operably linked to the CARD-3 or CARD-4 transgene to direct expression of CARD-3 or CARD-4 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-3 or CARD-4 transgenic in its genome and/or expression of CARD-3 or CARD-4 mRNA in tissues or cells of the animals. A transgenic founder animal can then be used to breed additional animals carrying the transgene. Moreover, transgenic animals carrying a transgene encoding CARD-3 or CARD-4 can further be bred to other transgenic animals carrying other transgenes.

To create an homologous recombinant animal, a vector is prepared which contains at least a portion of a CARD-3 or CARD-4 gene (e.g., a human or a non-human homolog of the CARD-3 or CARD-4 gene, e.g., a murine CARD-3 or CARD-4 gene) into which a deletion, addition or substitution has been introduced to thereby alter, e.g., functionally disrupt, the CARD-3 or CARD-4 gene. In an embodiment, the vector is designed such that, upon homologous recombination, the endogenous CARD-3 or CARD-4 gene is functionally disrupted (i.e., no longer encodes a functional protein; also referred to as a "knock out" vector). Alternatively, the vector can be designed such that, upon homologous recombination, the endogenous CARD-3 or CARD-4 gene is mutated or otherwise altered but still encodes functional protein (e.g., the upstream regulatory region can be altered to thereby alter the expression of the endogenous CARD-3 or CARD-4 protein). In the homologous recombination vector, the altered portion of the CARD-3 or CARD-4 gene is flanked at its 5' and 3' ends by additional nucleic acid of the CARD-3 or CARD-4 gene to allow for homologous recombination to occur between the exogenous CARD-3 or CARD-4 gene carried by the vector and an endogenous CARD-3 or CARD-4 gene in an embryonic stem cell. The additional flanking CARD-3 or CARD-4 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-3 or CARD-4 gene has homologously recombined with the endogenous CARD-3 or CARD-4 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided-through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The

IV. Pharmaceutical Compositions offspring borne of this female foster animal will be a clone of the animal from which the cell, e.g., the somatic cell, is isolated.

The CARD-3 or CARD-4 nucleic acid molecules, CARD-3 or CARD-4 proteins, and anti-CARD-3 or CARD-4 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, Fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL? (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-3 or CARD-4 protein or anti-CARD-3 or CARD-4 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A CARD-3 or CARD-4 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-3 or CARD-4 protein (e.g., via a recombinant expression vector in a host cell in gene therapy applications), to detect CARD-3 or CARD-4 mRNA (e.g., in a biological sample) or a genetic lesion in a CARD-3 or CARD-4 gene, and to modulate CARD-3 or CARD-4 activity. In addition, the CARD-3 or CARD-4 proteins can be used to screen drugs or compounds which modulate the CARD-3 or CARD-4 activity or expression as well as to treat disorders characterized by insufficient or excessive production of CARD-3 or CARD-4 protein or production of CARD-3 or CARD-4 protein forms which have decreased or aberrant activity compared to CARD-3 or CARD-4 wild type protein. In addition, the anti-CARD-3 or CARD-4 antibodies of the invention can be used to detect and isolate CARD-3 or CARD-4 proteins and modulate CARD-3 or CARD-4 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-3 or CARD-4 proteins or biologically active portions thereof or have a stimulatory or inhibitory effect on, for example, CARD-3 or CARD-4 expression or CARD-3 or CARD-4 activity. An example of a biologically active portion of human CARD-4 is amino acids 1–145 encoding the CARD domain which is sufficient to exhibit CARD-3-binding activity as described in Example 7. Amino acids 406–953 of human CARD4L comprising the LRR domain represent a biologically active portion of CARD-4L because they possess hNUDC-binding activity as described in Example 8.

In one embodiment, the invention provides assays for screening candidate or test compounds which bind to or modulate the activity of a CARD-3 or CARD-4 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

Determining the ability of the test compound to modulate the activity of CARD-3 or CARD-4 or a biologically active portion thereof can be accomplished, for example, by determining the ability of the CARD-3 or CARD-4 protein to bind to or interact with a CARD-3 or CARD-4 target molecule. As used herein, a "target molecule" is a molecule with which a CARD-3 or CARD-4 protein binds or interacts in nature, for example, a molecule associated with the internal surface of a cell membrane or a cytoplasmic molecule. A CARD-3 or A CARD-4 target molecule can be a non-CARD-3 or CARD-4 molecule or a CARD-3 or CARD-4 protein or polypeptide of the present invention. In one embodiment, a CARD-3 or CARD-4 target molecule is a component of a apoptotic signal transduction pathway, e.g., caspases. The target, for example, can be a second intracellular protein which has catalytic activity or a protein which facilitates the association of downstream signaling molecules with CARD-3 or CARD-4. In another embodiment, CARD-3 or CARD-4 target molecules include CARD-4 because CARD-4 was found to bind to both CARD-3 and CARD-4 (Examples 7 and 12), CARD-3 because CARD-3 was found to bind to CARD-4 (Examples 7 and 12), hNUDC because hNUDC was found to bind to CARD-4 (Example 8), and caspase 9 and BCLX which were found to bind to CARD-4 (Example 12). Determining the ability of the test compound to modulate the activity of CARD-3 or CARD-4 or a biologically active portion thereof can be accomplished, for example, by determining the ability of the CARD-3 or CARD-4 protein to bind to or interact with any of the specific proteins listed in the previous paragraph as CARD-3 or CARD-4 target molecules. In another embodiment, CARD-3 or CARD-4 target molecules include all proteins that bind to a CARD-3 or CARD-4 protein or fragment thereof in a two-hybrid system binding assay which can be used without undue experimentation to isolate such proteins from cDNA or genomic two-hybrid system libraries. For example, Example 7 describes the use of the CARD-4 CARD domain region to identify CARD-3 in a two-hybrid screen and Example 8 describes the use of the CARD-4 LRR region to identify hNUDC in a two-hybrid screen. The binding assays described in this section could be cell-based or cell free (described subsequently).

Determining the ability of the CARD-3 or CARD-4 protein to bind to or interact with a CARD-3 or CARD-4 target molecule can be accomplished by one of the methods described above for determining direct binding. In an embodiment, determining the ability of the CARD-3 or CARD-4 protein to bind to or interact with a CARD-3 or CARD-4 target molecule can be accomplished by determining the activity of the target molecule. For example, the activity of the target molecule can be determined by detecting induction of a cellular second messenger of the target (e.g., intracellular Ca2+, diacylglycerol, IP3, etc.), detecting catalytic/enzymatic activity of the target on an appropriate substrate, detecting the induction of a reporter gene (e.g., a CARD-3 or CARD-4-responsive regulatory element operatively linked to a nucleic acid encoding a detectable marker, e.g. luciferase), or detecting a cellular response, for example, cell survival, cellular differentiation, or cell proliferation. For example, in Example 12 CARD-4 is shown to bind to caspase 9 and in Example 10 CARD-4 is shown to enhance caspase 9 activity by monitoring a cellular response, cell death or apoptosis. Because CARD-4 binding to caspase 9 enhances caspase 9 activity, the binding of CARD-4 to caspase 9 can be monitored by assaying the caspase 9-mediated apoptosis cellular response caused by the caspase 9 CARD-4 target molecule or caspase 9 enzymatic activity. In addition, and in another embodiment, genes induced by CARD-3 or CARD-4 expression could be identified by expressing CARD-3 or CARD-4 in a cell line and conducting a transcriptional profiling experiment wherein the mRNA expression patterns of the cell line transformed with an empty expression vector and the cell line transformed with a CARD-3 or CARD-4 expression vector are compared. The promoters of genes induced by CARD-3 or CARD-4 expression could be operatively linked to reporter genes suitable for screening such as luciferase, secreted alkaline phosphatase, or beta-galactosidase and the resulting constructs could be introduced into appropriate expression vectors. A recombinant cell line containing CARD-3 or CARD-4 and transfected with an expression vector containing a CARD-3 or CARD-4 responsive promoter operatively linked to a reporter gene could be used to identify test compounds that modulate CARD-3 or CARD-4 activity by assaying the expression of the reporter gene in response to contacting the recombinant cell line with test compounds. CARD-3 or CARD-4 agonists can be identified as increasing the expression of the reporter gene and CARD-3 or CARD-4 antagonists can be identified as decreasing the expression of the reporter gene.

In another embodiment of the invention, the ability of a test compound to modulate the activity of CARD-3, CARD-4, or biologically active portions thereof can be determined by assaying the ability of the test compound to modulate CARD-3 or CARD-4-dependent pathways or processes where the CARD-3 or CARD-4 target proteins that mediate the CARD-3 or CARD-4 effect are known or unknown. Potential CARD-3 or CARD-4-dependent pathways or processes include but are not limited to the modulation of cellular signal transduction pathways and their related second messenger molecules (e.g., intracellular Ca2+, diacylglycerol, IP3, cAMP etc.), cellular enzymatic activities, cellular responses(e.g., cell survival, cellular differentiation, or cell proliferation), or the induction or repression of cellular or heterologous mRNAs or proteins. CARD-3 or CARD-4-dependent pathways or processes could be assayed by standard cell-based or cell free assays appropriate for the specific pathway or process under study. For example, Example 9 describes how expression of CARD-4S or CARD-4L in 293T cells induces the NF-KB pathway as determined by the measurement of a cotransfected NF-KB pathway luciferase reporter gene. In another embodiment, cells cotransfected with CARD-4 and the NF-KB luciferase reporter gene could be contacted with a test compound and test compounds that block CARD-4 activity could be identified by their reduction of CARD-4-dependent NF-KB pathway luciferase reporter gene expression. Test compounds that agonize CARD-4 would be expected to increase reporter gene expression. In another embodiment, CARD-4 could be expressed in a cell line and the recombinant CARD-4-expressing cell line could be contacted with a test compound. Test compounds that inhibit CARD-4 activity could be identified by their reduction of CARD-4-depended NF-κB pathway stimulation as measured by the assay of a NF-κB pathway reporter gene, NF-κB nuclear localization, IkB phosphorylation or proteolysis, or other standard assays for NF-κB pathway activation known to those skilled in the art.

In yet another embodiment, an assay of the present invention is a cell-free assay comprising contacting a CARD-3 or CARD-4 protein or biologically active portion thereof with a test compound and determining the ability of the test compound to bind to the CARD-3 or CARD-4 protein or biologically active portion thereof. Binding-of the test compound to the CARD-3 or CARD-4 protein can be determined either directly or indirectly as described above. In one embodiment, a competitive binding assay includes contacting the CARD-3 or CARD-4 protein or biologically active portion thereof with a compound known to bind CARD-3 or CARD-4 to form an assay mixture, contacting the assay mixture with a test compound, and determining the ability of the test compound to interact with a CARD-3 or CARD-4 protein, wherein determining the ability of the test compound to interact with a CARD-3 or CARD-4 protein comprises determining the ability of the test compound to preferentially bind to CARD-3 or CARD-4 or biologically active portion thereof as compared to the known binding compound.

In another embodiment, an assay is a cell-free assay comprising contacting CARD-3 or CARD-4 protein or biologically active portion thereof with a test compound and determining the ability of the test compound to modulate (e.g., stimulate or inhibit) the activity of the CARD-3 or CARD-4 protein or biologically active portion thereof. Determining the ability of the test compound to modulate the activity of CARD-3 or CARD-4 can be accomplished, for example, by determining the ability-of the CARD-3 or CARD-4 protein to bind to a CARD-3 or CARD-4 target molecule by one of the methods described above for determining direct binding. In an alternative embodiment, determining the ability of the test compound to modulate the activity of CARD-3 or CARD-4 can be accomplished by determining the ability of the CARD-3 or CARD-4 protein to further modulate a CARD-3 or CARD-4 target molecule. For example, the catalytic/enzymatic activity of the target molecule on an appropriate substrate can be determined as previously described.

In yet another embodiment, the cell-free assay comprises contacting the CARD-3 or CARD-4 protein or biologically active portion thereof with a known compound which binds CARD-3 or CARD-4 to form an assay mixture, contacting the assay mixture with a test compound, and determining the ability of the test compound to interact with a CARD-3 or CARD-4 protein, wherein determining the ability of the test compound to interact with a CARD-3 or CARD-4 protein comprises determining the ability of the CARD-3 or CARD-4 protein to preferentially bind to or modulate the activity of a CARD-3 or CARD-4 target molecule. The cell-free assays of the present invention are amenable to use of both the soluble form or the membrane-associated form of CARD-3 or CARD-4. A membrane-associated form of CARD-3 or CARD-4 refers to CARD-3 or CARD-4 that interacts with a membrane-bound target molecule. In the case of cell-free assays comprising the membrane-associated form of CARD-3 or CARD-4, it may be desirable to utilize a solubilizing agent such that the membrane-associated form of CARD-3 or CARD-4 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CARD-3 or CARD-4 or its target molecule to facilitate separation of complexed from uncomplexed forms of one or both of the proteins, as well as to accommodate automation of the assay. Binding of a test compound to CARD-3 or CARD-4, or interaction of CARD-3 or CARD-4 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/CARD-3 or CARD-4 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-3 or CARD-4 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-3 or CARD-4 binding or activity determined using standard techniques. In an alternative embodiment, MYC or HA epitope tag CARD-3 or CARD-4 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or CARD-3 or CARD-4 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-3 or CARD-4 binding or activity determined using standard techniques. Example 12 describes an HA epitope tagged CARD-4 protein that physically interacts in a coimmunoprecipitation assay with MYC epitope tagged CARD-4, MYC epitope tagged CARD-3, MYC epitope tagged caspase 9, and MYC epitope tagged BCLX. In an embodiment of the invention, HA epitope tagged CARD-4 could be used in combination with any of the four MYC epitope tagged CARD-4 target proteins in the sort of protein-protein interaction assay described earlier in this paragraph.

Other techniques for immobilizing proteins on matrices can also be used in the screening assays of the invention. For example, either CARD-3 or CARD-4 or its target molecule can be immobilized utilizing conjugation of biotin and streptavidin. Biotinylated CARD-3 or CARD-4 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-3 or CARD-4 or target molecules but which do not interfere with binding of the CARD-3 or CARD-4 protein to its target molecule can be derivatized to the wells of the plate, and unbound target or CARD-3 or CARD-4 trapped in the wells by antibody conjugation. Methods for detecting such complexes, in addition to those described above for the GST-immobilized complexes and epitope tag immobilized complexes, include immunodetection of complexes using antibodies reactive with the CARD-3 or CARD-4 or target molecule, as well as enzyme-linked assays which rely on detecting an enzymatic activity associated with the CARD-3 or CARD-4 or target molecule.

In another embodiment, modulators of CARD-3 or CARD-4 expression are identified in a method in which a cell is contacted with a candidate compound and the expression of the CARD-3 or CARD-4 promoter, mRNA or protein in the cell is determined. The level of expression of CARD-3 or CARD-4 mRNA or protein in the presence of the candidate compound is compared to the level of expression of CARD-3 or CARD-4 mRNA or protein in the absence of the candidate compound. The candidate compound can then be identified as a modulator of CARD-3 or CARD-4 expression based on this comparison. For example, when expression of CARD-3 or CARD-4 mRNA or protein is greater (statistically significantly greater) in the presence of the candidate compound than in its absence, the candidate compound is identified as a stimulator of CARD-3 or CARD-4 mRNA or protein expression. Alternatively, when expression of CARD-3 or CARD-4 mRNA or protein is less (statistically significantly less) in the presence of the candidate compound than in its absence, the candidate compound is identified as an inhibitor of CARD-3 or CARD-4 mRNA or protein expression. The level of CARD-3 or CARD-4 mRNA or protein expression in the cells can be determined by methods described herein for detecting CARD-3 or CARD-4 mRNA or protein. The activity of the CARD-3 or CARD-4 promoter can be assayed by linking the CARD-3 or CARD-4 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds. For example, two CARD-4-specific mRNAs were detected in a Northern blotting experiment, one of 4.6 kilobases and the other of 6.5–7.0 kilobases (Example 11). In Example 11, CARD-4-specific mRNA species were found to be widely distributed in the tissues and cell lines studied.

In yet another aspect of the invention, the CARD-3 or CARD-4 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with CARD-3 or CARD-4 ("CARD-3 or CARD-4-binding proteins" or "CARD-3 or CARD-4-bp") and modulate CARD-3 or CARD-4 activity. Such CARD-3 or CARD-4-binding proteins are also likely to be involved in the propagation of signals by the CARD-3 or CARD-4 proteins as, for example, upstream or downstream elements of the CARD-3 or CARD-4 pathway. For example, Example 7 describes the construction of a two-hybrid screening bait construct including human CARD-4L amino acids 1–145 comprising the CARD domain and the use of this bait construct to screen human mammary gland and prostate gland two-hybrid libraries resulting in the identification of human CARD-3 as a CARD-4 interacting protein. In another example, Example 8 describes the construction of a two-hybrid screening bait construct including human CARD-4 amino acids 406–953 comprising the LRR domain and the use of-this bait construct to screen a human mammary gland two-hybrid libraries resulting in the identification of hNUDC as a CARD-4 interacting protein.

The two-hybrid system is based on the modular nature of most transcription factors, which consist of separable DNA-binding and activation domains. Briefly, the assay utilizes two different DNA constructs. In one construct, the gene that codes for CARD-3 or CARD-4 is fused to a gene encoding the DNA binding domain of a known transcription factor (e.g., GAL-4). In the other construct, a DNA sequence, from a library of DNA sequences, that encodes an a unidentified protein ("prey" or "sample") is fused to a gene that codes for the activation domain of the known transcription factor. If the "bait" and the "prey" proteins are able to interact, in vivo, forming an CARD-3 or CARD-4-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-3 or CARD-4.

In an embodiment of the invention, the ability of a test compound to modulate the activity of CARD-3, CARD-4, or a biologically active portion thereof can be determined by assaying the ability of the test compound to block the binding of CARD-3 and CARD-4 to their target proteins in a two-hybrid system assay. Example 7 describes a two-hybrid system assay for the interaction between CARD-3 and CARD-4 and Example 8 describes a two-hybrid system assay for the interaction between CARD-4 and its target protein hNUDC. To screen for test compounds that block the interaction between CARD-3 and CARD-4 and their target proteins, which include but are not limited to CARD-3, CARD-4, and hNUDC, a yeast two-hybrid screening strain coexpressing the interacting bait and prey constructs, for example, a CARD-4 bait construct and a CARD-3 prey construct as described in Example 7, is contacted with the test compound and the activity of the two-hybrid system reporter gene, usually HIS3, lacZ, or URA3 is assayed. If the strain remains viable but exhibits a significant decrease in reporter gene activity, this would indicate that the test compound has inhibited the interaction between the bait and prey proteins. This assay could be automated for high throughput drug screening purposes. In another embodiment of the invention, CARD-3 or CARD-4 and their target proteins could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a CARD-3 or CARD-4 physical interaction with a target protein would result in induction of a reporter gene in contrast to the normal two-hybrid system where inhibition of CARD-3 or CARD-4 physical interaction with a target protein would lead to reporter gene repression. The reverse two-hybrid system is preferred for drug screening because reporter gene induction is more easily assayed than reporter gene repression.

Alternative embodiments of the invention are proteins found to physically interact with proteins that bind to CARD-3 or CARD-4. CARD-3 or CARD-4 interactors, including but not limited to hNUDC, caspase 9, BCLX, and CARD-3, could be configured into two-hybrid system baits and used in two-hybrid screens to identify additional members of the CARD-3 and CARD-4 pathway. The interactors of CARD-3 or CARD-4 interactors identified in this way could be useful targets for therapeutic intervention in CARD-4 related diseases and pathologies and an assay of their enzymatic or binding activity could be useful for the identification of test compounds that modulate CARD-3 or CARD-4 activity.

This invention further-pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-3 or CARD-4 nucleic acid molecules described herein or fragments thereof, can be used to map the location of CARD-3 or CARD-4 genes on a chromosome. The mapping of the CARD-3 or CARD-4 sequences to chromosomes is an important first step in correlating these sequences with genes associated with disease.

Briefly, CARD-3 or CARD-4 genes can be mapped to chromosomes by preparing PCR primers (preferably 15–25 bp in length) from the CARD-3 or CARD-4 sequences. Computer analysis of CARD-3 or CARD-4 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-3 or CARD-4 sequences will yield an amplified fragment. For example, in Example 6, human CARD-4-specific PCR primers were used to screen DNAs from a somatic cell hybrid panel showing that human CARD-4 maps to chromosome 7 close to the SHGC-31928 genetic marker.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-3 or CARD-4 sequences to design oligonucleotide primers, sublocalization can be achieved with panels of fragments from specific chromosomes. Other mapping strategies which can similarly be used to map a CARD-3 or CARD-4 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the CARD-3 or CARD-4 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CARD-3 or CARD-4 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-3 or CARD-4 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-3 or CARD-4 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:7, SEQ ID NO:25 and SEQ ID NO:43 can comfortably provide positive individual identification with a panel of perhaps 10 to 1,000 primers which each yield a noncoding amplified sequence of 100 bases. If predicted coding sequences, such as those in SEQ ID NO:3, SEQ ID NO:9, and SEQ ID NO:27 are used, a more appropriate number of primers for positive individual identification would be 500–2,000.

If a panel of reagents from CARD-3 or CARD-4 sequences described herein is used to generate a unique identification database for an individual, those same reagents can later be used to identify tissue from that individual. Using the unique identification database, positive identification of the individual, living or dead, can be made from extremely small tissue samples.

3. Use of Partial CARD-3 or CARD-4 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:7, and SEQ ID NO:25 are particularly appropriate for this use as greater numbers of polymorphisms occur in the noncoding regions, making it easier to differentiate individuals using this technique. Examples of polynucleotide reagents include the CARD-3 or CARD-4 sequences or portions thereof, e.g., fragments derived from the noncoding regions of SEQ ID NO:1, SEQ ID NO:7, or SEQ ID NO:25 which have a length of at least 20 or 30 bases.

The CARD-3 or CARD-4 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-3 or CARD-4 probes can be used to identify tissue by species and/or by organ type.

In a similar fashion, these reagents, e.g., CARD-3 or CARD-4 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-3 or CARD-4 protein and/or nucleic acid expression as well as CARD-3 or CARD-4 activity, in the context of a biological sample (e.g., blood, serum, cells, tissue) to thereby determine whether an individual is afflicted with a disease or disorder, or is at risk of developing a disorder, associated with aberrant CARD-3 or CARD-4 expression or activity. The invention also provides for prognostic (or predictive) assays for determining whether an individual is at risk of developing a disorder associated with CARD-3 or CARD-4 protein, nucleic acid expression or activity. For example, mutations in a CARD-3 or CARD-4 gene can be assayed in a biological sample. Such assays can be used for prognostic or predictive purpose to thereby prophylactically treat an individual prior to the onset of a disorder characterized by or associated with CARD-3 or CARD-4 protein, nucleic acid expression or activity.

Another aspect of the invention provides methods for determining CARD-3 or CARD-4 protein, nucleic acid expression or CARD-3 or CARD-4 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-3 or CARD-4 in clinical trials.

These and other agents are described in further detail in the following sections.

1. Diagnostic Assays

An exemplary method for detecting the presence or absence of CARD-3 or CARD-4 in a biological sample involves obtaining a biological sample from a test subject and contacting the biological sample with a compound or an agent capable of detecting CARD-3 or CARD-4 protein or nucleic acid (e.g., mRNA, genomic DNA) that encodes CARD-3 or CARD-4 protein such that the presence of CARD-3 or CARD-4 is detected in the biological sample. An agent for detecting CARD-3 or CARD-4 mRNA or genomic DNA is a labeled nucleic acid probe capable of hybridizing to CARD-3 or CARD-4 mRNA or genomic DNA. The nucleic acid probe can be, for example, a full-length CARD-3 or CARD-4 nucleic acid, such as the nucleic acid of SEQ ID NO:1 or 3, SEQ ID NO:7 or 9, SEQ ID NO:25 or 27, or a portion thereof, such as an oligonucleotide of at least 15, 30, 50, 100, 250 or 500 nucleotides in length and sufficient to specifically hybridize under stringent conditions to CARD-3 or CARD-4 mRNA or genomic DNA, or a human CARD-4 splice variant such as the nucleic acid of SEQ ID NO:39 or SEQ ID NO:41. Other suitable probes for use in the diagnostic assays of the invention are described herein. For example, Example 11 describes the use of a nucleic acid probe to detect CARD-4 mRNAs in human tissues and cell lines and the probe used in this experiment could be used for a diagnostic assay.

An agent for detecting CARD-3 or CARD-4 protein can be an antibody capable of binding to CARD-3 or CARD-4 protein, preferably an antibody with a detectable label. Antibodies can be polyclonal, or more preferably, monoclonal. For example, polypeptides corresponding to amino acids 128–139 and 287–298 of human CARD-4L were used to immunize rabbits and produce polyclonal antibodies that specifically recognize human CARD-4L. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-3 or CARD-4 mRNA, protein, or genomic DNA in a biological sample in vitro as well as in vivo. For example, in vitro techniques for detection of CARD-3 or CARD-4 mRNA include Northern hybridizations and in situ hybridizations. For example, Example 11 contains the use of a human CARD-4L nucleic acid probe for a Northern blotting analysis of mRNA species encoded by human CARD-4L detected in RNA samples from human tissues and cell lines. In vitro techniques for detection of CARD-3 or CARD-4 protein include enzyme linked immunosorbent assays (ELISAs), Western blots, immunoprecipitations and immunofluorescence. In vitro techniques for detection of CARD-3 or CARD-4 genomic DNA include Southern hybridizations. Furthermore, in vivo techniques for detection of. CARD-3 or CARD-4 protein include introducing into a subject a labeled anti-CARD-3 or CARD-4 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. An biological sample is a peripheral blood leukocyte sample isolated by conventional means from a subject.

In another embodiment, the methods further involve obtaining a control biological sample from a control subject, contacting the control sample with a compound or agent capable of detecting CARD-3 or CARD-4 protein, mRNA, or genomic DNA, such that the presence of CARD-3 or CARD-4 protein, mRNA or genomic DNA is detected in the biological sample, and comparing the presence of CARD-3 or CARD-4 protein, mRNA or genomic DNA in the control sample with the presence of CARD-3 or CARD-4 protein, mRNA or genomic DNA in the test sample.

The invention also encompasses kits for detecting the presence of CARD-3 or CARD-4 in a biological sample (a test sample). Such kits can be used to determine if a subject is suffering from or is at increased risk of developing a disorder associated with aberrant expression of CARD-3 or CARD-4 (e.g., an immunological disorder). For example, the kit can comprise a labeled compound or agent capable of detecting CARD-3 or CARD-4 protein or mRNA in a biological sample and means for determining the amount of CARD-3 or CARD-4 in the sample (e.g., an anti-CARD-3 or CARD-4 antibody or an oligonucleotide probe which binds to DNA encoding CARD-3 or CARD-4, e.g., SEQ ID NO:1, SEQ ID NO:3, SEQ ID NO:7, SEQ ID NO:9, SEQ ID NO:25 or SEQ ID NO:27). Kits may also include instruction for observing that the tested subject is suffering from or is at risk of developing a disorder associated with aberrant expression of CARD-3 or CARD-4 if the amount of CARD-3 or CARD-4 protein or mRNA is above or below a normal level.

For antibody-based kits, the kit may comprise, for example: (1) a first antibody (e.g., attached to a solid support) which binds to CARD-3 or CARD-4 protein; and, optionally, (2) a second, different antibody which binds to CARD-3 or CARD-4 protein or the first antibody and is conjugated to a detectable agent.

For oligonucleotide-based kits, the kit may comprise, for example: (1) a oligonucleotide, e.g., a detectably labelled oligonucleotide, which hybridizes to a CARD-3 or CARD-4 nucleic acid sequence or (2) a pair of primers useful for amplifying a CARD-3 or CARD-4 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of CARD-3 or CARD-4.

2. Prognostic Assays

The methods described herein can furthermore be utilized as diagnostic or prognostic assays to identify subjects having or at risk of developing a disease or disorder associated with aberrant CARD-3 or CARD-4 expression or activity. For example, the assays described herein, such as the preceding diagnostic assays or the following assays, can be utilized to identify a subject having or at risk of developing a disorder associated with CARD-3 or CARD-4 protein, nucleic acid expression or activity. Alternatively, the prognostic assays can be utilized to identify a subject having or at risk for developing such a disease or disorder. Thus, the present invention provides a method in which a test sample is obtained from a subject and CARD-3 or CARD-4 protein or nucleic acid (e.g., mRNA, genomic DNA) is detected, wherein the presence of CARD-3 or CARD-4 protein or nucleic acid is diagnostic for a subject having or at risk of developing a disease or disorder associated with aberrant CARD-3 or CARD-4 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-3 or CARD-4 expression or activity. For example, such methods can be used to determine whether a subject can be effectively treated with a specific agent or class of agents (e.g., agents of a type which decrease CARD-3 or CARD-4 activity). Thus, the present invention provides methods for determining whether a subject can be effectively treated with an agent for a disorder associated with aberrant CARD-3 or CARD-4 expression or activity in which a test sample is obtained and CARD-3 or CARD-4 protein or nucleic acid is detected (e.g., wherein the presence of CARD-3 or CARD-4 protein or nucleic acid is diagnostic for a subject that can be administered the agent to treat a disorder associated with aberrant CARD-3 or CARD-4 expression or activity).

The methods of the invention can also be used to detect genetic lesions or mutations in a CARD-3 or CARD-4 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a CARD-3 or CARD-4-protein, or the mis-expression of the CARD-3 or CARD-4 gene. For example, such genetic lesions can be detected by ascertaining the existence of at least one of 1) a deletion of one or more nucleotides from a CARD-3 or CARD-4 gene; 2) an addition of one or more nucleotides to a CARD-3 or CARD-4 gene; 3) a substitution of one or more nucleotides of a CARD-3 or CARD-4 gene, 4) a chromosomal rearrangement of a CARD-3 or CARD-4 gene; 5) an alteration in the level of a messenger RNA transcript of a CARD-3 or CARD-4 gene, 6) aberrant modification of a CARD-3 or CARD-4 gene, such as of the methylation pattern of the genomic DNA, 7) the presence of a non-wild type splicing pattern of a messenger RNA transcript of a CARD-3 or CARD-4 gene, 8) a non-wild type level of a CARD-3 or CARD-4-protein, 9) allelic loss of a CARD-3 or CARD-4 gene, and 10) inappropriate post-translational modification of a CARD-3 or CARD-4-protein. As described herein, there are a large number of assay techniques known in the art which can be used for detecting lesions in a CARD-3 or CARD-4 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the CARD-3 or CARD-4-gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-3 or CARD-4 gene under conditions such that hybridization and amplification of the CARD-3 or CARD-4-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-3 or CARD-4 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in CARD-3 or CARD-4 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in CARD-3 or CARD-4 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-3 or CARD-4 gene and detect mutations by comparing the sequence of the sample CARD-3 or CARD-4 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the CARD-3 or CARD-4 gene include methods in which protection from cleavage agents is used to detect mismatched bases in RNA/RNA or RNA/DNA heteroduplexes (Myers et al.

(1985) Science 230:1242). In general, the art technique of "mismatch cleavage" starts by providing heteroduplexes of formed by hybridizing (labeled) RNA or DNA containing the wild-type CARD-3 or CARD-4 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-3 or CARD-4 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a CARD-3 or CARD-4 sequence, e.g., a wild-type CARD-3 or CARD-4 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in CARD-3 or CARD-4 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control CARD-3 or CARD-4 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather-than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-3 or CARD-4 gene.

Furthermore, any cell type or tissue, preferably peripheral blood leukocytes, in which CARD-3 or CARD-4 is expressed may be utilized in the prognostic assays described herein.

3. Pharmacogenomics

Agents, or modulators which have a stimulatory or inhibitory effect on CARD-3 or CARD-4 activity (e.g., CARD-3 or CARD-4 gene expression) as identified by a screening assay described herein can be administered to individuals to treat (prophylactically or therapeutically) disorders (e.g., an immunological disorder) associated with aberrant CARD-3 or CARD-4 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-3 or CARD-4 protein, expression of CARD-3 or CARD-4 nucleic acid, or mutation content of CARD-3 or CARD-4 genes in an individual can be determined to thereby select appropriate agent(s) for therapeutic or prophylactic treatment of the individual.

harmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of CARD-3 or CARD-4 protein, expression of CARD-3 or CARD-4 nucleic acid, or mutation content of CARD-3 or CARD-4 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-3 or CARD-4 modulator, such as a modulator identified by one of the exemplary screening assays described herein.

4. Monitoring of Effects During Clinical Trials

Monitoring the influence of agents (e.g., drugs, compounds) on the expression or activity of CARD-3 or CARD-4 (e.g., the ability to modulate aberrant cell proliferation and/or differentiation) can be applied not only in basic drug screening, but also in clinical trials. For example, the effectiveness of an agent determined by a screening assay as described herein to increase CARD-3 or CARD-4 gene expression, protein levels, or upregulate CARD-3 or CARD-4 activity, can be monitored in clinical trails of subjects exhibiting decreased CARD-3 or CARD-4 gene expression, protein levels, or downregulated CARD-3 or CARD-4 activity. Alternatively, the effectiveness of an agent determined by a screening assay to decrease CARD-3 or CARD-4 gene expression, protein levels, or downregulated CARD-3 or CARD-4 activity, can be monitored in clinical trials of subjects exhibiting increased CARD-3 or CARD-4 gene expression, protein levels, or upregulated CARD-3 or CARD-4 activity. In such clinical trials, the expression or activity of CARD-3 or CARD-4 and, preferably, other genes that have been implicated in, for example, a cellular proliferation disorder can be used as a "read out" or markers of the immune responsiveness of a particular cell.

For example, and not by way of limitation, genes, including CARD-3 or CARD-4, that are modulated in cells by treatment with an agent (e.g., compound, drug or small molecule) which modulates CARD-3 or CARD-4 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-3 or CARD-4 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-3 or CARD-4 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-3 or CARD-4 protein, mRNA, or genomic DNA in the preadministration sample; (iii) obtaining one or more post-administration samples from the subject; (iv) detecting the level of expression or activity of the CARD-3 or CARD-4 protein, mRNA, or genomic DNA in the post-administration samples; (v) comparing the level of expression or activity of the CARD-3 or CARD-4 protein, mRNA, or genomic DNA in the pre-administration sample with the CARD-3 or CARD-4 protein, mRNA, or genomic DNA in the post administration sample or samples; and (vi) altering the administration of the agent to the subject accordingly. For example, increased administration of the agent may be desirable to increase the expression or activity of CARD-3 or CARD-4 to higher levels than detected, i.e., to increase the effectiveness of the agent. Alternatively, decreased administration of the agent may be desirable to decrease expression or activity of CARD-3 or CARD-4 to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant CARD-3 or CARD-4 expression or activity.

1. Prophylactic Methods

In one aspect, the invention provides a method for preventing in a subject, a disease or condition associated with an aberrant CARD-3 or CARD-4 expression or activity, by administering to the subject an agent which modulates CARD-3 or CARD-4 expression or at least one CARD-3 or CARD-4 activity. Subjects at risk for a disease which is caused or contributed to by aberrant CARD-3 or CARD-4 expression or activity can be identified by, for example, any or a combination of diagnostic or prognostic assays as described herein. Administration of a prophylactic agent can occur prior to the manifestation of symptoms characteristic of the CARD-3 or CARD-4 aberrancy, such that a disease or disorder is prevented or, alternatively, delayed in its progression. Depending on the type of CARD-3 or CARD-4 aberrancy, for example, a CARD-3 or CARD-4 agonist or CARD-3 or CARD-4 antagonist agent can be used for treating the subject. The appropriate agent can be determined based on screening assays described herein. Activities of CARD-3 or CARD-4 that could be modulated for prophylactic purposes include, but are not limited to, 1) CARD-3 or CARD-4 gene or protein expression, for example, see Example 11 for a description of the mRNA expression pattern of human CARD-4; 2) CARD-3 or CARD-4 binding to a target protein, for example, see Examples 7, 8, and 12 for a description of proteins known to bind to CARD-3 or CARD-4; 3) CARD-4 regulation of NF-κB as described in Example 9; and 4) CARD-4 enhancement of caspase 9 activity as described in Example 10.

2. Therapeutic Methods

Another aspect of the invention pertains to methods of modulating CARD-3 or CARD-4 expression or activity for therapeutic purposes. The modulatory method of the invention involves contacting a cell with an agent that modulates one or more of the activities of CARD-3 or CARD-4 protein activity associated with the cell. An agent that modulates CARD-3 or CARD-4 protein activity can be an agent as described herein, such as a nucleic acid or a protein, a naturally-occurring cognate ligand of a CARD-3 or CARD-4 protein, a peptide, a CARD-3 or CARD-4 peptidomimetic, or other small molecule. In one embodiment, the agent stimulates one or more of the biological activities of CARD-3 or CARD-4 protein. Examples of such stimulatory agents include active CARD-3 or CARD-4 protein and a nucleic acid molecule encoding CARD-3 or CARD-4 that has been introduced into the cell. In another embodiment, the agent inhibits one or more of the biological activities of CARD-3 or CARD-4 protein. Examples of such inhibitory agents include antisense CARD-3 or CARD-4 nucleic acid molecules and anti-CARD-3 or CARD-4 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a CARD-3 or CARD-4 protein or nucleic acid molecule. In one embodiment, the method involves administering an agent (e.g., an agent identified by a screening assay described herein), or combination of agents that modulates (e.g., upregulates or downregulates) CARD-3 or CARD-4 expression or activity. In another embodiment, the method involves administering a CARD-3 or CARD-4 protein or nucleic acid molecule as therapy to compensate for reduced or aberrant CARD-3 or CARD-4 expression or activity.

Activities of CARD-3 or CARD-4 that could be modulated for therapeutic purposes include, but are not limited to, 1) CARD-3 or CARD-4 gene or protein expression, for example, see Example 11 for a description of the mRNA expression pattern of human CARD-4; 2) CARD-3 or CARD-4 binding to a target protein, for example, see Examples 7, 8, and 12 for a description of proteins known to bind to CARD-3 or CARD-4; 3) CARD-4 regulation of NF-κB as described in Example 9; and 4) CARD-4 enhancement of caspase 9 activity as described in Example 10.

Stimulation of CARD-3 or CARD-4 activity is desirable in situations in which CARD-3 or CARD-4 is abnormally downregulated and/or in which increased CARD-3 or CARD-4 activity is likely to have a beneficial effect. Conversely, inhibition of CARD-3 or CARD-4 activity is desirable in situations in which CARD-3 or CARD-4 is abnormally upregulated, e.g., in myocardial infarction, and/or in which decreased CARD-3 or CARD-4 activity is likely to have a beneficial effect. Since CARD-4 may play be involved in the processing of cytokines, inhibiting the activity or expression CARD4- may be beneficial in patients that have aberrant inflammation.

This invention is further illustrated by the following examples which should not be construed as limiting. The contents of all references, patents and published patent applications cited throughout this application are hereby incorporated by reference.

EXAMPLES

Example 1

Isolation and Characterization of Full-length Human CARD-3 and CARD-4L/S cDNAs

A profile of known CARD domains was used to search databases of cDNA sequences and partial cDNA sequences using TBLASTN (Washington University; version 2.0, BLOSUM62 search matrix). This search led to the identification of CARD-3.

Using CARD-3 to search databases of cDNA sequences and partial cDNA sequences, another potential CARD cDNA was found. This cDNA sequence was used screen a human umbilical vein endothelial library (HUVE) and a clone containing the partial CARD-4S was identified. The human umbilical vein endothelial library was then rescreened using a probe designed against the partial CARD-4S sequence and a clone containing the CARD-4L sequence was identified.

Example 2

Characterization of CARD-3 AND CARD-4L/S Proteins

In this example, the predicted amino acid sequences of human CARD-3 and CARD-4L/S proteins were compared to amino acid sequences of known proteins and various motifs were identified. For example, the CARD domains of CARD-3 and CARD-4 were aligned (FIG. 7) with the CARD domains of ARC-CARD (SEQ ID NO:31), cIAP1-CARD (SEQ ID NO:32), cIAP1-CARD (SEQ ID NO:33) and cIAP2-CARD (SEQ ID NO:34). In addition, the molecular weight of the human CARD-3 and CARD-4L/S proteins were predicted.

The human CARD-3 cDNA was isolated as described above (FIG. 1; SEQ ID NO:1) and encodes a 540 amino acid protein (FIG. 2: SEQ ID NO:2). CARD-3 also includes one Predicted kinase domain (amino acid 1 to amino acid 300 of SEQ ID NO:2; SEQ ID NO:4), which is followed by a predicted linker domain (amino acid 301 to amino acid 431 of SEQ ID NO:2; SEQ ID NO:5) and a predicted CARD domain (amino acid 432 to amino acid 540 of SEQ ID NO:2; SEQ ID NO:6).

The human CARD-4L cDNA was isolated as described above (FIGS. 3A–3B; SEQ ID NO:7) and has a 2859 nucleotide open reading frame (nucleotides 245–3103 of SEQ ID NO:7; SEQ ID NO:9) which encodes a 953 amino acid protein (FIG. 4; SEQ ID NO:8). CARD-4L protein has a predicted CARD domain (amino acids 15–114; SEQ ID NO:10). CARD-4L is also predicted to have a nucleotide binding domain which extends from about amino acid 198 to about amino acid 397 of SEQ ID NO:8; SEQ ID NO:11, a predicted Walker Box "A", which extends from about amino acid 202 to about amino acid 209 of SEQ ID NO:8; SEQ ID NO:12, a predicted Walker Box "B", which extends from about amino acid 280 to about amino acid 284, of SEQ ID NO:8; SEQ ID NO:13, a predicted kinase 3a subdomain, which extends from about amino acid 327 to about amino acid 338 of SEQ ID NO:8; SEQ ID NO:14, and ten predicted Leucine-rich repeats which extend from about amino acid 674 to about amino acid 950 of SEQ ID NO:8. The first Leucine-rich repeat is predicted to extend from about amino acid 674 to about amino acid 701 of SEQ ID NO:8; SEQ ID NO:15. The second Leucine-rich repeat is predicted to extend from about amino acid 702 to about amino acid 727 of SEQ ID NO:8; SEQ ID NO:16. The third Leucine-rich repeat is predicted to extend from about amino acid 728 to about amino acid 754 of SEQ ID NO:8; SEQ ID NO:17. The fourth Leucine-rich repeat is predicted to extend from about amino acid 755 to about amino acid 782 of SEQ ID NO:8; SEQ ID NO:18. The fifth Leucine-rich repeat is predicted to extend from about amino acid 783 to about amino acid 810 of SEQ ID NO:8; SEQ ID NO:19. The sixth Leucine-rich repeat is predicted to extend from about amino acid 811 to about amino acid 838 of SEQ ID NO:8; SEQ ID NO:20. The seventh Leucine-rich repeat is predicted to extend from about amino acid 839 to about amino acid 866 of SEQ ID NO:8; SEQ ID NO:21. The eighth Leucine-rich repeat is predicted to extend from about amino acid 867 to about amino acid 894 of SEQ ID NO:8; SEQ ID NO:22. The ninth Leucine-rich repeat is predicted to extend from about amino acid 895 to about amino acid 922 of SEQ ID NO:8; SEQ ID NO:23 and the tenth leucine-rich repeat is predicted to extend from about amino acid 923 to about amino acid 950 of SEQ ID NO:8; SEQ ID NO:24.

The human partial CARD-4S cDNA isolated as described above (FIG. 5; SEQ ID NO:25) encodes a 490 amino acid protein (FIG. 6; SEQ ID NO:26). CARD-4S includes one predicted partial CARD domain (amino acids 1–74 of SEQ ID NO:26). CARD-4S is also predicted to have a P-Loop which extends from about amino acid 163 to about amino acid 170 of SEQ ID NO:26; SEQ ID NO:29, and a predicted Walker Box "B" which extends form about amino acid 241 to about amino acid 245 of SEQ ID NO:26; SEQ ID NO:30.

A plot showing the predicted structural features of CARD-4L is presented in FIG. 8. This figure shows the predicted alpha regions (Garnier-Robinson and Chou-Fasman), the predicted beta regions (Garnier-Robinson and Chou-Fasman), the predicted turn regions (Garnier-Robinson and Chou-Fasman) and the predicted coil regions (Garnier-Robinson and Chou-Fasman). Also included in the figure is a hydrophilicity plot (Kyte-Doolittle), the predicted alpha and beta-amphatic regions (Eisenberg), the predicted flexible regions (Karplus-Schulz), the predicted antigenic index (Jameson-Wolf) and the predicted surface probability plot (Emini).

A plot showing the predicted structural features of CARD-4S is also presented in FIG. 9. This figure shows the predicted alpha regions (Garnier-Robinson and Chou-Fasman), the predicted beta regions (Garnier-Robinson and Chou-Fasman), the predicted turn regions (Garnier-Robinson and Chou-Fasman) and the predicted coil regions (Garnier-Robinson and Chou-Fasman). Also included in the figure is a hydrophilicity plot (Kyte-Doolittle), the predicted alpha and beta-amphatic regions (Eisenberg), the predicted flexible regions (Karplus-Schulz), the predicted antigenic index (Jameson-Wolf) and the predicted surface probability plot (Emini).

The predicted MW of CARD-3 is approximately 61 kDa. The predicted MW of CARD-4L is approximately 108 kDa.

Example 3

Preparation of CARD-3 and CARD-4 Proteins

Recombinant CARD-3 and CARD-4 can be produced in a variety of expression systems. For example, the CARD-3 and CARD-4 peptides can be expressed as a recombinant glutathione-S-transferase (GST) fusion protein in *E. coli* and the fusion protein can be isolated and characterized. Specifically, as described above, CARD-3 or CARD-4 can be fused to-GST and the fusion protein can be expressed in *E. coli* strain PEB199. Expression of the GST-CARD-3 or GST-CARD-4 fusion protein in PEB199 can be induced with IPTG. The recombinant fusion protein can be purified from crude bacterial lysates of the induced PEB199 strain by affinity chromatography on glutathione beads.

Example 4

Identification of Splice Variants of CARD4

The 5' untranslated sequence from CARD-4L was used to search databases of cDNA sequences and partial cDNA sequences using BLASTN (Washington University; version 2.0, BLOSUM62 search matrix) for additional CARD-4 cDNA clones. This search led to the identification of two cDNA clones, clone Z from a human lymph node library and the Y clone from a human brain cDNA library. Both clones were sequenced and found to represent probable splice variants of CARD-4 that encode truncated CARD-4 proteins, Y encoding a 249 amino acid protein and Z encoding a 164 amino acid protein. FIG. 10 shows the nucleotide (SEQ ID NO:39) and FIG. 11 the predicted amino acid (SEQ ID NO:40) sequences of human CARD-4Y; FIG. 12 shows the nucleotide (SEQ ID NO:41) and FIG. 13 the amino acid (SEQ ID NO:42) sequences of human CARD-4Z; and FIG. 14 shows an alignment of the CARD-4L, CARD-4Y, and CARD-4Z amino acid sequences generated by the Clustal program using a PAM250 residue weight table.

Example 5

Identification of Murine CARD-4

The CARD-4 polypeptide sequence was used to search databases of cDNA sequences and partial cDNA sequences using the TBLASTN program (version 1.4, BLOSUM62 search matrix, and a word length of 3) for murine CARD-4 cDNA clones. This search led to the identification of a partial murine CARD-4 clone designated murine CARD-4L. The rapid identification of cDNA ends procedure (RACE) was applied to the 5' end of the murine CARD-4L lone to elucidate the 5' end of the murine CARD-4L cDNA. FIG. 15 shows the murine CARD-4L nucleotide sequence SEQ ID NO:43), FIG. 16 shows the murine CARD-4L amino acid sequence (SEQ ID NO:44), and FIG. 17 shows an alignment of the murine CARD-4L and human CARD-4L amino acid sequences generated by the Clustal program using a PAM250 residue weight table.

Example 6

Identification of the Chromosomal Location of Human CARD-4

To determine the chromosomal location of the human CARD-4 gene, the polymerase chain reaction carried out with human CARD-4-specific primers card4t, with the 5' to 3' sequence agaaggtctggtcggcaaa (SEQ ID NO:45), and card4k, with the 5' to 3' sequence aagccctgagtggaagca (SEQ ID NO:46), was used to screen DNAs from a commercially available somatic cell hybrid panel. This analysis showed that human CARD-4 maps to chromosome 7 close to the SHGC-31928 genetic marker.

Example 7

Identification of CARD-3 in a Yeast Two-hybrid Screen for Proteins That Physically Interact With the CARD Domain of Human CARD-4

DNA encoding amino acids 1–145 of human CARD-4 comprising the CARD domain was cloned into a yeast two-hybrid screening vector to create a CARD-4, 1–145-GAL4 DNA-binding domain fusion for two-hybrid screening. The CARD-4, 1–145-GAL4 DNA-binding domain fusion was used to screen human mammary gland and human prostate two-hybrid libraries for gene products that could physically associate with CARD-4, 1–145. Twelve library plasmids expressing CARD4, 1–145 interacting proteins were found to contain the CARD-domain containing protein CARD-3 thus establishing a direct or indirect physical interaction between CARD-4 and CARD-3.

Example 8

Identification of hNUDC in a Yeast Two-hybrid Screen for Proteins That Physically Interact With the LRR Domain of Human CARD-4

DNA encoding amino acids 406–953 of human CARD-4L comprising the LRR domain was cloned into a yeast two-hybrid screening vector to create a CARD-4, 406–953-GAL4 DNA-binding domain fusion for two-hybrid screening. The CARD-4, 406–953-GAL4 DNA-binding domain fusion was used to screen a human mammary gland two-hybrid library for gene products that could physically associate with CARD-4, 406–953. One library plasmid expressing a CARD4, 406–953 interacting protein was found to contain the hNUDC protein, the human ortholog of the rat NUDC protein that has been implicated in nuclear movement (Morris et al., Curr. Biol. 8:603 [1998], Morris et al., Exp. Cell Res. 238:23 [1998]), thus establishing a physical interaction between CARD-4 and hNUDC.

Example 9

Discovery of Regulation by CARD-4 of NF-κB

In six transfection experiments, 293T cells coexpressing an NF-κB reporter plasmid (NF-κB-luciferase, Stratagene) and either pCI, pCI-CARD-4L, pCI-CARD-4S, pCI-APAFL, pCI-APAFS, or pCI-CARD-4LnoCARD were created. After 48 hours, cells were lysed and the relative luciferase activity was determined (Promega Kit) to assess NF-κB pathway activation by the gene expressed by the pCI-based plasmid in each transfected cell line. The cell lines containing pCI, pCI-APAFS, pCI-APAFL, and pCI-CARD-4LnoCARD had similar baseline levels of luciferase expression but the cell line containing pCI-CARD-4L had luciferase expression nine fold elevated relative to baseline and the cell line containing pCI-CARD4S had luciferase expression sixteen fold elevated relative to baseline. This result demonstrates induction by CARD-4S and CARD-4L of the NF-κB pathway. This CARD-4 mediated NF-κB pathway induction is dependent on the CARD-4 CARD domain because the pCI-CARD-4noCARD construct expressing CARD-4 lacking its CARD domain did not induce the luciferase reporter gene. In addition, the induction of the NF-κB pathway by CARD-4 is specific, as neither APAF-expressing construct in this experiment induced luciferase activation.

Example 10

Discovery of CARD-4 Enhancement of Caspase 9 Activity

In six transfection experiments, 293T cells coexpressing a beta galactosidase-expressing plasmid as a marker for viable cells and either pCI, pCI-CARD-4L, pCI-CARD-4S, pCI-CARD-4LnoCARD, pCI-APAF or pCI-casp9 were created. After 40 hours, cells were fixed and stained for beta-galactosidase expression and cell viability was determined by counting the number of beta galactosidase positive cells. Expression of pCI, pCI-CARD-4L, pCI-CARD-4S, pCI-CARD-4LnoCARD, and pCI-APAF did not result in loss of cell viability. As expected, expression of pCI-casp9 in 293T cells resulted in a loss of viability of about 75% of the cells in the experiment. It was next tested whether expression of CARD-4S, CARD-4L, CARD-4LnoCARD, or APAF would regulate caspase 9-mediated apoptosis. In five transfection experiments, 293T cells coexpressing a beta galactosidase-expressing plasmid as a marker for viable cells, pCI-casp9, and either pCI, pCI-CARD-4L, pCI-CARD-4S, pCI-CARD-4LnoCARD, pCI-APAF were created. After 40 hours, cells were fixed and stained for beta-galactosidase expression and cell viability was determined by counting the number of beta galactosidase positive cells. Expression of pCI or pCI-CARD-4LnoCARD in the caspase 9-expressing 293T cells had no effect on the caspase 9-induced apoptosis. However, pCI-CARD-4L, pCI-CARD-4S, and, as expected, pCI-APAF enhanced the level of caspase 9-induced apoptosis to 20 or less beta galactosidase positive cells per experiment from about 100 beta glactosidase positive cells per experiment. This experiment demonstrates that CARD-4 can enhance caspase 9-mediated apoptosis.

Example 11

Identification and Tissue Distribution of mRNA Species Expressed by the Human CARD-4 Gene Northern analysis of mRNAs extracted from adult human tissues revealed a 4.6 kilobase mRNA band that was expressed in most tissues examined. Highest expression was observed heart, spleen, placenta and lung. CARD-4 was also observed to be expressed in fetal brain, lung, liver and kidney. Cancer cell lines expressing the 4.6 kilobase CARD-4 mRNA include HeLa, K562, Molt4, SW480, A549 and melanoma. A larger 6.5 to 7.0 kilobase CARD-4 mRNA was expressed in heart, spleen, lung, fetal lung, fetal liver, and in the Molt4 and SW480 cell lines.

Example 12

Physical Association of CARD-4 wih CARD-4, CARD-3, Caspase 9, and BCLX

CARD-4S-specific PCR primers with the 3' primer encoding the HA epitope tag were used to amplify the CARD-4S gene epitope tagged with HA and this PCR product was cloned into the mammalian expression vector pCI. CARD-4S-specific PCR primers with the 3' primer encoding the MYC epitope tag were used to amplify the CARD-4S gene epitope tagged with MYC and this PCR product was cloned into the mammalian expression vector pCI. CARD-3-specific PCR primers with the 5' primer encoding the MYC epitope tag were used to amplify the CARD-3 gene epitope tagged with MYC and this PCR product was cloned into the mammalian expression vector pCI. Caspase 9-specific PCR primers with the 3' primer encoding the MYC epitope tag were used to amplify the caspase 9 gene epitope tagged with MYC and this PCR product was cloned into the mammalian expression vector pCI. BCLX-specific PCR primers with the 3' primer encoding the MYC epitope tag were used to amplify the BCLX gene epitope tagged with MYC and this PCR product was cloned into the mammalian expression vector pCI. In four transfection experiments, 293T cells coexpressing pCI-CARD-4ScHA and either pCI-CARD-4ScMYC, pCI-CARD3nMYC, pCI-casp9cMYC, or pCI-BCLXcMYC were created. Cells from each transfected line were lysed and an immunoprecipitation procedure was carried out on each lysate with an anti-HA epitope tag antibody to precipitate the CARD-4ScHA expressed by each cell line and any physically associated proteins. Immunoprecipitated proteins were separated by electrophoresis on denaturing polyacrylamide gels, transferred to nylon filters, and probed with an anti-MYC epitope tag antibody in a Western blotting experiment to determine whether the MYC-tagged protein that was coexpressed with the CARD-4ScHA protein had coimmunoprecipitated with the CARD-4ScHA protein. In this experiment, CARD-4, CARD-3, caspase 9, and BCLX were found to coimmunoprecipitate with CARD-4.HA-epitope tagged CARD4L and CARD4(518) constructs analogous to pCI-CARD-4ScHA were generated. These constructs were used in experiments similar to those described in the previous paragraph. In these experiments, the proteins that coimmunoprecipitated with the CARD-4ScHA protein that were tested also coimmunoprecipitated with CARD4L and CARD4 (518).Equivalents Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound that alters the binding of a CARD-4L polypeptide to a CARD-3 polypeptide, the method comprising:

(a) measuring the binding of a polypeptide comprising the amino acid sequence of SEQ ID NO:8 to a polypeptide comprising the amino acid sequence of SEQ ID NO:2 in the presence of a test compound; and (b) comparing the binding measured in step (a) to the binding of the polypeptide comprising the amino acid sequence of SEQ ID NO:8 to the polypeptide comprising the amino acid sequence of SEQ ID NO:2 in the absence of the test compound; and (c) determining that the test compound is a compound that alters the binding of a CARD-4L polypeptide to a CARD-3 polypeptide if the binding of the polypeptide comprising the amino acid sequence of SEQ ID NO:8 to the polypeptide comprising the amino acid sequence of SEQ ID NO:2 in the presence of test compound differs from the binding of the polypeptide comprising the amino acid sequence of SEQ ID NO:8 to the polypeptide comprising the amino acid sequence of SEQ ID NO:2 in the absence of the test compound.

2. The method of claim 1 wherein step (a) comprises exposing a cell expressing the polypeptide comprising the amino acid sequence of SEQ ID NO:8 and a polypeptide comprising the amino acid sequence of SEQ ID NO:2 to the test compound.

3. A method for identifying a compound that alters the binding of a CARD-4S polypeptide to a CARD-3 polypeptide, the method comprising:

(a) measuring the binding of a polypeptide comprising the amino acid sequence of SEQ ID NO:26 to a polypeptide comprising the amino acid sequence of SEQ ID NO:2 in the presence of a test compound; and (b) comparing the binding measured in step (a) to the binding of the polypeptide comprising the amino acid sequence of SEQ ID NO:26 to the polypeptide comprising the amino acid sequence of SEQ ID NO:2 in the absence of the test compound; and (c) determining that the test compound is a compound that alters the binding of a CARD-4S polypeptide to a CARD-3 polypeptide if the binding of the polypeptide comprising the amino acid sequence of SEQ ID NO:26 to the polypeptide comprising the amino acid sequence of SEQ ID NO:2 in the presence of test compound differs from the binding of the polypeptide comprising the amino acid sequence of SEQ ID NO:26 to the polypeptide comprising the amino acid sequence of SEQ ID NO:2 in the absence of the test compound.

4. The method of claim 3 wherein step (a) comprises exposing a cell expressing the polypeptide comprising the amino acid sequence of SEQ ID NO:26 and a polypeptide comprising the amino acid sequence of SEQ ID NO:2 to the test compound.

5. A method for identifying a compound that alters the binding of a CARD-4L polypeptide to a CARD-4L polypeptide, the method comprising:

(a) measuring the binding of a polypeptide comprising the amino acid sequence of SEQ ID NO:8 to a polypeptide comprising the amino acid sequence of SEQ ID NO:8 in the presence of a test compound; and (b) comparing the binding measured in step (a) to the binding of the polypeptide comprising the amino acid sequence of SEQ ID NO:8 to the polypeptide comprising the amino acid sequence of SEQ ID NO:8 in the absence of the test compound; and (c) determining that the test compound is a compound that alters the binding of a CARD-4L polypeptide to a CARD-4L polypeptide if the binding of the polypeptide comprising the amino acid sequence of SEQ ID NO:8 to the polypeptide comprising the amino acid sequence of SEQ ID NO:8 in the presence of test compound differs from the binding of the polypeptide comprising the amino acid sequence of SEQ ID NO:8 to the polypeptide comprising the amino acid sequence of SEQ ID NO:8 in the absence of the test compound.

6. The method of claim 5 wherein step (a) comprises exposing a cell expressing the polypeptide comprising the amino acid sequence of SEQ ID NO:8.

7. A method for identifying a compound that alters the binding of a CARD-4S polypeptide to a CARD-4S polypeptide, the method comprising:

(a) measuring the binding of a polypeptide comprising the amino acid sequence of SEQ ID NO:26 to a polypeptide comprising the amino acid sequence of SEQ ID NO:26 in the presence of a test compound; and (b) comparing the binding measured in step (a) to the binding of the polypeptide comprising the amino acid sequence of SEQ ID NO:26 to the polypeptide comprising the amino acid sequence of SEQ ID NO:26 in the absence of the test compound; and (c) determining that the test compound is a compound that alters the binding of a CARD-4L polypeptide to a CARD-4L polypeptide if the binding of the polypeptide comprising the amino acid sequence of SEQ ID NO:26 to the polypeptide comprising the amino acid sequence of SEQ ID NO:26 in the presence of test compound differs from the binding of the polypeptide comprising the amino acid sequence of SEQ ID NO:8 to the polypeptide comprising the amino acid sequence of SEQ ID NO:8 in the absence of the test compound.

8. The method of claim 7 wherein step (a) comprises exposing a cell expressing the polypeptide comprising the amino acid sequence of SEQ ID NO:26.

9. A method for identifying a compound that alters the binding of a CARD-4L polypeptide to caspase-9, the method comprising:

(a) measuring the binding of a polypeptide comprising the amino acid sequence of SEQ ID NO:8 to caspase-9 in the presence of a test compound; and (b) comparing the binding measured in step (a) to the binding of the polypeptide comprising the amino acid sequence of SEQ ID NO:8 to caspase-9 in the absence of the test compound; and (c) determining that the test compound is a compound that alters the binding of a CARD-4L polypeptide to caspase-9 if the binding of the polypeptide comprising the amino acid sequence of SEQ ID NO:8 to caspase-9 in the presence of test compound differs from the binding of the polypeptide comprising the amino acid sequence of SEQ ID NO:8 to caspase-9 in the absence of the test compound.

10. The method of claim 9 wherein step (a) comprises exposing a cell expressing the polypeptide comprising the amino acid sequence of SEQ ID NO:8 and caspase-9.

11. A method for identifying a compound that alters the binding of a CARD-4L polypeptide to BCL-X, the method comprising:

(a) measuring the binding of a polypeptide comprising the amino acid sequence of SEQ ID NO:8 to BCL-X in the presence of a test compound; and (b) comparing the binding measured in step (a) to the binding of the polypeptide comprising the amino acid sequence of SEQ ID NO:8 to BCL-X in the absence of the test compound; and (c) determining that the test compound is a compound that alters the binding of a CARD-4L polypeptide to BCL-X if the binding of the polypeptide comprising the amino acid sequence of SEQ ID NO:8 to BCL-X in the presence of test compound differs from the binding of the polypeptide comprising the amino acid sequence of SEQ ID NO:8 to BCL-X in the absence of the test compound.

12. The method of claim 11 wherein step (a) comprises exposing a cell expressing the polypeptide comprising the amino acid sequence of SEQ ID NO:8 and BCL-X.

13. A method for identifying a compound that alters the binding of a CARD-4L polypeptide to caspase-9, the method comprising:

(a) measuring the binding of a polypeptide comprising the amino acid sequence of SEQ ID NO:26 to caspase-9 in the presence of a test compound; and (b) comparing the binding measured in step (a) to the binding of the polypeptide comprising the amino acid sequence of SEQ ID NO:26 to caspase-9 in the absence of the test compound; and (c) determining that the test compound is a compound that alters the binding of a CARD-4L polypeptide to caspase-9 if the binding of the polypeptide comprising the amino acid sequence of SEQ ID NO:26 to caspase-9 in the presence of test compound differs from the binding of the polypeptide comprising the amino acid sequence of SEQ ID NO:26 to caspase-9 in the absence of the test compound.

14. The method of claim 13 wherein step (a) comprises exposing a cell expressing the polypeptide comprising the amino acid sequence of SEQ ID NO:26 and caspase-9.

15. A method for identifying a compound that alters the binding of a CARD-4S polypeptide to BCL-X, the method comprising:

(a) measuring the binding of a polypeptide comprising the amino acid sequence of SEQ ID NO:26 to BCL-X in the presence of a test compound; and (b) comparing the binding measured in step (a) to the binding of the polypeptide comprising the amino acid sequence of SEQ ID NO:26 to BCL-X in the absence of the test compound; and (c) determining that the test compound is a compound that alters the binding of a CARD-4S polypeptide to BCL-X if the binding of the polypeptide comprising the amino acid sequence of SEQ ID NO:26 to BCL-X in the presence of test compound differs from the binding of the polypeptide comprising the amino acid sequence of SEQ ID NO:26 to BCL-X in the absence of the test compound.

16. The method of claim 15 wherein step (a) comprises exposing a cell expressing the polypeptide comprising the amino acid sequence of SEQ ID NO:26 and BCL-X.

17. A method for identifying a compound that alters the binding of a CARD-4L polypeptide to NUDC, the method comprising:

(a) measuring the binding of a polypeptide comprising the amino acid sequence of SEQ ID NO:8 to NUDC in the presence of a test compound; and (b) comparing the binding measured in step (a) to the binding of the polypeptide comprising the amino acid sequence of SEQ ID NO:8 to NUDC in the absence of the test compound; and (c) determining that the test compound is a compound that alters the binding of a CARD-4L polypeptide to NUDC if the binding of the polypeptide comprising the amino acid sequence of SEQ ID NO:8 to NUDC in the presence of test compound differs from the binding of the polypeptide comprising the amino acid sequence of SEQ ID NO:8 to NUDC in the absence of the test compound.

18. The method of claim 17 wherein step (a) comprises exposing a cell expressing the polypeptide comprising the amino acid sequence of SEQ ID NO:8 and NUDC.

19. A method for identifying compounds that alter the expression of CARD-4L, the method comprising:

(a) measuring the expression of a polypeptide comprising the amino acid sequence of SEQ ID NO:8 in a cell exposed a test compound;

(b) comparing the expression measured in step (a) to the expression of the polypeptide comprising the amino acid sequence of SEQ ID NO:8 in a cell not exposed to the test compound;

(c) and determining that the test compound is a compound that alters the expression of CARD-4L if the expression measured in step (a) differs from the expression of the polypeptide comprising the amino acid sequence of SEQ ID NO:8 in the cell not exposed to the test compound.

20. A method for identifying compounds that alter the expression of CARD-4S, the method comprising:

(a) measuring the expression of a polypeptide comprising the amino acid sequence of SEQ ID NO:26 in a cell exposed a test compound;

(b) comparing the expression measured in step (a) to the expression of the polypeptide comprising the amino acid sequence of SEQ ID NO:26 in a cell not exposed to the test compound;

(c) and determining that the test compound is a compound that alters the expression of CARD-4S if the expression measured in step (a) differs from the expression of the polypeptide comprising the amino acid sequence of SEQ ID NO:26 in the cell not exposed to the test compound.

21. A method for identifying compounds that alter the expression of CARD-4L, the method comprising:

(a) measuring the expression of a nucleic acid molecule comprising SEQ ID NO:9 in a cell exposed a test compound;

(b) comparing the expression measured in step (a) to the expression of the nucleic acid molecule comprising SEQ ID NO:9 in a cell not exposed to the test compound;

(c) and determining that the test compound is a compound that alters the expression of CARD-4L if the expression measured in step (a) differs from the expression of the nucleic acid molecule comprising SEQ ID NO:9 in the cell not exposed to the test compound.

22. A method for identifying compounds that alter the expression of CARD-4S, the method comprising:

(a) measuring the expression of a nucleic acid molecule comprising SEQ ID NO:27 in a cell exposed a test compound;

(b) comparing the expression measured in step (a) to the expression of the nucleic acid molecule comprising SEQ ID NO:27 in a cell not exposed to the test compound;

(c) and determining that the test compound is a compound that alters the expression of CARD-4S if the expression measured in step (a) differs from the expression of the nucleic acid molecule comprising SEQ ID NO:27 in the cell not exposed to the test compound.

* * * * *